US006376649B1

(12) United States Patent
Semple et al.

(10) Patent No.: US 6,376,649 B1
(45) Date of Patent: Apr. 23, 2002

(54) METHODS FOR THE SYNTHESIS OF α-HYDROXY-β-AMINO ACID AND AMIDE DERIVATIVES

(75) Inventors: Joseph E. Semple; Odile E. Levy, both of San Diego, CA (US)

(73) Assignee: Corvas International, Inc., San Diego, CA (US)

( * ) Notice: Subject to any disclaimer, the term of this patent is extended or adjusted under 35 U.S.C. 154(b) by 0 days.

(21) Appl. No.: 09/216,134

(22) Filed: Dec. 18, 1998

(51) Int. Cl.$^7$ ............................. G07K 1/00; G01N 33/00

(52) U.S. Cl. ...................... 530/334; 530/332; 530/335; 530/336; 530/337; 530/342; 530/343; 530/345; 436/85; 436/91; 436/92

(58) Field of Search ................................ 530/334, 332, 530/335, 336, 337, 342, 343, 341; 436/85, 91, 92

(56) References Cited

U.S. PATENT DOCUMENTS 5,371,072 A * 12/1994 Webb et al. ................. 514/18
5,597,804 A * 1/1997 Webb et al. ................. 514/18

OTHER PUBLICATIONS

Bastos, Margarita; Maeii, N. Joe; Abeles, Robert H. Inhibitors of human heart chymase based on a peptide library. Proc. Natl. Acad. Sci. USA, vol. 92, pp. 6738–6742, Jul. 1995.
Carofiglio, Tommaso; Cozzi, Pier Giorgio; Floriani, Carlo. Nonorganometallic Pathway of the Passerini Reaction Assisted by Titanium Tetrachloride. Organometallics 1993, 12, 2726–2736.
Dhanoa, Daljit S.; Parsons, William J.; Greenlee, William J.; Patchett, Arthur A. The Synthesis of Potent Macrocyclic Renin Inhibitors, Tetrahedron Letters, vol. 33, No. 13, pp. 1725–1728, 1992.
Falck, J.R. and Manna, Sukumar. An Intramolecular Passerini Reaction: Synthesis of Hydrastine. Tetrahedron Letters, vol. 22, pp 619–620, 1981.
Hagedorn, Isle: Eholzer, Ulrich. Einsufige Synthese von α–Hydroxysaure–amiden durch Abwandlung der Passerini–Reaktion. Isonirrile, VII[1] Eingegangen am 29, Sep. 1964.
Hagihara, Masahiko and Stuart L. Schreiber. Reassignment of Stereochemistry and Total Synthesis of the Thrombin Inhibitor Cyclotheonamide B. American Chemical Society., 1992.
Harbeson, Scott L. et al. Stereospecific Synthesis of Peptidy α–Keto Amides as Inhibitors of Calpain. J. Med. Chem. 37. 2918–2929, 1994.
Iizuka, Kinji et al. Orally Potent Human Renin Inhibitors Derived from Angiotensinogen Transition State: Design, Synthesis, and Mode of Interaction. J. Med. Chem., 33, 2707–2714, 1990.

Iwanowicz, Edwin J. et al. α–Hydroxy– And α–Ketoester Functionalized Thrombin Inhibitors. Bioorganic & Medical Chemistry Letters, vol. 2, No. 12, pp. 1607–1612, 1992.
Iwanowicz, Edwin J. et al. Retro–Binding Tripeptide Thrombin Active–Site–Inhibitors: Discovery, Synthesis, and Molecular Modeling. J. Med. Chem. 37, 2122–2124, 1994.
Jen, Timothy et al. Adrenergic Agents 7.[1] Synthesis and β–Adrenergic Agonist Activity of Several 2–Pyridylethanolamines. J. Med. Chem., vol. 20, No. 10, 1977.
Lumma, William C., J. Org. Chem., 46:3668–3671 (1987), Modification of the Passerini Reaction: Facile Synthesis of Analogues of Isoproterenol and (Aryloxy) propanolamine β–Adrenergic Blocking Agents.
Mimoto, Tsutomu et al., Chem. Pharm. Bull. 40(8):2251–2253 (1992), Kynostatin (KNI)–227 and –272, Highly Potent Anti–HIV Agents Conformationally Constrained Tripeptide Inhibitors of HIV Protease Containing Allophenylnorstatine[1,2].
Mukaiyama, Teruaki et al. A Convenient Method For The Synthesis of α–Alkoxycarboxamide Derivatives. Chemistry Letters, pp. 1457–1458, 1974.
Seebach, Dieter et al. Scope and Limitations of the TiCl$_4$–Mediated Additions of Isocyanides to Aldehydes and Ketones with Formation of α–Hydroxycarboxylic Acid Amides[1], Chem. Ber. 121:507–517 (1988).
Semple, J. Edward et al, Synthesis and Biological Activity of $P_2$–$P_4$ Azapeptidomimetic $P_1$–Ketoargininamide Derivatives: A Novel Class of Serine Protease Inhibitors[1], Biorg. & Med., Chem. Letters, 7(3):315–320 (1997).
Schiess Martin' and Dieter Seebach. N–Methyl–C–(trichlortitanio) formimidoylchlorid, Ein effizientes Reagenz zur Homologisierung von Aldehyden und Ketonen zu α–Hydroxy–carbonsaureamiden. Helvetica Chimica Acta, vol. 66, Fasc. 5 (1983)–Nr. 155, p. 1618.
Schmidt, Ulrich and Weinbrenner, Steffen, The Synthesis of Eurystation A[1], Chem. Soc. Chem Commun. (1994), pp. 1003–1004.
B. Zeeh and E. Muller. Swissaure–katalysierte Umsetzung von aliphatischen Ketonen . . . Liebigs Ann. Chem. 715, 47–51 (1968).

* cited by examiner

Primary Examiner—Christopher S. F. Low
Assistant Examiner—Abdel A. Mohamed
(74) Attorney, Agent, or Firm—Pillsbury Winthrop LLP

(57) ABSTRACT

Methods for the synthesis of α-hydroxy-β-amino acid and amide derivatives and α-ketoamide derivatives and novel derivatives made by these methods are provided. These methods involve reacting a N-terminally blocked (protected) aminoaldehyde with an isonitrile and a carboxylic acid to give an amino-α-acyloxy carboxamide. The acyloxy group may be removed to give the derivative. Alternatively the protecting group is removed and acyl shift occurs to give the derivative. These derivatives are useful in the synthesis of compounds such as peptidyl α-ketoamides and α-hydroxy-β-carboxylic acid and amide derivatives. Certain of these compounds have been reported to have activity as inhibitors of proteases, such as serine proteases and cysteine proteases.

21 Claims, 20 Drawing Sheets

Figure 1A
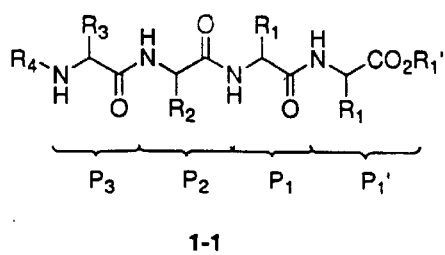
1-1
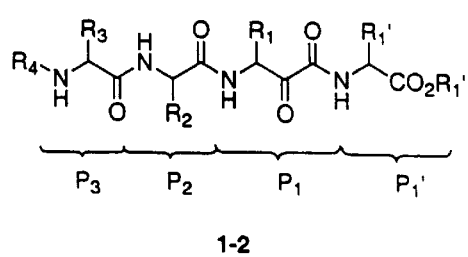
1-2
Figure 1B
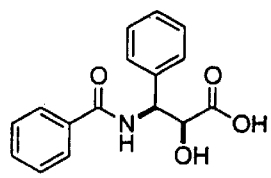
Figure 1C
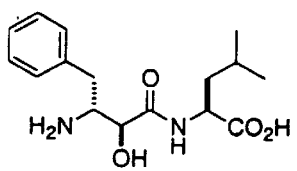
Figure 1D
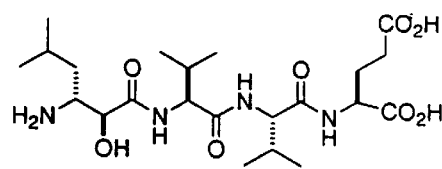

4-1, $P_1$-α-Ketoamide Target

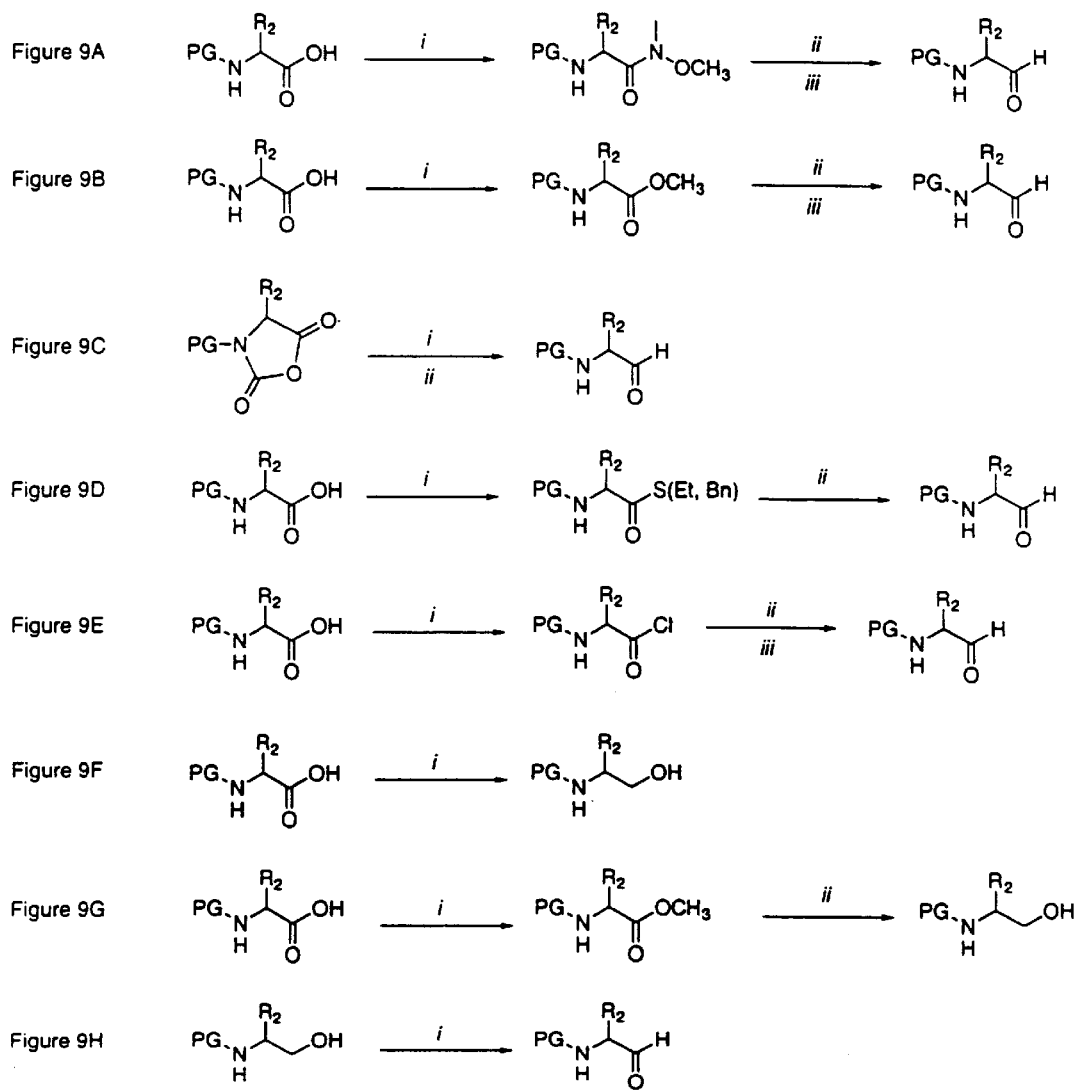

17-10

[B]

[C]

[Eurystatin]

[G]

| Mild Organic Base* | % Yield 3 |
|---|---|
| 2,6-di-t-Butyl Pyridine | 72 |
| 2,4,6-Collidine | 71 |
| 2,6-Lutidine | 68 |
| Pyridine | 60 |
| N-Methylmorpholine | 41 |
| DABCO | 33 |
| 4-N,N-Dimethylaminopyridine | 18 |
| N,N-Diisopropylethylamine | 15 |

METHODS FOR THE SYNTHESIS OF α-HYDROXY-β-AMINO ACID AND AMIDE DERIVATIVES

FIELD OF THE INVENTION

The present invention relates to methods for the synthesis of α-hydroxy-β-amino acid and amide derivatives, and methods of using these intermediates in the synthesis of a variety of more complex peptidyl α-ketoamides and α-hydroxy-β-amino carboxylic acid derivatives.

BACKGROUND AND INTRODUCTION TO THE INVENTION

α-Hydroxy-β-aminocarboxylic acid and amide derivatives are found in a variety of natural products and pharmaceutical substances. Subunits incorporating the α-hydroxy-β-aminocarboxylic acid motif have been termed "norstatine" derivatives, and serve as key intermediates for the synthesis of the general class of $P_1$-α-ketocarboxylic transition-state inhibitors of serine or cysteine proteases. Such inhibitors are finding increasing applications in medicine for the treatment of a diverse array of disease states including thrombosis, cancer, and osteoporosis. Towards this end, α-hydroxy-β-aminocarboxylic acid, ester and amide derivatives serve an important role as the most common precursors for the preparation of these α-ketocarboxylic-acid-incorporating drug candidates.

Electrophilic α-dicarbonyl compounds are regarded as interesting and highly reactive functional arrays which are capable of undergoing a myriad of transformations. Such chemical properties can be exploited in novel and therapeutically useful ways by strategically incorporating these reactive α-ketocarboxylic moieties into a peptidic or peptidomimetic matrix. The α-keto-carbonyl group is highly electropositive due to the presence of the adjoining electron-withdrawing amide functionality. Hence, it is highly reactive towards conventional biological nucleophiles encountered at the catalytic triad of a protease active site, including hydroxyl, thiol, and amino nucleophiles.

A prototypical serine protease substrate for which a suitable inhibitor is to be designed is Compound 1-1, depicted in FIG. 1A. The target site for this protease is composed of four amino acid residues: $P_3, P_2, P_1, P_1'$. In this and the derived ketoamide inhibitor structure 1-2, the notation $P_1, P_2, \ldots P_n$ denotes the position of a peptide residue relative to the scissile bond which is defined as $P_1$-$P_1'$ of the substrate undergoing cleavage (Schechter and Berger, *Biochem. Biophys. Res. Commun.* 1967, 27: 157–162).

Upon entering and docking into the active site of a serine or cysteine protease, the peptidic or peptidomimetic backbone portion $P_n \ldots P_n'$ of target inhibitor 1-2 provides an array of important contact points which are stabilizing and energetically favorable. Such key geometric, hydrophobic, and electrostatic interactions help to bind the inhibitor to the protease, while the strategically positioned $P_1$ α-ketoamide function serves to inactivate the protease via formation of a slowly reversible covalent bond with the critical serine hydroxyl or cysteine thiol functions at the S1 site. The formation of such tetrahedral intermediates effectively ties up and, therefore, deactivates the active site, ultimately leading to inhibition of the enzyme.

Due to the highly stereospecific nature of several critical interactions at the enzyme active site, the relative and absolute stereochemistry of both $P_1$-α- and β-positions has a profound effect on the overall biological activity and selectivity profiles of the target drugs, e.g. protease inhibitors, into which these motifs are incorporated. As a result, the stereospecific synthesis of these classes of compounds has received increasing attention over the past decade.

Several prominent examples have recently emerged that illustrate the variety and importance of the α-hydroxy-β-aminocarboxylic acid and amide derivatives (see FIGS. 1B to 1D). For instance, the natural product paclitaxel (Taxol®), a potent anticancer drug, features a biologically essential C-13 N-benzoyl-3-phenylisoserine side chain esterified to a secondary alcohol function. FIG. 1B depicts the N-benzoyl-3-phenylisoserine side chain. The natural product bestatin (structure depicted in FIG. 1C), also an α-hydroxy-β-amino amide derivative, is reported to possess anticancer, immune response modifier, as well as amino-peptidase B (AP-B), leucine aminopeptidase (LAP), and prolyl endopeptidase (PEP) enzyme inhibitory activities. Amastatin (structure depicted in FIG. 1D), a related peptidic natural product, is reported to demonstrate amino-peptidase A (AP-A) and leucine aminopeptidase enzyme inhibitory properties.

α-Hydroxy-β-amino amide derivatives also are useful inhibitors of aspartyl proteases (see FIG. 2A). The promising synthetic HIV protease inhibitor Kynostatin (2-2) (Mimoto, et al., *Chem. Pharm. Bull.* 40(8): 2251–2253 (1992)) which incorporates an allophenylnorstatine (Apns) (2-1) moiety, is an α-hydroxy-β-amino amide derivative. Some synthetic renin inhibitors (2-4 and 2-5) feature the related cyclohexylnorstatine (Chns) residue (2-3) (see FIG. 2B) (Iizuka, et al., *J. Med. Chem.* 33: 2707–2714 (1990); Dhanoa, et al., *Tetrahedron Letters*, 33(13): 1725–1728 (1992)). In the HIV and renin inhibitors, the α-hydroxy-β-aminocarboxylic, or "norstatine", residue is employed as a hydroxymethyl carbonyl peptide bond isostere, which in turn serves as the $P_1$-transition state mimic of peptide hydrolysis.

Inhibition of thrombin, a key terminal serine protease in the blood coagulation cascade, has been the subject of recent intensive investigation. Within the α-hydroxy-β-amino ester group of compounds (3-1), the thrombin inhibitor BMS 181316 incorporates a $P_1$-lysine derived α-hydroxy-β-aminoester residue (3-2) (see FIG. 3A). (Iwanowicz et al., *Bioorganic & Medicinal Chemistry Letters*, 2(12); 1607–1612 (1992)).

A variety of electrophilic $P_1$-transition state compounds have been discovered and developed for use as thrombin inhibitors. From this general family of inhibitors, α-ketoamide derivatives have figured prominently with regard to outstanding inhibitory potency. Such peptidomimetic inhibitors have been efficacious both in vitro and in vivo, for example, in animal models of small vein thrombosis and deep vein thrombosis (DVT). By elaboration of α-hydroxyhomoarginine precursors (3-3 of FIG. 3B), a series of $P_1$-ketoargininamide derivatives were prepared which expressed potent thrombin inhibitory properties (see, e.g., U.S. Pat. Nos. 5,371,072; 5,597,804; 5,656,600; and 5,670,479). A large number of variations in the $P_2$–$P_4$ residues as well as $P_1'$ residues were investigated which provided a family of active and selective thrombin inhibitors. See, e.g., 3-4 of FIG. 3B.

In a related class of protease inhibitors, $P_1$-ketonorvalinamide peptide derivatives showed high inhibitory activity against a family of intracellular calpains. The calpains are cysteine proteases responsible for neurodegeneration which accompanies either global or focal cerebral ischemia. Such neutral $P_1$-ketoamide inhibitors were prepared from 2-hydroxy-3-aminohexanoic acid (3-5 of FIG. 3C). Several related neutral, lipophilic P$_1$-ketoamide derivatives have found application as inhibitors for a broad range of cysteine protease enzymes. See, e.g., 3-6 of FIG. 3C. (Harbeson et al., *J. Med. Chem.*, 37:2918–2929 (1994)).

There have been reports describing the synthesis of peptidal α-ketoamide derivatives which are useful as enzyme inhibitors. The most widely utilized method of preparation is based upon a conventional multi-step solution phase approach and is outlined in FIG. 4A/Scheme 1. (See U.S. Pat. Nos. 5,371,072; 5,597,804; 5,656,600; and 5,670,479; Semple et al., *Bioorg. Med. Chem. Lett.* 7:315 (1997); Maryanoff et al., *J. Am. Chem. Soc.* 117:1225 (1995); and Harbeson et al., *J. Med. Chem.* 37:2918 (1994).) A protected amino acid derivative 4-2 (PG denotes protecting group) is elaborated via known methods to the protected α-aminoaldehyde derivative 4-3. The α-hydroxy-β-amino ester intermediate 4-4 is prepared from 4-3 via a four-step process. Thus, reaction of 4-3 with saturated aqueous sodium bisulfite produces the corresponding bisulfite addition adduct. Treatment of the adduct with aqueous basic potassium cyanide generates a cyanohydrin intermediate. Hydrolysis of the cyanohydrin intermediate is usually accomplished with a mineral acid such as hydrochloric acid at about reflux temperature. Due to the rather drastic reaction conditions, this process generally affords the fully deprotected α-hydroxy-β-amino acid intermediate. Esterification of this material with a suitable alcohol like methanol under standard acid-catalyzed conditions then affords the α-hydroxy-β-amino ester intermediate 4-4.

The amino group of 4-4 is reprotected, for example, as the N-Boc derivative by using Boc anhydride under mildly basic conditions in a two-phase solvent system, typically consisting of tetrahydrofuran and water, and affords 4-5 which is now suitably protected to allow for efficient subsequent peptide coupling reactions. Hydrolysis of the ester group of 4-5 with an aqueous alkali hydroxide such as lithium hydroxide and acidification affords a carboxylic acid intermediate. Coupling of a P$_1$' aminoester intermediate with this intermediate carboxylic acid via standard peptide coupling reagents produces 4-6.

The P$_1$-Boc amino-protecting group is then cleaved off by n acid catalyst such as trifluoroacetic acid or hydrogen chloride and the resultant amine salt is elaborated via standard peptide coupling protocols in a reiterative fashion to afford P$_n$ . . . P$_1$ peptidic P$_1$-α-hydroxyamide derivative. Optional orthogonal deprotection of the peptide side chains followed by a final oxidation step affords the target peptidal α-ketoamide derivative 4-1.

An alternative and milder route to peptidal α-ketoamide derivatives which has received attention but generally proceeds in modest to poor overall yields is depicted in FIG. 4B/Scheme 2. (See, Iwanowicz et al., *Bioorg. Med. Chem. Lett.* 2:1607 (1992); Schreiber et al., *J. Am. Chem. Soc.* 114:6570 (1992).) The reaction sequence commences by reaction of the blocked aminoaldehyde 4-7 with the lithium salt of ethyl orthothioformate at low temperatures of about −78° C. to −20° C. A mercuric chloride-mercuric oxide assisted cleavage of the resultant intermediate in methanolic milieu then generates intermediate 4-8 whose amino function may be protected by a variety of groups, including the Boc group discussed for 4-5 prepared above by the first route. This intermediate can be hydrolyzed to the corresponding carboxylic acid, coupled with a suitable P$_1$' amino acid residue and elaborated as described above to afford a peptidal α-ketoamide target 4-1.

Other protocols which are finding increasing popularity adopt this methodology and utilize solid phase synthesis technology. (See, e.g., Abeles et al., *Proc. Natl. Acad. Sci. (USA)* 92:6738 (1995).)

By possessing a divalent carbon atom, the isonitrile functional group shows unusual reactivity profiles and, as such, has shown the propensity to participate in multiple-component reactions. In 1921, Passerini described an unusual and potentially highly useful three-component reaction of an isonitrile R$_1$NC (5-1) with a carbonyl compound such as an aldehyde R$_2$CHO (5-2) and a carboxylic acid derivative R$_3$CO$_2$H (5-3). As depicted in FIG. 5/Scheme 3, the three components assemble to generate an intermediate 5-4. Upon subsequent acyl shift and proton transfer, a considerably more complex α-acyloxycarboxamide derivative 5-5 is obtained. Such a reaction takes place under very mild conditions, typically in the temperature range of about −78° C. to about 80° C., optionally in the presence of suitable solvents including methanol or dichloromethane.

Since its discovery, the so-called Passerini reaction has been studied rather sporadically and no definitive systematic investigations which might lead to generally useful preparative protocols appear to have been reported. Various inter- and intra-molecular variants have been described, but these reports failed to provide a generally useful synthetic method. (See generally, Passerini, *Gazz. Chim. Ital.* 51:126 (1921); Passerini and Ragni, *Gazz. Chim. Ital.* 61:964 (1931); Ugi et al., in "Isonitrile Chemistry", Chapter 7, Academic Press, New York, N.Y. (1971). For intramolecular version, see Falck and Manna, *Tet. Lett.* 22:619 (1981). For acid-catalyzed versions, see, Hagedorn and Eholzer, *Chem. Ber.* Jahrg. 98:936 (1965); Kaiser et al., *J. Med. Chem.* 20:1258 (1977); and Lumma et al., *J. Org. Chem.* 46:3668 (1981). For Lewis-acid catalyzed versions to produce α-hydroxyamides directly, see, Muller and Zeeh, *Liebigs Ann. Chem.* 696:72 (1966); Muller and Zeeh, *Liebigs Ann. Chem.* 715:47 (1968); Mukaiyama et al., *Chem. Lett.* 1994 1457–1458 (1994); Seebach and Schiess, Helv. Chim. Acta 66:1618 (1983); Seebach et al., *Chem. Ber.* 121:507 (1988); Floriani et al., *Organometallics* 12:2726 (1993). For Eurystatin A total synthesis, see, Schmidt and Weinbrenner, *J. Chem. Soc. Chem. Commun.* 1994 1003 (1994).)

The present invention provides new methods for the synthesis of α-hydroxy-β-aminoamide derivatives and α-hydroxyl-β-amino carboxylic acid derivatives, which can be used as intermediates in the synthesis of known and new compounds incorporating an α-ketoamide bond.

SUMMARY OF INVENTION

The present invention provides novel methods for the synthesis of α-hydroxyl-β-amino acid and amide derivatives. These derivatives are useful as intermediates for synthesis of peptidyl α-ketoamides and α-hydroxyl-β-amino carboxylic acid derivatives which are useful as inhibitors of certain proteases, including serine and cysteine proteases.

These methods involve reacting together an N-terminally blocked (protected) amino aldehyde with an isonitrile and a carboxylic acid to give an amino α-acyloxy carboxamide. The acyloxy group may be removed to give the derivative. Alternatively, the protecting group is removed and acyl shift takes place to give the derivative.

Among other factors, the present invention provides novel methods that allow for a more direct synthetic route with improved yields of compounds which incorporate an α-hydroxyl-β-amino ester or an α-ketoamide moiety. As noted in the Background and Introduction to the Invention, a number of compounds having an α-hydroxyl-β-amino ester or α-ketoamide moiety have been reported as useful as inhibitors of certain proteases. The methods of the present invention provide an improved synthetic route to intermediates for the end target compounds, with economy of synthesis, namely fewer synthetic steps, improved yields, less consumption of reagents and fewer side products than are obtained following conventional synthetic routes.

Accordingly, according to one aspect of the invention, provided are methods for making an α-hydroxyl-β-amino carboxylic acid of formula (A):

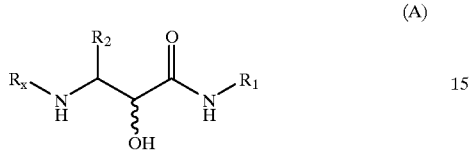

(A)

wherein
(i) $R_x$ is —PG or —C(O)$R_3$ where PG is a protecting group;
(ii)
(a) $R_1$, $R_2$ and $R_3$ are independently selected from the group consisting of alkyl of 1 to about 12 carbon atoms, cycloalkyl of 3 to about 12 carbon atoms, alkenyl of 2 to about 12 carbon atoms, cycloalkenyl of 5 to about 12 carbon atoms, and alkynyl 3 to about 12 carbon atoms, all optionally substituted with 1 to 3 substituents independently selected from $Y_1$, $Y_2$ and/or $Y_3$; aryl of about 5 to about 14 carbon atoms which is optionally mono-, di- or tri- substituted with $Y_1$, $Y_2$, and/or $Y_3$; heteroaryl of about 5 to about 14 ring atoms, with the ring atoms selected from carbon atoms and heteroatoms, wherein the heteroatoms are selected from oxygen, nitrogen and sulfur and which is optionally mono-, di-, tri- substituted with $Y_1$, $Y_2$ and/or $Y_3$; aralkyl of about 6 to about 18 carbon atoms which is optionally mono-, di- or tri-substituted on the aryl ring with $Y_1$, $Y_2$ and/or $Y_3$; and heteroaralkyl of about 5 to about 18 carbon atoms having about 5 to about 14 ring atoms with the ring atoms selected from carbon atoms and heteroatoms, wherein the heteroatoms are selected from oxygen, nitrogen and sulfur and which is optionally mono-, di- or tri-substituted on the ring with $Y_1$, $Y_2$ and/or $Y_3$;
(b) alternatively $R_1$ is —CH($R_5$)C(O)$W_1$ or a peptidyl substituent of the formula —(Xaa$_1$)$_n$W$_2$, wherein $R_5$ is hydrogen, alkyl of 1 to about 12 carbon atoms, cycloalkyl of 3 to about 12 carbon atoms, aryl of 5 to about 14 carbon atoms, or aralkyl of about 7 to about 15 carbon atoms, all optionally substituted with 1 to 3 substituents independently selected from hydroxy, sulfhydryl, alkylthio, carboxyl, amide, amino alkylamino, indolyl, 3-N-formylindolyl, benzyloxy, halobenzyloxy, guanidino, nitroguanidino or imidazolyl optionally substituted with alkoxyalkyl; $W_1$ and $W_2$ are independently selected from —OH, —O$Z_1$, —SH, —S$Z_1$, —NH$_2$, —NH$Z_1$ and —N$Z_1Z_2$; each Xaa$_1$ is an independently selected amino acid residue and n is an integer from 1 to 10; or
(c) alternatively $R_3$C(O)— is $W_1$CH($R_5$)C(O)— or $R_4$ wherein $R_4$ is a peptide substituent of the formula $Z_1$X(Xaa$_2$)$_r$— wherein each Xaa$_2$ is an independently selected amino acid residue, r is an integer from 1 to 10 and X is —C(O)—, —S(O)$_2$—, —OC(O)—, or a direct link;
(iii) each $Y_1$, $Y_2$ and $Y_3$ is independently selected from the group consisting of halogen, cyano, nitro, tetrazolyl, guanidino, amidino, methylguanidino, —CH$_3$, —CH$_2$CH$_3$, —CH$_2$CH$_2$CH$_3$, —CH(CH$_3$)$_2$, —CH$_2$CF$_3$, —CH(CF$_3$)$_2$, —OCF$_3$, —OCF$_2$H, —OCF$_2$CF$_3$, —OC(O)NH$_2$, —OC(O)NHZ$_1$, —OC(O)NZ$_1$Z$_2$, —NHC(O)Z$_1$, —NHC(O)NH$_2$, —NHC(O)NHZ$_1$, —NHC(O)NHZ$_1$Z$_2$, —C(O)OH, —C(O)OZ$_1$, —C(O)NH$_2$, —C(O)NHZ$_1$, —C(O)NZ$_1$Z$_2$, —P(O)$_3$H$_2$, —P(O)$_3$(Z$_1$)$_2$, —S(O)$_3$H, —S(O)$_m$Z$_1$, —Z$_1$, —OZ$_1$, —OH, —NH$_2$, —NHZ$_1$, —NZ$_1$Z$_2$, and —S(O)$_m$(CF$_2$)$_q$CF$_3$, wherein m is 0, 1 or 2, q is an integer from 0 to 5; and
(iv) each $Z_1$ and $Z_2$ is independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms; comprising the steps:
(a) reacting a protected amino-aldehyde of the formula PGNHCH($R_2$)CHO, an isonitrile of the formula $R_1$NC and a carboxy compound of the formula YCO$_2$H wherein Y is CF$_3$ or $R_3$ to give an aminoacyloxycarboxamide compound of formula (B):

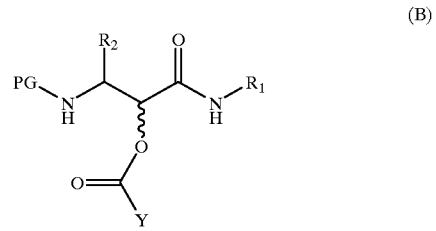

(B)

and
(b)
(i) where $R_x$ is PG, treating the amino acyloxycarboxamide intermediate from step (a) under acyloxy group removing conditions to give said compound of formula (A); or
(ii) where $R_x$—C(O)$R_3$, treating the amino acyloxycarboxamide intermediate from step (a) under PG group removing conditions which include a pH of about 6 to about 9 to give said compound of formula (A).

According to one preferred embodiment $R_x$ is PG. According to one aspect of this embodiment, Y is trifluoromethyl. Preferred acyloxy group removing conditions include extractive aqueous procedures. Such procedures preferably partition organic products and by-products between organic and aqueous phases to allow easy separation of a desired organic product from by-products. It is especially preferred to include a mild organic base in step (a). Suitable mild organic bases include pyridine and its alkyl derivatives. According to an alternate aspect of this embodiment, Y is $R_3$. Preferred acyloxy group removing conditions include selective hydrolysis with an alkali metal alkoxide.

According to an alternate preferred embodiment of this aspect of the invention, $R_x$ is —C(O)$R_3$. Suitable PG group removal conditions depend on the PG group and are summarized hereinbelow in the Detailed Description of the Invention.

Optionally, the methods of the invention may further comprise a step wherein the derivative of formula (A) is subjected to oxidation conditions so that the α-hydroxy group is oxidized to a carbonyl to give an α-ketoamide derivative of formula (C):

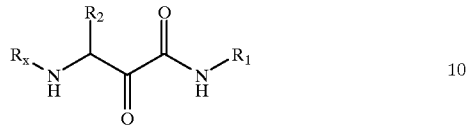

(C)

Suitable oxidizing conditions include use of EDC and DCA in DMSO and toluene, and those described hereinbelow in the Detailed Description of the Invention.

According to the present invention, a number of embodiments are provided. One group is directed to methods which employ trifluoroacetic acid ("TFA Methods") and another group is directed to methods which employ a carboxylic acid of formula $R_3COOH$ ("Complex Methods").

According to an aspect of the present invention which uses trifluoroacetic acid, provided are a group of embodiments termed herein "TFA Methods". Included within this group of embodiments is a method termed "TFA Method I" which is a method of preparing an α-hydroxyl-β-amino acid derivative comprising the steps of (a) contacting a blocked aminoaldehyde of the formula $PGNHCH(R_2)CHO$ with trifluoroacetic acid and an isoitrile compound of the formula $R_1NC$ in the presence of a mild organic base to give a transient amino acyloxy trifluoroacetate derivative; and (b) treating the amino acyloxy trifluoroacetate derivative of step (a) under acyloxy removing conditions to give an α-hydroxy-β-amino amide derivative of formula (TFA-I):

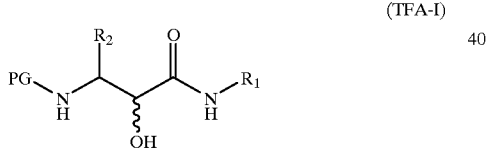

(TFA-I)

wherein:
(i) PG is a protecting group; and
(ii)
  (a) $R_1$ and $R_2$ are independently selected from the group consisting of alkyl of 1 to about 12 carbon atoms, cycloalkyl of 3 to about 12 carbon atoms, alkenyl of 2 to about 12 carbon atoms, cycloalkenyl of 5 to about 12 carbon atoms, and alkynyl 3 to about 12 carbon atoms, all optionally substituted with 1 to 3 substituents independently selected from $Y_1$, $Y_2$ and/or $Y_3$; aryl of about 5 to about 14 carbon atoms which is optionally mono-, di- or tri- substituted with $Y_1$, $Y_2$ and/or $Y_3$; heteroaryl of about 5 to about 14 ring atoms, with the ring atoms selected from carbon atoms and heteroatoms, wherein the heteroatoms are selected from oxygen, nitrogen and sulfur and which is optionally mono-, di-, tri- substituted with $Y_1$, $Y_2$ and/or $Y_3$; aralkyl of about 6 to about 18 carbon atoms which is optionally mono-, di- or tri- substituted on the aryl ring with $Y_1$, $Y_2$ and/or $Y_3$; and heteroaralkyl of about 5 to about 18 carbon atoms having about 5 to about 14 ring atoms with the ring atoms selected from carbon atoms and heteroatoms, wherein the heteroatoms are selected from oxygen, nitrogen and sulfur and which is optionally mono, di- or tri-substituted on the ring with $Y_1$, $Y_2$ and/or $Y_3$; or (b) alternatively $R_1$ is —$CH(R_5)C(O)W_1$, or a peptidyl substituent of the formula —$(Xaa_1)_nW_2$, wherein $R_5$ is hydrogen, alkyl of 1 to about 12 carbon atoms, cycloalkyl of 3 to about 12 carbon atoms, aryl of 5 to about 14 carbon atoms, or aralkyl of about 7 to about 15 carbon atoms, all optionally substituted with 1 to 3 substituents independently selected from hydroxy, sulfhydryl, alkylthio, carboxyl, amide, amino alkylamino, indolyl, 3-N-formylindolyl, benzyloxy, halobenzyloxy, guanidino, nitroguanidino or imidazolyl optionally substituted with alkoxyalkyl; $W_1$ and $W_2$ are independently selected from —OH, —$OZ_1$, —SH, —$SZ_1$, —$NH_2$, —$NHZ_1$ and —$NZ_1Z_2$; each $Xaa_1$ is an independently selected amino acid residue and n is an integer from 1 to 10;

(iii) each $Y_1$, $Y_2$ and $Y_3$ is independently selected from the group consisting of halogen, cyano, nitro, tetrazolyl, guanidino, amidino, methylguanidino, —$CH_3$, —$CH_2CH_3$, —$CH_2CH_2CH_3$, —$CH(CH_3)_2$, —$CH_2CF_3$, —$CH(CF_3)_2$, —$OCF_3H$, —$OCF_2CF_3$, —$OC(O)NH_2$, —$OC(O)NHZ_1$, —$OC(O)NZ_1Z_2$, —$NHC(O)Z_1$, —$NHC(O)NH_2$, —$NHC(O)NHZ_1$, —$NHC(O)NHZ_1Z_2$, —$C(O)OH$, —$C(O)OZ_1$, —$C(O)NH_2$, —$C(O)NHZ_1$, —$C(O)NZ_1Z_2$, —$P(O)_3H_2$, —$P(O)_3(Z_1)_2$, —$S(O)_3H$, —$S(O)_mZ_1$, —$Z_1$, —$OZ_1$, —OH, —$NH_2$, —$NHZ_1$, —$NZ_1Z_2$, and —$S(O)_m(CF_2)_qCF_3$, wherein m is 0, 1 or 2, q is an integer from 0 to 5; and (iv) and each $Z_1$ and $Z_2$ is independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms.

According to a further aspect is provided a method termed "TFA Method II" which further comprises (c) contacting the product (formula TFA-I) of step (b) of method TFA-1 with an acid reagent under hydrolytic conditions to give an α-hydroxy-β-amino acid of the formula (TFA-II)

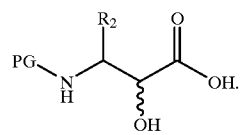

(TFA-II)

The present invention also provides a method termed "TFA Method III" which is a method of preparing an α-ketoamide derivative of formula (TFA-III):

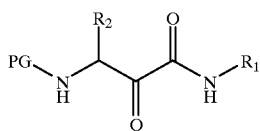

(TFA-III)

wherein
(i) PG is a protecting group; and
(ii)
(a) $R_1$ and $R_2$ are independently selected from the group consisting of alkyl of 1 to about 12 carbon atoms, cycloalkyl of 3 to about 12 carbon atoms, alkenyl of 2 to about 12 carbon atoms, cycloalkenyl of 5 to about 12 carbon atoms, and alkynyl 3 to about 12 carbon atoms, all optionally substituted with 1 to 3 substituents independently selected from $Y_1$, $Y_2$ and/or $Y_3$; aryl of about 5 to about 14 carbon atoms which is optionally mono-, di- or tri- substituted with $Y_1$, $Y_2$, and/or $Y_3$; heteroaryl of about 5 to about 14 ring atoms, with the ring atoms selected from carbon atoms and heteroatoms, wherein the heteroatoms are selected from oxygen, nitrogen and sulfur and which is optionally mono-, di-, tri- substituted with $Y_1$, $Y_2$ and/or $Y_3$; aralkyl of about 6 to about 18 carbon atoms which is optionally mono-, di- or tri- substituted on the aryl ring with $Y_1$, $Y_2$ and/or $Y_3$; and heteroaralkyl of about 5 to about 18 carbon atoms having about 5 to about 14 ring atoms with the ring atoms selected from carbon atoms and heteroatoms, wherein the heteroatoms are selected from oxygen, nitrogen and sulfur and which is optionally mono, di- or tri-substituted on the ring with $Y_1$, $Y_2$ and/or $Y_3$; or
(b) alternatively $R_1$ is —CH($R_5$)C(O)$W_1$, or a peptidyl substituent of the formula —(Xaa$_1$)$_n$W$_2$, wherein $R_5$ is hydrogen, alkyl of 1 to about 12 carbon atoms, cycloalkyl of 3 to about 12 carbon atoms, aryl of 5 to about 14 carbon atoms, or aralkyl of about 7 to about 15 carbon atoms, all optionally substituted with 1 to 3 substituents independently selected from hydroxy, sulfhydryl, alkylthio, carboxyl, amide, amino alkylamino, indolyl, 3—N-formylindolyl, benzyloxy, halobenzyloxy, guanidino, nitroguanidino or imidazolyl optionally substituted with alkoxyalkyl; $W_1$ and $W_2$ are independently selected from —OH, —OZ$_1$, —SH, —SZ$_1$, —NH$_2$, —NHZ$_1$ and —NZ$_1$Z$_2$; each Xaa$_1$ is an independently selected amino acid residue and n is an integer from 1 to 10;
(iii) each $Y_1$, $Y_2$ and $Y_3$ is independently selected from the group consisting of halogen, cyano, nitro, tetrazolyl, guanidino, amidino, methylguanidino, —CH$_3$, —CH$_2$CH$_3$, —CH$_2$CH$_2$CH$_3$, —CH (CH$_3$)$_2$, —CH$_2$CF$_3$, —CH(CF$_3$)$_2$, —OCF$_3$, —OCF$_2$H, —OCF$_2$CF$_3$, —OC(O)NH$_2$, —OC(O)NHZ$_1$, —OC(O)NZ$_1$Z$_2$, —NHC(O)Z$_1$, —NHC(O)NH$_2$, —NHC(O)NHZ$_1$, —NHC(O)NHZ$_1$Z$_2$, —C(O)OH, —C(O)OZ$_1$, —C(O)NH$_2$, —C(O)NHZ$_1$, —C(O)NZ$_1$Z$_2$, —P(O)$_3$H$_2$, —P(O)$_3$(Z$_1$)$_2$, —S(O)$_3$H, —S(O)$_m$Z$_1$, —Z$_1$, —OZ$_1$, —OH, —NH$_2$, —NHZ$_1$, —NZ$_1$Z$_2$, and —S(O)$_m$(CF$_2$)$_q$CF$_3$, wherein m is 0, 1 or 2, q is an integer from 0 to 5; and
(iv) and each $Z_1$ and $Z_2$ is independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms; comprising the steps of:

(a) contacting a blocked aminoaldehyde of the formula PGNHCG(R$_2$)CHO with trifluoroacetic acid and an isonitrile compound of the formula R$_1$NC in the presence of a mild organic base to give a transient amino acyloxy trifluoroacetate derivative;
(b) treating the amino acyloxy trifluoroacetate derivative of step (a) under acyloxy removing conditions or to give an α-hydroxy-β-amino amide derivative of formula (TFA-I); and
(c) treating the derivative from step (b) under oxidizing conditions to give an α-ketoamide derivative of formula (TFA-III).

According to an alternate aspect of the present invention, provided is TFA Method IV which is directed to a method of preparing a semicarbazone-protected ketoamide derivative of formula (TFA-IV):

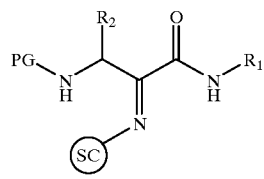

(TFA-IV)

wherein
(i) PG is a protecting group; and
(ii)
(a) $R_1$ and $R_2$ are independently selected from the group consisting of alkyl of 1 to about 12 carbon atoms, cycloalkyl of 3 to about 12 carbon atoms, alkenyl of 2 to about 12 carbon atoms, cycloalkenyl of 5 to about 12 carbon atoms, and alkynyl 3 to about 12 carbon atoms, all optionally substituted with 1 to 3 substituents independently selected from $Y_1$, $Y_2$ and/or $Y_3$; aryl of about 5 to about 14 carbon atoms which is optionally mono-, di- or tri- substituted with $Y_1$, $Y_2$, and/or $Y_3$; heteroaryl of about 5 to about 14 ring atoms, with the ring atoms selected from carbon atoms and heteroatoms, wherein the heteroatoms are selected from oxygen, nitrogen and sulfur and which is optionally mono-, di-, tri- substituted with $Y_1$, $Y_2$ and/or $Y_3$; aralkyl of about 6 to about 18 carbon atoms which is optionally mono-, di- or tri- substituted on the aryl ring with $Y_1$, $Y_2$ and/or $Y_3$; and heteroaralkyl of about 5 to about 18 carbon atoms having about 5 to about 14 ring atoms with the ring atoms selected from carbon atoms and heteroatoms, wherein the heteroatoms are selected from oxygen, nitrogen and sulfur and which is optionally mono, di- or tri-substituted on the ring with $Y_1$, $Y_2$ and/or $Y_3$; or
(b) alternatively $R_1$ is —CH($R_5$)C(O)$W_1$, or a peptidyl substituent of the formula —(Xaa$_1$)$_n$W$_2$, wherein $R_5$ is hydrogen, alkyl of 1 to about 12 carbon atoms, cycloalkyl of 3 to about 12 carbon atoms, aryl of 5 to about 14 carbon atoms, or aralkyl of about 7 to about 15 carbon atoms, all optionally substituted with 1 to 3 substituents independently selected from hydroxy, sulfhydryl, alkylthio, carboxyl, amide, amino alkylamino, indolyl, 3-N-formylindolyl, benzyloxy, halobenzyloxy, guanidino, nitroguanidino or imidazolyl optionally substituted with alkoxyalkyl; $W_1$ and $W_2$ are independently selected from —OH, —$OZ_1$, —SH, —$SZ_1$, —$NH_2$, —$NHZ_1$ and —$NZ_1Z_2$; each $Xaa_1$ is an independently selected amino acid residue and n is an integer from 1 to 10;

(iii) each $Y_1$, $Y_2$ and $Y_3$ is independently selected from the group consisting of halogen, cyano, nitro, tetrazolyl, guanidino, amidino, methylguanidino, —$CH_3$, —$CH_2CH_3$, —$CH_2CH_2CH_3$, —$CH(CH_3)_2$, —$CH_2CF_3$, —$CH(CF_3)_2$, —$OCF_3$, —$OCF_2H$, —$OCF_2CF_3$, —$OC(O)NH_2$, —$OC(O)NHZ_1$, —$OC(O)NZ_1Z_2$, —$NHC(O)Z_1$, —$NHC(O)NH_2$, —$NHC(O)NHZ_1$, —$NHC(O)NHZ_1Z_2$, —$C(O)OH$, —$C(O)OZ_1$, —$C(O)NH_2$, —$C(O)NHZ_1$, —$C(O)NZ_1Z_2$, —$P(O)_3H_2$, —$P(O)_3(Z_1)_2$, —$S(O)_3H$, —$S(O)_mZ_1$, —$Z_1$, $OZ_1$, —OH, —$NH_2$, —$NHZ_1$, —$NZ_1Z_2$, and —$S(O)_m(CF_2)_qCF_3$, wherein m is 0, 1 or 2, q is an integer from 0 to 5;

(iv) and each $Z_1$ and $Z_2$ is independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms; and (v) and —SC is a semicarbazone group of the formula —NHC(O)NHQ wherein Q is selected from the group consisting of hydrogen, alkyl of 1 to about 12 carbon atoms, alkenyl of 3 to about 12 carbon atoms, alkynyl of 3 to about 12 carbon atoms, aryl of 5 to about 18 carbon atoms, heteroaryl of 5 to about 14 ring atoms with the ring atoms selected from carbon atoms and heteroatoms, wherein the heteroatoms are selected from oxygen, nitrogen and sulfur, di-arylalkyl and tri-arylalkyl;

comprising the step of contacting a α-ketoamide derivative of formula (TFA-III)

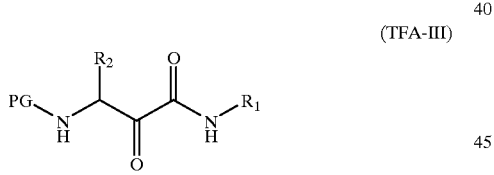

(TFA-III)

with a semicarbazide of the formula $NH_2NHC(O)NHQ$ under reactive conditions to give the semicarbazone derivative of formula (TFA-IV).

According to an aspect of the present invention termed "TFA Method V", provided is a method of preparing a peptidyl ketoamide of formula (TFA-V).

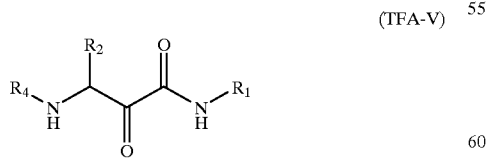

(TFA-V)

wherein (i)
(a) $R_1$ and $R_2$ are independently selected from the group consisting of alkyl of 1 to about 12 carbon atoms, cycloalkyl of 3 to about 12 carbon atoms, alkenyl of 2 to about 12 carbon atoms, cycloalkenyl of 5 to about 12 carbon atoms, and alkynyl 3 to about 12 carbon atoms, all optionally substituted with 1 to 3 substituents independently selected from $Y_1$, $Y_2$ and/or $Y_3$; aryl of about 5 to about 14 carbon atoms which is optionally mono-, di- or tri-substituted with $Y_1$, $Y_2$, and/or $Y_3$; heteroaryl of about 5 to about 14 ring atoms, with the ring atoms selected from carbon atoms and heteroatoms, wherein the heteroatoms are selected from oxygen, nitrogen and sulfur and which is optionally mono-, di-, tri-substituted with $Y_1$, $Y_2$ and/or $Y_3$; aralkyl of about 6 to about 18 carbon atoms which is optionally mono-, di- or tri-substituted on the aryl ring with $Y_1$, $Y_2$ and/or $Y_3$; and heteroaralkyl of about 5 to about 18 carbon atoms having about 5 to about 14 ring atoms with the ring atoms selected from carbon atoms and heteroatoms, wherein the heteroatoms are selected from oxygen, nitrogen and sulfur and which is optionally mono, di- or tri-substituted on the ring with $Y_1$, $Y_2$ and/or $Y_3$; or (b) alternatively $R_1$ is —$CH(R_5)C(O)W_1$, or a peptidyl substituent of the formula —$(Xaa_1)_nW_2$, wherein $R_5$ is hydrogen, alkyl of 1 to about 12 carbon atoms, cycloalkyl of 3 to about 12 carbon atoms, aryl of 5 to about 14 carbon atoms, or aralkyl of about 7 to about 15 carbon atoms, all optionally substituted with 1 to 3 substituents independently selected from hydroxy, sulfhydryl, alkylthio, carboxyl, amide, amino alkylamino, indolyl, 3—N-formylindolyl, benzyloxy, halobenzyloxy, guanidino, nitroguanidino or imidazolyl optionally substituted with alkoxyalkyl; $W_1$ and $W_2$ are independently selected from —OH, —$OZ_1$, —SH, —$SZ_1$, —$NH_2$, —$NHZ_1$ and —$NZ_1Z_2$; and each $Xaa_1$ is an independently selected amino acid residue and n is an integer from 1 to 10;

(iii) each $Y_1$, $Y_2$ and $Y_3$ is independently selected from the group consisting of halogen, cyano, nitro, tetrazolyl, guanidino, amidino, methylguanidino, —$CH_3$, —$CH_2CH_3$, —$CH_2CH_2CH_3$, —$CH(CH_3)_2$, —$CH_2CF_3$, —$CH(CF_3)_2$, —$OCF_3$, —$OCF_2H$, —$OCF_2CF_3$, —$OC(O)NH_2$, —$OC(O)NHZ_1$, —$OC(O)NZ_1Z_2$, —$NHC(O)Z_1$, —$NHC(O)NH_2$, —$NHC(O)NHZ_1$, —$NHC(O)NHZ_1Z_2$, —$C(O)OH$, —$C(O)OZ_1$, —$C(O)NH_2$, —$C(O)NHZ_1$, —$C(O)NZ_1Z_2$, —$P(O)_3H_2$, —$P(O)_3(Z_1)_2$, —$S(O)_3H$, —$S(O)_mZ_1$, —$Z_1$, —$OZ_1$, —OH, —$NH_2$, —$NHZ_1$, —$NZ_1Z_2$, and —$S(O)_m(CF_2)_qCF_3$, wherein m is 0, 1 or 2, q is an integer from 0 to 5, and each $Z_1$ and $Z_2$ is independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms; and (iv) $R_4$ is $Z_1$—X—$(Xaa_2)_r$— wherein X is —C(O)—, —S(O)—$_2$, —OC(O)— or a direct link, each $Xaa_2$ is an independently selected amino acid residue and r is an integer from 1 to 10; comprising the steps of:

(a) removing protecting group PG from a protected α-ketoamide derivative of formula (TFA-III)

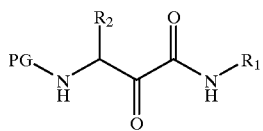

wherein PG is a protecting group: and (b) contacting the deprotected α-ketoamide derivative from step (a) with a compound of the formula $R_4$-LG, wherein LG is a leaving group, under coupling conditions to form an intermediate of the formula (TFA-V).

An alternate aspect of the present invention provides a group of embodiments of the present invention termed "Complex Methods". These Complex Methods employ a carboxylic acid of the formula $R_3COOH$.

Accordingly, a method termed "Complex Method I" is directed to a method of preparing an α-hydroxy-β-aminoamide derivative of the formula (CI)

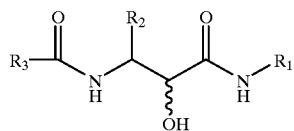

wherein (i)
  (a) $R_1$, $R_2$ and $R_3$ are independently selected from the group consisting of alkyl of 1 to about 12 carbon atoms, cycloalkyl of 3 to about 12 carbon atoms, alkenyl of 2 to about 12 carbon atoms, cycloalkenyl of 5 to about 12 carbon atoms, and alkynyl 3 to about 12 carbon atoms, all optionally substituted with 1 to 3 substituents independently selected from $Y_1$, $Y_2$ and/or $Y_3$; aryl of about 5 to about 14 carbon atoms which is optionally mono-, di- or tri-substituted with $Y_1$, $Y_2$, and/or $Y_3$; heteroaryl of about 5 to about 14 ring atoms, with the ring atoms selected from carbon atoms and heteroatoms, wherein the heteroatoms are selected from oxygen, nitrogen and sulfur and which is optionally mono-, di-, tri-substituted with $Y_1$, $Y_2$ and/or $Y_3$; aralkyl of about 6 to about 18 carbon atoms which is optionally mono-, di- or tri-substituted on the aryl ring with $Y_1$, $Y_2$ and/or $Y_3$; and heteroaralkyl of about 5 to about 18 carbon atoms having about 5 to about 14 ring atoms with the ring atoms selected from carbon atoms and heteroatoms, wherein the heteroatoms are selected from oxygen, nitrogen and sulfur and which is optionally mono-, di- or tri-substituted on the ring with $Y_1$, $Y_2$ and/or $Y_3$;

(b) alternatively $R_1$ is —CH($R_5$)C(O)$W_1$ or a peptidyl substituent of the formula —(Xaa$_1$)$_n$W$_2$, wherein $R_5$ is hydrogen, alkyl of 1 to about 12 carbon atoms, cycloalkyl of 3 to about 12 carbon atoms, aryl of 5 to about 14 carbon atoms, or aralkyl of about 7 to about 15 carbon atoms, all optionally substituted with 1 to 3 substituents independently selected from hydroxy, sulfhydryl, alkylthio, carboxyl, amide, amino alkylamino, indolyl, 3-N-formylindolyl, benzyloxy, halobenzyloxy, guanidino, nitroguanidino or imidazolyl optionally substituted with alkoxyalkyl; $W_1$ and $W_2$ are independently selected from —OH, —OZ$_1$, —SH, —SZ$_1$, —NH$_2$, —NHZ$_1$ and —NZ$_1$Z$_2$; each Xaa$_1$ is an independently selected amino acid residue and n is an integer from 1 to 10; or (c) alternatively $R_3C(O)$— is $W_1CH(R_5)C(O)$— or $R_4$ wherein $R_4$ is a peptide substituent of the formula $Z_1X(Xaa_2)_r$— wherein each Xaa$_2$ is an independently selected amino acid residue, r is an integer from 1 to 10 and X is —C(O)—, —S(O)$_2$—, —OC(O)—, or a direct link;

(ii) each $Y_1$, $Y_2$ and $Y_3$ is independently selected from the group consisting of halogen, cyano, nitro, tetrazolyl, guanidino, amidino, methylguanidino, —CH$_3$, —CH$_2$CH$_3$, —CH$_2$CH$_2$CH$_3$, —CH(CH$_3$)$_2$, —CH$_2$CF$_3$, —CH(CF$_3$)$_2$, —OCF$_3$, —OCF$_2$H, —OCF$_2$CF$_3$, —OC(O)NH$_2$, —OC(O)NHZ$_1$, —OC(O)NZ$_1$Z$_2$, —NHC(O)Z$_1$, —NHC(O)NH$_2$, —NHC(O)NHZ$_1$, —NHC(O)NHZ$_1$Z$_2$, —C(O)OH, —C(O)OZ$_1$, —C(O)NH$_2$, —C(O)NHZ$_1$, —C(O)NZ$_1$Z$_2$, —P(O)$_3$H$_2$, —P(O)$_3$(Z$_1$)$_2$, —S(O)$_3$H, —S(O)$_m$Z$_1$, —Z$_1$, —OZ$_1$, —OH, —NH$_2$, —NHZ$_1$, —NZ$_1$Z$_2$, and —S(O)$_m$(CF$_2$)$_q$CF$_3$, wherein m is 0, 1 or 2, q is an integer from 0 to 5; and (iii) each $Z_1$ and $Z_2$ is independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms; comprising the steps of:

(a) reacting an N-terminally blocked aminoaldehyde of the formula PGNHCH($R_2$)CHO, wherein PG is a protecting group, with an isonitrile of the formula $R_1NC$, and a carboxylic acid of the formula $R_3CO_2H$ in solvent to give an amino α-acyloxycarboxamide derivative of the formula

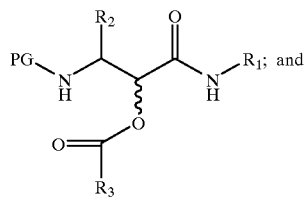

(b) removing protecting group PG from the amino α-acyloxycarboxamide derivative from step (a) under PG group removing conditions which include a pH of about 6 to about 9 thereby effecting acyl migration to give an α-hydroxy-β-aminoamide derivative of formula (CI).

According to a further aspect termed "Complex Method II", the present invention provides a method of preparing an α-ketoamide derivative of formula (CII)

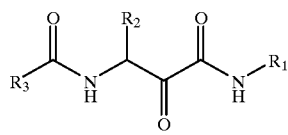

wherein (i)

(a) $R_1$, $R_2$ and $R_3$ are independently selected from the group consisting of alkyl of 1 to about 12 carbon atoms, cycloalkyl of 3 to about 12 carbon atoms, alkenyl of 2 to about 12 carbon atoms, cycloalkenyl of 5 to about 12 carbon atoms, and alkynyl 3 to about 12 carbon atoms, all optionally substituted with 1 to 3 substituents independently selected from $Y_1$, $Y_2$ and/or $Y_3$; aryl of about 5 to about 14 carbon atoms which is optionally mono-, di- or tri-substituted with $Y_1$, $Y_2$, and/or $Y_3$; heteroaryl of about 5 to about 14 ring atoms, with the ring atoms selected from carbon atoms and heteroatoms, wherein the heteroatoms are selected from oxygen, nitrogen and sulfur and which is optionally mono-, di-, tri-substituted with $Y_1$, $Y_2$ and/or $Y_3$; aralkyl of about 6 to about 18 carbon atoms which is optionally mono-, di- or tri-substituted on the aryl ring with $Y_1$, $Y_2$ and/or $Y_3$; and heteroaralkyl of about 5 to about 18 carbon atoms having about 5 to about 14 ring atoms with the ring atoms selected from carbon atoms and heteroatoms, wherein the heteroatoms are selected from oxygen, nitrogen and sulfur and which is optionally mono, di- or tri-substituted on the ring with $Y_1$, $Y_2$ and/or $Y_3$;

(b) alternatively $R_1$ is —$CH(R_5)C(O)W_1$ or a peptidyl substituent of the formula —$(Xaa_1)_n W_2$, wherein $R_5$ is hydrogen, alkyl of 1 to about 12 carbon atoms, cycloalkyl of 3 to about 12 carbon atoms, aryl of 5 to about 14 carbon atoms, or aralkyl of about 7 to about 15 carbon atoms, all optionally substituted with 1 to 3 substituents independently selected from hydroxy, sulfhydryl, alkylthio, carboxyl, amide, amino alkylamino, indolyl, 3-N-formylindolyl, benzyloxy, halobenzyloxy, guanidino, nitroguanidino or imidazolyl optionally substituted with alkoxyalkyl; $W_1$ and $W_2$ are independently selected from —OH, —$OZ_1$, —SH, —$SZ_1$, —$NH_2$, —$NHZ_1$ and —$NZ_1Z_2$; each $Xaa_1$ is an independently selected amino acid residue and n is an integer from 1 to 10; or (c) alternatively $R_3C(O)$— is $W_1CH(R_5)C(O)$— or $R_4$ wherein $R_4$ is a peptide substituent of the formula $Z_1X(Xaa_2)_r$— wherein each $Xaa_2$ is an independently selected amino acid residue, r is an integer from 1 to 10 and X is —$C(O)$—, —$S(O)_2$—, —$OC(O)$—, or a direct link;

(ii) each $Y_1$, $Y_2$ and $Y_3$ is independently selected from the group consisting of halogen, cyano, nitro, tetrazolyl, guanidino, amidino, methylguanidino, —$CH_3$, —$CH_2CH_3$, —$CH_2CH_2CH_3$, —$CH(CH_3)_2$, —$CH_2CF_3$, —$CH(CF_3)_2$—$OCF_3$, —$OCF_2H$, —$OCF_2CF_3$, —$OC(O)NH_2$, —$OC(O)NHZ_1$, —$OC(O)NZ_1Z_2$, —$NHC(O)Z_1$, —$NHC(O)NH_2$, —$NHC(O)NHZ_1$, —$NHC(O)NHZ_1Z_2$, —$C(O)OH$, —$C(O)OZ_1$, —$C(O)NH_2$, —$C(O)NHZ_1$, —$C(O)NZ_1Z_2$, —$P(O)_3H_2$, —$P(O)_3(Z_1)_2$, —$S(O)_3H$, —$S(O)_mZ_1$, —$Z_1$, —$Z_1$, —OH, —$NH_2$, —$NHZ_1$, —$NZ_1Z_2$, and —$S(O)_m(CF_2)_qCF_3$, wherein m is 0, 1 or 2, q is an integer from 0 to 5; and (iii) each $Z_1$ and $Z_2$ is independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms; comprising the steps of:

(a) reacting an N-terminally blocked aminoaldehyde of the formula $PGNHCH(R_2)CHO$, wherein PG is a protecting group, with an isonitrile of the formula $R_1NC$, and a carboxylic acid of the formula $R_3CO_2H$ in solvent to give an amino α-acyloxycarboxamide derivative of the formula (CIA)

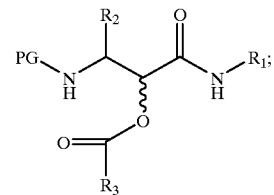

(b) removing protecting group PG from the amino α-acyloxycarboxamide derivative from step (a) under PG group removing conditions which include a pH of about 6 to about 9 thereby effecting acyl migration to give an α-hydroxy-β-aminoamide derivative of formula (CI); and (c) treating the derivative of formula (CI) from step (b) under oxidizing conditions to give an α-ketoamide derivative of formula (CII).

Another further aspect of the present invention is termed "Complex Method III" and provides a method of preparing a semi-carbazone protected ketoamide derivative of formula (CIII) using an α-ketoamide of formula (CII). Accordingly, Complex Method III is directed to a method of preparing a semi-carbazone protected ketoamide derivative of formula (CIII):

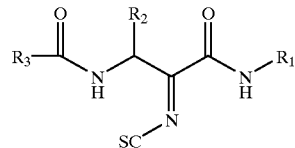

wherein (i)
(a) $R_1$, $R_2$ and $R_3$ are independently selected from the group consisting of alkyl of 1 to about 12 carbon atoms, cycloalkyl of 3 to about 12 carbon atoms, alkenyl of 2 to about 12 carbon atoms, cycloalkenyl of 5 to about 12 carbon atoms, and alkynyl 3 to about 12 carbon atoms, all optionally substituted with 1 to 3 substituents independently selected from $Y_1$, $Y_2$ and/or $Y_3$; aryl of about 5 to about 14 carbon atoms which is optionally mono-, di- or tri-substituted with $Y_1$, $Y_2$, and/or $Y_3$; heteroaryl of about 5 to about 14 ring atoms, with the ring atoms selected from carbon atoms and heteroatoms, wherein the heteroatoms are selected from oxygen, nitrogen and sulfur and which is optionally mono-, di-, tri-substituted with $Y_1$, $Y_2$ and/or $Y_3$; aralkyl of about 6 to about 18 carbon atoms which is optionally mono-, di- or tri-substituted on the aryl ring with $Y_1$, $Y_2$ and/or $Y_3$; and heteroaralkyl of about 5 to about 18 carbon atoms having about 5 to about 14 ring atoms with the ring atoms selected from carbon atoms and heteroatoms, wherein the heteroatoms are selected from oxygen, nitrogen and sulfur and which is optionally mono, di- or tri-substituted on the ring with $Y_1$, $Y_2$ and/or $Y_3$;

(b) alternatively $R_1$ is —$CH(R_5)C(O)W_1$ or a peptidyl substituent of the formula —$(Xaa_1)_n W_2$, wherein $R_5$ is hydrogen, alkyl of 1 to about 12 carbon atoms, cycloalkyl of 3 to about 12 carbon atoms, aryl of 5 to about 14 carbon atoms, or aralkyl of about 7 to about 15 carbon atoms, all optionally substituted with 1 to 3 substituents independently selected from hydroxy, sulfhydryl, alkylthio, carboxyl, amide, amino alkylamino, indolyl, 3-N-formylindolyl, benzyloxy, halobenzyloxy, guanidino, nitroguanidino or imidazolyl optionally substituted with alkoxyalkyl; $W_1$ and $W_2$ are independently selected from —OH, —$OZ_1$, —SH, —$SZ_1$, —$NH_2$, —$NHZ_1$ and —$NZ_1Z_2$; each $Xaa_1$ is an independently selected amino acid residue and n is an integer from 1 to 10; or (c) alternatively $R_3C(O)$— is $W_1CH(R_5)C(O)$— or $R_4$ wherein $R_4$ is a peptide substituent of the formula $Z_1X(Xaa_2)_r$— wherein each $Xaa_2$ is an independently selected amino acid residue, r is an integer from 1 to 10 and X is —C(O)—, —$S(O)_2$—, —OC(O)—, or a direct link;

(ii) each $Y_1$, $Y_2$ and $Y_3$ is independently selected from the group consisting of halogen, cyano, nitro, tetrazolyl, guanidino, amidino, methylguanidino, —$CH_3$, —$CH_2CH_3$, —$CH_2CH_2CH_3$, —$CH(CH_3)_2$, —$CH_2CF_3$, —$CH(CF_3)_2$, —$OCF_3$, —$OCF_2H$, —$OCF_2CF_3$, —$OC(O)NH_2$, —$OC(O)NHZ_1$, —$OC(O)NZ_1Z_2$, —$NHC(O)Z_1$, —$NHC(O)NH_2$, —$NHC(O)NHZ_1$, —$NHC(O)NHZ_1Z_2$, —C(O)OH, —$C(O)OZ_1$, —$C(O)NH_2$, —$C(O)NHZ_1$, —$C(O)NZ_1Z_2$, —$P(O)_3H_2$, —$P(O)_3(Z_1)_2$, —$S(O)_3H$, —$S(O)_mZ_1$, —$Z_1$, —$Z_1$, $OZ_1$, —OH, —$NH_2$, —$NHZ_1$, —$NZ_1Z_2$, and —$S(O)_m(CF_2)_qCF_3$, wherein m is 0, 1 or 2, q is an integer from 0 to 5;

(iii) each $Z_1$ and $Z_2$ is independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms; and (iv) SC is —NHCONHQ wherein Q is selected from the group consisting of hydrogen, alkyl of 1 to about 12 carbon atoms, alkenyl of 2 to about 12 carbon atoms, alkynyl of 3 to about 12 carbon atoms, aryl of 5 to about 18 carbon atoms, heteroaryl of 5 to about 18 ring atoms with the ring atoms selected from carbon atoms and heteroatoms wherein the heteroatoms are selected from oxygen, nitrogen and sulfur, aralkyl, di-arylalkyl and tri-arylalkyl; which comprises treating a compound of formula (CII) prepared by Complex Method II with a semicarbazide of the formula $NH_2NHCONHQ$ under conditions permitting formation of a semicarbazone-protected ketoamide derivative of formula (CIII).

An alternate aspect of the present invention termed "Complex Method IV", provides a method of preparing a peptidyl ketoamide of formula (CIV):

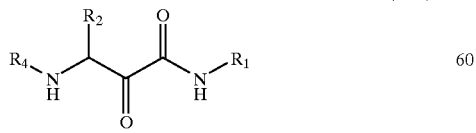

(CIV)

wherein
(i) $R_1$ is —$CH(R_5)C(O)W_1$ or a peptidyl substituent of the formula —$(Xaa_1)_nW_2$, wherein $R_5$ is hydrogen, alkyl of 1 to about 12 carbon atoms, cycloalkyl of 3 to about 12 carbon atoms, aryl of 5 to about 14 carbon atoms, or aralkyl of about 7 to about 15 carbon atoms, all optionally substituted with 1 to 3 substituents independently selected from hydroxy, sulfhydryl, alkylthio, carboxyl, amide, amino alkylamino, indolyl, 3-N-formylindolyl, benzyloxy, halobenzyloxy, guanidino, nitroguanidino or imidazolyl optionally substituted with alkoxyalkyl; $W_1$ and $W_2$ are independently selected from —OH, —$OZ_1$, —SH, —$SZ_1$, —$NH_2$, —$NHZ_1$ and —$NZ_1Z_2$; each $Xaa_1$ is an independently selected amino acid residue and n is an integer from 1 to 10;

(ii) $R_2$ is independently selected from the group consisting of alkyl of 1 to about 12 carbon atoms, cycloalkyl of 3 to about 12 carbon atoms, alkenyl of 2 to about 12 carbon atoms, cycloalkenyl of 5 to about 12 carbon atoms, and alkynyl 3 to about 12 carbon atoms, all optionally substituted with 1 to 3 substituents independently selected from $Y_1$, $Y_2$ and/or $Y_3$; aryl of about 5 to about 14 carbon atoms which is optionally mono-, di- or tri-substituted with $Y_1$, $Y_2$, and/or $Y_3$; heteroaryl of about 5 to about 14 ring atoms, with the ring atoms selected from carbon atoms and heteroatoms, wherein the heteroatoms are selected from oxygen, nitrogen and sulfur and which is optionally mono-, di-, tri-substituted with $Y_1$, $Y_2$ and/or $Y_3$; aralkyl of about 6 to about 18 carbon atoms which is optionally mono-, di- or tri-substituted on the aryl ring with $Y_1$, $Y_2$ and/or $Y_3$; and heteroaralkyl of about 5 to about 18 carbon atoms having about 5 to about 14 ring atoms with the ring atoms selected from carbon atoms and heteroatoms, wherein the heteroatoms are selected from oxygen, nitrogen and sulfur and which is optionally mono, di- or tri-substituted on the ring with $Y_1$, $Y_2$ and/or $Y_3$;

(iii) $R_4$ is a peptidyl substituent of the formula $Z_1X(Xaa_2)_r$— wherein each $Xaa_2$ is an independently selected amino acid residue, r is an integer from 1 to 10 and X is —C(O)—, —$S(O)_2$—, —OC(O)—, or a direct link;

(iv) each $Y_1$, $Y_2$ and $Y_3$ is independently selected from the group consisting of halogen, cyano, nitro, tetrazolyl, guanidino, amidino, methylguanidino, —$CH_3$, —$CH_2CH_3$, —$CH_2CH_2CH_3$, —$CH(CH_3)_2$, —$CH_2CF_3$, —$CH(CF_3)_2$, —$OCF_3$, —$OCF_2H$, —$OCF_2CF_3$, —$OC(O)NH_2$, —$OC(O)NHZ_1$, —$OC(O)NZ_1Z_2$, —$NHC(O)Z_1$, —$NHC(O)NH_2$, —$NHC(O)NHZ_1$, —$NHC(O)NHZ_1Z_2$, —C(O)OH, —$C(O)OZ_1$, —$C(O)NH_2$, —$C(O)NHZ_1$, —$C(O)NZ_1Z_2$, —$P(O)_3H_2$, —$P(O)_3(Z_1)_2$, —$S(O)_3H$, —$S(O)_mZ_1$, —$Z_1$, —$OZ_1$, —OH, —$NH_2$, —$NHZ_1$, —$NZ_1Z_2$, N-morpholino, —$S(CF_2)_qCF_3$, and —$S(O)_m(CF_2)_qCF_3$, wherein m is 0, 1 or 2, q is an integer from 0 to 5; and (v) each $Z_1$ and $Z_2$ is independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms; comprising steps of:

(a) reacting an N-terminally blocked aminoaldehyde of the formula $PGNHCH(R_2)CHO$, where PG is a protecting group, with an isonitrite of the formula $R_1NC$ and a peptidyl carboxylic acid of the formula $R_4OH$ in solvent to give a β-amino α-acyloxycarboxamide derivative of the formula:

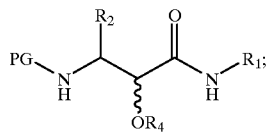

(b) removing protecting PG from the β-amino α-acyloxycarboxamide derivative from step (a) under PG removing conditions which include a pH of about 6 to about 9 to give an α-hydroxy-β-aminoamide derivative of the formula

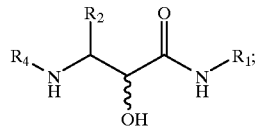

and (c) treating the α-hydroxy-β-aminoamide derivative from step (b) under oxidizing conditions to give a peptidyl ketoamide derivative of formula (CIV).

An additional aspect of the present invention termed "Complex Method V" provides a method of preparing an α-hydroxyl-β-protected aminoamide derivative of formula (CV):

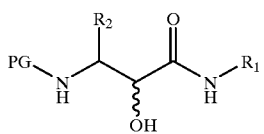

(CV)

comprising the steps of:

(a) reacting an N-terminally blocked aminoaldehyde of the formula PGNHCH($R_2$)CHO, an isonitrile of the formula $R_1$NC, and a carboxylic acid of the formula $R_3CO_2H$ in solvent to give an amino α-acyloxycarboxamide of the formula:

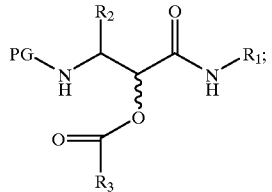

and (b) treating the amino α-acyloxycarboxamide derivative and selective hydrolysis conditions to hydrolyze the α-acyloxy group to a α-hydroxy β-protected aminoamide derivative of formula (CV), wherein (i) PG is a protecting group; and (ii)

(a) $R_1$, $R_2$ and $R_3$ are independently selected from the group consisting of alkyl of 1 to about 12 carbon atoms, cycloalkyl of 3 to about 12 carbon atoms, alkenyl of 2 to about 12 carbon atoms, cycloalkenyl of 5 to about 12 carbon atoms, and alkynyl 3 to about 12 carbon atoms, all optionally substituted with 1 to 3 substituents independently selected from $Y_1$, $Y_2$ and/or $Y_3$; aryl of about 5 to about 14 carbon atoms which is optionally mono-, di- or tri-substituted with $Y_1$, $Y_2$, and/or $Y_3$; heteroaryl of about 5 to about 14 ring atoms, with the ring atoms selected from carbon atoms and heteroatoms, wherein the heteroatoms are selected from oxygen, nitrogen and sulfur and which is optionally mono-, di-, tri-substituted with $Y_1$, $Y_2$ and/or $Y_3$; aralkyl of about 6 to about 18 carbon atoms which is optionally mono-, di- or tri-substituted on the aryl ring with $Y_1$, $Y_2$ and/or $Y_3$; and heteroaralkyl of about 5 to about 18 carbon atoms having about 5 to about 14 ring atoms with the ring atoms selected from carbon atoms and heteroatoms, wherein the heteroatoms are selected from oxygen, nitrogen and sulfur and which is optionally mono-, di- or tri-substituted on the ring with $Y_1$, $Y_2$ and/or $Y_3$;

(b) alternatively $R_1$ is —CH($R_5$)C(O)$W_1$ or a peptidyl substituent of the formula —(Xaa$_1$)$_n$W$_2$, wherein $R_5$ is hydrogen, alkyl of 1 to about 12 carbon atoms, cycloalkyl of 3 to about 12 carbon atoms, aryl of 5 to about 14 carbon atoms, or aralkyl of about 7 to about 15 carbon atoms, all optionally substituted with 1 to 3 substituents independently selected from hydroxy, sulfhydryl, alkylthio, carboxyl, amide, amino alkylamino, indolyl, 3-N-formylindolyl, benzyloxy, halobenzyloxy, guanidino, nitroguanidino or imidazolyl optionally substituted with alkoxyalkyl; $W_1$ and $W_2$ are independently selected from —OH, —O$Z_1$, —SH, —S$Z_1$, —NH$_2$, —NH$Z_1$ and —N$Z_1Z_2$; each Xaa$_1$ is an independently selected amino acid residue and n is an integer from 1 to 10; or (c) alternatively $R_3$C(O)— is $W_1$CH($R_5$)C(O)— or $R_4$ wherein $R_4$ is a peptide substituent of the formula $Z_1$X(Xaa$_2$)$_r$— wherein each Xaa$_2$ is an independently selected amino acid residue, r is an integer from 1 to 10 and X is —C(O)—, —S(O)$_2$—, —OC(O)—, or a direct link;

(iii) each $Y_1$, $Y_2$ and $Y_3$ is independently selected from the group consisting of halogen, cyano, nitro, tetrazolyl, guanidino, amidino, methylguanidino, —CH$_3$, —CH$_2$CH$_3$, —CH$_2$CH$_2$CH$_3$, —CH(CH$_3$)$_2$, —CH$_2$CF$_3$, —CH(CF$_3$)$_2$, —OCF$_3$, —OCF$_2$H, —OCF$_2$CF$_3$, —OC(O)NH$_2$, —OC(O)NH$Z_1$, —OC(O)N$Z_1Z_2$, —NHC(O)$Z_1$, —NHC(O)NH$_2$, —NHC(O)NH$Z_1$, —NHC(O)NH$Z_1Z_2$, —C(O)OH, —C(O)O$Z_1$, —C(O)NH$_2$, —C(O)NH$Z_1$, —C(O)N$Z_1Z_2$, —P(O)$_3$H$_2$, —P(O)$_3$($Z_1$)$_2$, —S(O)$_3$H, —S(O)$_m$$Z_1$, —$Z_1$, —O$Z_1$, —OH, —NH$_2$, —NH$Z_1$, —N$Z_1Z_2$, N-morpholino, —S(CF$_2$)$_q$CF$_3$, and —S(O)$_m$(CF$_2$)$_q$CF$_3$, wherein m is 0, 1 or 2, q is an integer from 0 to 5; and (iv) each $Z_1$ and $Z_2$ is independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms.

Preferred selective hydrolysis conditions used for Complex Method V include an alkali metal alkoxide.

The present invention is also directed to certain novel α-hydroxy-β-amino acid and amide derivatives and α-ketoamide derivatives prepared by the Methods described herein.

Definitions

In accordance with the present invention and as used herein, the following terms are defined to have the following meanings unless explicitly stated otherwise.

"Acyl migration" or "acyl shift" refers to the movement or transfer of an acyl moiety, i.e., R(CO)—, from one molecular position to another. In the context of this invention, acyl movement is usually from an oxygen atom to a nitrogen atom.

"Alkali metal alkoxide" refers to a basic reagent of the general formula MOR, where M is an alkali metal cation such as Li, Na, or K and typically R is methyl, ethyl, isopropyl or another simple lower alkyl group.

The term "alkenyl" refers to unsaturated aliphatic groups having at least one double bond.

The term "alkyl" refers to saturated aliphatic groups including straight-chain, branched-chain and cyclic (including polycyclic) groups.

The terms "alkoxy" and "alkoxyl" refer to a group having the formula, R—O—, wherein R is an alkyl group.

The term "alkoxycarbonyl" refers to —C(O)OR wherein R is alkyl.

The term "aralkenyl" refers to an alkenyl group substituted with an aryl group.

The term "aralkyl" refers to an alkyl group substituted with an aryl group. Suitable aralkyl groups include benzyl, phenethyl, and the like, all of which may be optionally substituted.

The term "aryl" refers to an aromatic group which has at least one ring having a conjugated pi electron system and includes a carbocyclic aryl, heterocyclic aryl and biarylgroups, all of which may be optionally substituted.

The term "aryloxy" refers to a group having the formula, R—O—, wherein R is an aryl group.

The term "aralkoxy" refers to a group having the formula, R—O—, wherein R is an aralkyl group.

The term "amino acid" refers to both natural, unnatural amino acids in their D and L stereo isomers if their structures allow such stereoisomeric forms, and their analogs. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr) and valine (Val). Unnatural amino acids include, but are not limited to azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4 diaminoisobutyric acid, demosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, N-methylvaline, norvaline, norleucine, ornithine and pipecolic acid. Amino acid analogs include the natural and unnatural amino acids which are chemically blocked, reversibly or irreversibly, or modified on their N-terminal amino group or their side-chain groups, as for example, methionine sulfoxide, methionine sulfone, S-(carboxymethyl)-cysteine, S-(carboxymethyl)-cysteine sulfoxide and S-(carboxymethyl)-cysteine sulfone.

The term "amino acid analog" refers to an amino acid wherein either the C-terminal carboxy group, the N-terminal amino group or side-chain functional group has been chemically modified to another functional group. For example, aspartic acid-(beta-methyl ester) is an amino acid analog of aspartic acid; N-ethylglycine is an amino acid analog of glycine; or alanine carboxamide is an amino acid analog of alanine.

The term "amino acid residue" refers to radicals having the structure: (1) —C(O)—R—NH—, wherein R typically is —CH(R')—, wherein R' is H or a carbon containing substituent;

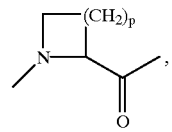

wherein p is 1, 2 or 3 representing the azetidinecarboxylic acid, proline or pipecolic acid residues, respectively.

"Biaryl" refers to phenyl substituted by carbocyclic or heterocyclic aryl as defined herein, ortho, meta or para to the point of attachment of the phenyl ring.

"Brine" refers to an aqueous saturated solution of sodium chloride.

"Carbocyclic aryl" refers to aromatic groups wherein the ring atoms on the aromatic ring are carbon atoms. Carbocyclic aryl groups include monocyclic carbocyclic aryl groups and naphthyl groups, all of which may be optionally substituted. Suitable carbocyclic aryl groups include phenyl and naphthyl. Suitable substituted carbocyclic aryl groups include indene and phenyl substituted by one to two substituents such being advantageously lower alkyl, hydroxy, lower alkoxy, lower alkoxycarbonyl, halogen, trifluoromethyl, difluoromethyl, nitro, and cyano. Substituted naphthyl refers to naphthyl, more preferably 1- or 2-naphthyl, substituted by 1 to 3 independently selected substituents.

"Cycloalkenyl" refers to a cyclic alkenyl group. Suitable cycloalkenyl groups include, for example, cyclopentenyl and cyclohexenyl.

"Cycloalkyl" refers to a cyclic alkyl group having at least one ring and includes polycyclic groups, including fused ring cyclic alkyl groups. Suitable cycloalkyl groups include, for example, cyclohexyl, cyclopropyl, cyclopentyl, and cycloheptyl.

"Cyclohexylmethyl" refers to a cyclohexyl group attached to $CH_2$.

"Fused carbocyclic" refers to a multicyclic fused carbocyclic ring having both aromatic and non-aromatic rings. Suitable fused carbocyclic rings include fluorenyl, tetralin and the like.

"Fused carbocyclic alkyl" refers to an alkyl group substituted with a fused carbocyclic ring moiety, preferably a multicyclic fused carbocyclic ring including both aromatic and non-aromatic rings. Suitable fused carbocyclic alkyl groups include fluorenylmethyl, and the like.

The term "halogen" refers to fluorine, chlorine, bromine and iodine.

"Heteroaralkenyl" refers to an alkenyl group substituted with a heteroaryl, and includes those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems. Preferably the alkenyl group has from 2 to about 6 carbon atoms.

"Heteroaralkyl" refers to an alkyl group substituted with a heteroaryl, such as picolyl, and includes those heterocyclic systems described in "Handbook of Chemistry and Physics", 49th edition, 1968, R. C. Weast, editor; The Chemical Rubber Co., Cleveland, OH. See particularly Section C, Rules for Naming Organic Compounds, B. Fundamental Heterocyclic Systems. Preferably the alkyl group has from 1 to about 6 carbon atoms.

"Heteroaryl" refers to aryl groups having from 1 to 9 carbon atoms and the remainder of the ring atoms are heteroatoms, and includes those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems. Suitable heteroatoms include oxygen, nitrogen, and S(O)i, wherein i is 0, 1 or 2, and suitable heterocyclic aryls include furanyl, thienyl, pyridyl, pyrrolyl, pyrimidyl, pyrazinyl, imidazolyl, and the like.

"Heterocyclo" refers to a reduced heterocyclic ring system comprised of carbon, nitrogen, oxygen and/or sulfur atoms, and includes those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems.

"Heterocycloalkyl" refers to an alkyl group substituted with a heterocyclo group, and includes those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems. Preferably the alkyl group has from about 1 to about 6 carbon atoms.

The term "lower" referred to herein in connection with organic radicals or groups defines such radicals or groups with one and up to and including 5 carbon atoms, preferably up to and including 4 carbon atoms, and advantageously one or two carbon atoms. Such radicals or groups may be straight chain or branched chain.

"Perfluoroalkyl" refers to an alkyl group which has every hydrogen replaced with fluorine.

"Perfluoroalkyl" refers to an aryl group which has every hydrogen replaced with fluorine.

"Perfluoroarylalkyl" refers to an aralkyl group in which every hydrogen on the aryl moiety is replaced with fluorine.

"Pharmaceutically acceptable salt" includes salts of the compounds of the present invention derived from the combination of such compounds and an organic or inorganic acid. In practice the use of the salt form amounts to use of the base form. The compounds of the present invention are useful in both free base and salt form, with both forms being considered as being within the scope of the present invention.

"Aspartyl protease refers to a class of proteolytic enzymes which contain and utilize a $P_1$-aspartic acid residue for a catalytic action, and as example refers to enzymes such as renin and HIV protease.

"α-Aminoaldehyde" refers to a reactive organic species of the general formula $H_2NC(R)(R')CHO$, where R and R' can be H, alkyl, etc.

"α-Dicarbonyl compound" refers to a reactive organic species containing two contiguous carbonyl groups of the general formula $R(CO)(CO)R'$, where R and R' can encompass the same or different substituents.

"α-Hydroxy-β-aminocarboxylic acid" refers to a functionalized carboxylic acid derivative of the general formula $H_2NC(R)(R')C(R'')(OH)CO_2H$, where R, R' and R" represent the same or different substituents.

"a-Ketocarboxylic" refers to a reactive, labile organic residue of the general formula $R(CO)CO_2R'$, where R and R' represent the same or different substituents, preferably not hydrogen. A ketocarboxylic acid is represented by a compound where R' is H. "Calpain", an acronym for calcium-activated neutral protease, refers to an important member of the cysteine protease enzyme family which has been implicated in a variety of important disease states, including osteoporosis and cancer, neurodegeneration, stroke, Alzheimer's disease, muscular dystrophy, platelet aggregation and inflammation.

"Carboxamide" refers to an organic functional group of the general formula RCON (R) (R'), where R and R' represent the same or different substituents.

"Extractive aqueous procedures" refer to procedures conventionally used in the chemical synthesis arts, including solution phase chemistry, which partition organic products and by-products between organic and aqueous phases to allow separation of a desired organic product from by-products.

"HIV" refers to Human Immunodeficiency Virus.

The terms "hydrolysis" and "selective hydrolysis" refer to a cleavage reaction involving the addition of a molecule of water to an organic substrate.

"Hydrolytic work up" refers to an aqueous extractive workup process which causes the hydrolysis of a functionality in an organic molecule.

"Inert organic solvent" refers to an unreactive solvent.

"Isonitrile" or "isocyanide" refer to a reactive functional group of the general formula R—NC, where R represents an alkyl, aryl or other hydrocarbyl substituent.

"Ketoamide" refers to the group —C(=O)—C(=O)—N—.

"LG" refers to a leaving group.

"Mild organic base" refers to a non-nucleophilic hindered organic base.

"Norstatine" refers to an α-hydroxy-β-amino acid derivative of the general formula $H_2NCH(R)CH(OH)CO_2H$ where R is an alkyl, aryl or other hydrocarbyl substituent.

"Oxidation" in the context of this invention, refers to a chemical process which essentially removes two electrons from the carbon atom from the species of formula —CH(OH)— to produce a product of the formula —(C=O)—. Formally, a change in the oxidation state of the carbon has increased, and the substrate has lost two hydrogen atoms.

"Peptide" refers to a compound having two or more amino acids linked to each other by amide bonds. Typically, peptides have up to about thirty amino acids.

"Peptidomimetic" or "peptide mimic" refers to a synthetic organic molecule which resembles or mimics the structure of a peptide.

"PG" refers to a protecting group.

The terms "protected" and "reprotecting" refer to the presence or addition of a protecting group, viz, the process of temporarily protecting or inactivating a normally reactive functional group so as to allow for conductance of chemical reactions in other parts of a molecule.

"Semicarbazone" refers to a derivative formed by the reaction of a semicarbazide with an aldehyde or ketone of the general formula $R_1(R_2)C=NNH(CO)NHRR'$, where $R_1$, $R_2$, R, and R' can represent H, alkyl, aryl and other common organic groups.

"Semicarbazide" refers to a fundamental reagent of the formula $H_2NNH(CO)NH_2$ or $H_2NNH(CO)NRR'$ which is known to react with a variety of electrophilic carbonyl compounds such as aldehydes and ketones. R and R' can represent H, alkyl, or other typical organic groups.

"Ac" refers to acetyl.

"Acm" refers to acetamidomethyl.

"Alloc" refers to allyloxycarbonyl.

"BH$_3$.THF" refers to borane-tetrahydrofuran complex, a common reducing or hydroborating reagent.

"Boc" refers to tert-butoxycarbonyl.

"(Boc)$_2$O refers to di-tert-butyl dicarbonate.

"Bom" refers to benzyloxymethyl.

"Bz" refers to benzoyl.

"Cbz" refers to benzyloxycarbonyl or carbobenzyloxy.

"CHO" refers to a formyl group.

"2-ClZ" refers to 2-chlorobenzyloxycarbonyl.

"DCA" or "DCAA" refers to dichloroacetic acid.

"DCC" refers to N,N'-dicyclohexylcarbodiimide.

"DCM" refers to dichloromethane.

"DIBALH" or "(i-Bu)$_2$AlH" refers to diisobutyl aluminum hydride.

"DIEA" or "DIPEA" refers to N,N-diisopropylethylamine.

"DMF" refers to N,N-dimethylformamide.

"DMSO" refers to dimethylsulfoxide.

"Dnp" refers to 2,4-dinitrophenyl-.

"dPsc" refers to diphenylmethyl semicarbazone protecting group.

"EDC" or "EDC.HCl" refers to 1-ethyl-3-(3-dimethylamino-propyl) carbodiimide hydrochloride salt.

"Et$_3$SiH" refers to triethyl silane, a reducing agent.

"Et$_3$N" refers to triethylamine.

"EtOAc" refers to ethyl acetate.

"Fmoc" refers to 9-fluorenylmethyloxycarbonyl.

"HCA" refers to hydrocinnamoyl group.

"HF" refers to hydrogen fluoride.

"HOBt refers to 1-hydroxybenzotriazole monohydrate.

"IBCF" refers to isobutyl chloroformate.

"IBX reagent" refers to an acronym for periodinane oxidizing reagent.

"IPA" refers to isopropyl alcohol or 2-propanol.

"LAH" refers to LiAlH$_4$.

"LTEPA" refers to lithium tris[(3-ethyl-3-pentyl)oxy] aluminum hydride.

"MBHA resin" refers to methyl-benzhydrylamine resin.

"MeO(Me)NH" or "HNMeOMe" refers to N-methoxy—N-methylamine.

"Mtr" refers to 2,3,6-trimethyl-4-methoxyphenyl sulfonyl.

"Mts" refers to mesitylene-2-sulphonyl.

"NMM" refers to N-methylmorpholine, also called 4-methylmorpholine.

"NMR" refers to Nuclear magnetic resonance spectroscopy.

"[O]" refers to oxidation or oxidizing.

"PAM resin" refers to a resin prepared by coupling a phenylacetic acid derivative to aminomethyl polystyrene.

"PCC" refers to pyridinium chlorochromate.

"Pd/C" refers to palladium on charcoal, a hydrojunction catalyst.

"PDC" refers to pyridinium dichromate.

"Pdn" refers to a pyridone moiety.

"PhCO" refers to benzoyl moiety.

"PMA visualization" refers to visualization of a TLC plate with molybdophosphoric acid solution.

"Pmc" refers to 2,2,5,7,8-pentamethylchroman-6-sulfonyl.

"pMeBzl" refers to 4-methylbenzyl.

"pMeOBzl" refers to 4-methoxybenzyl.

"PrPent" refers to 2-propylpentanoyl moiety.

"PTSA catalyst" refers to para-toluene sulfonic acid.

"Pyr.SO$_3$" refers to pyridine sulfur trioxide complex.

"RP-HPLC" refers to reverse phase high pressure liquid chromatography.

"RT" refers to room temperature.

"TBTU" refers to 2-(1H-benzotriazole-1-yl)-1,1,3,3-tetramethyluronium tetrafluoroborate.

"tBu" refers to tert-butyl.

"TEA" refers to triethylamine.

"TEMPO" (as in 4-methoxy-TEMPO or TEMPO catalyst) refers to 2,2,6,6-tetramethylpiperidinyl nitroxide radical oxidizing reagent.

"TFA" refers to trifluoroacetic acid or the trifluoroacetic acid salt.

"TFMSA" refers to trifluoromethane sulfonic acid.

"THF" refers to tetrahydrofuran.

"tlc" or "TLC" refer to thin layer chromatography.

"TMSOTf" refers to trimethylsilyltrifluoroacetate.

"Tos" refers to p-toluenesulfonyl, also referred to as "Tosyl" or "Ts".

"trityl" refers to triphenylmethyl.

"Z" refers to a Benzyloxycarbonyl protecting group.

BRIEF DESCRIPTION OF THE DRAWINGS

FIG. 1A depicts a protypical endogenous serine protease substrate (1-1) and a protypical peptidal $P_1$-ketoamide enzyme inhibitor of the serine protease substrate (1-2). The amino acids within the substrate are $P_3$, $P_2$, $P_1$, and $P_1$, with the reactive site between $P_1$ and $P_1$. FIGS. 1B, 1C and 1D depict structures for three α-hydroxy-β-amino amide compounds. FIG. 1B depicts the structure for the N-benzoyl-3-phenylisoserine side chain of paclitaxel (Taxol®), FIG. 1C depicts bestatin, and FIG. 1D depicts amastatin. Bestatin is an immune response modulator and analgesic. Amastatin is an aminopeptidase A and leucine aminopeptase inhibitor.

In FIG. 4A, (i) through (xiv) are defined as follows: (i) NaHSO$_3$, H$_2$O; (ii) KCN, KHCO$_3$, THF, H$_2$O ; (iii) HCl, ref lux; (iv) MeOH, H$^+$; (v) reprotect amino group: Boc$_2$O; (vi) NaHCO$_3$, THF, H$_2$O ; (vii) LiOH; MeOH.H$^+$, H$_2$OH$^+$; (viii) $P_1$'amino acid coupling; (ix) deblock $P_1$ amine; (x) coupling reaction; (xi) optionally deblock $P_1$' acid; (xii) optionally elaborate $P_1$' residue, coupling; (xiii)

deprotect side chains; and (xiv) oxidation to give ketoamide. In FIG. 4B, (i) through (v) are defined as follows: (i) (EtS)$_3$CLi, −78° C., THF; (ii) HgCl$_2$, HgO, 95% MeOH, poor overall yields obtained; (iii) LiOH, MeOH, H$_2$O, H$^+$; (iv) P$_1$' amino acid coupling; and (v) follow ix through xiv of FIG. 4A to obtain 4-1.

FIGS. 9A to 9H depict reaction schemes described in Example 1 for synthesis of protected a-aminoaldehyde derivatives used as starting materials for Methods TFA-I, CI, and CV of the present invention. The reactions depicted in FIGS. 9A to FIG. 9H are further described in Example 1. In FIGS. 9A to 9H, the notations (i), (ii), (iii) refer to the reagents used in Example 1 and recited therein.

FIG. 10A depicts the synthesis of a protected cyclohexyl alanine aldehyde (10A-3) described in Example 1b, and its use to synthesize α-hydroxy-β-amino(tert-butyloxycarbonyl)cyclohexylalanine (10A-5) described in Example 6a. In FIG. 10A, (i) through (v) are defined as follows: (i) BH$_3$.THF, THF; (ii) pyridine.SO$_3$, DMSO, TEA; (iii) t-butyl isocyanide, TFA, pyridine, DCM; (iv) 6N HCl, heat; and (v) (Boc)$_2$O, K$_2$CO$_3$, dioxane. In FIG. 10B, (i) through (v) are defined as follows: (i) HNMeOMe.HCl, EDC.HCl, HOBt, NMM, CH$_3$CN; (ii) LAH, −78° C., THF; (iii) t-butyl isocyanide, TFA, pyridine, DCM; (iv) 6N HCl, heat to give 10B-5a; and (v) (BoC)$_2$O, K$_2$CO$_3$, dioxane.

FIG. 19A depicts Compound B which is a thrombin inhibitor described in Example 34 of U.S. Pat. No. 5,703,208. FIG. 19B depicts Compound C which is a thrombin inhibitor described in Example 90 of U.S. Pat. No. 5,656,645. FIG. 19C depicts Eurystatin which is a prolyl endopeptidase inhibitor. FIG. 19D depicts Compound G which is a thrombin inhibitor described in Example 37 of U.S. Pat. No. 5,492,895.

DETAILED DESCRIPTION OF THE INVENTION

General Method

Figure 2A:
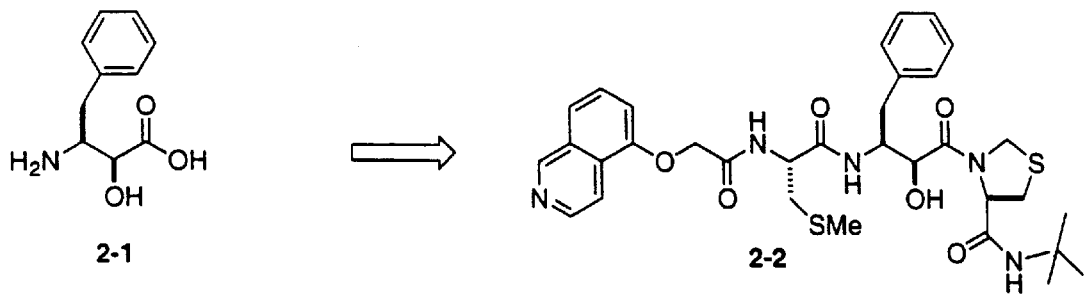
FIG. 2A depicts the structure for the syn isomer of allophenylnorstatine (Apns) (2-1), and the HIV protease inhibitor Kynostatin (KNI-272) (2-2), which incorporates Apns (Mimoto, et al. *Chem. Pharm. Bull.* 40(8):2251–2253 (1992)).
Figure 2B:
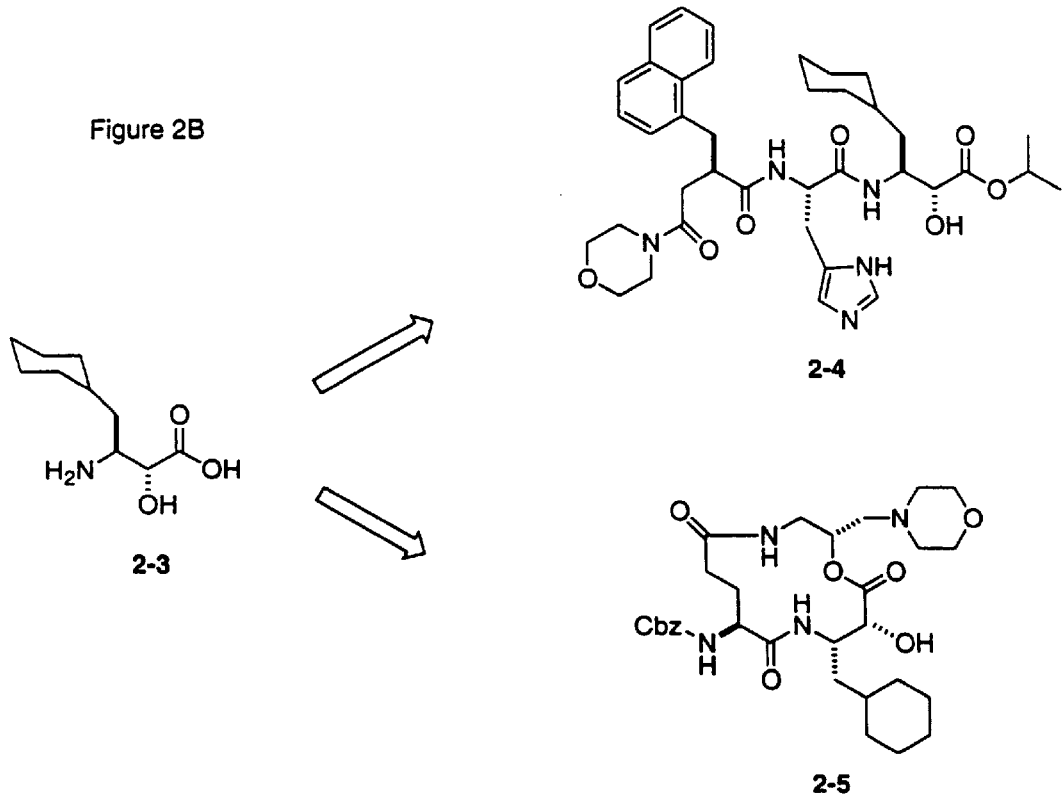
FIG. 2B depicts the structure for the anti isomer of cyclohexylnorstatine (Chns) (2-3) and two renin inhibitors, a Chns isopropyl ester derivative (Y. Kiso, Kyoto Pharm Univ.) (2-4) Iizuka et al., *J. Med. Chem.* 33: 2707–2714 (1990)) and a Chns macrocyclic ester derivative (W. Greenlee, et al., Merck) (2-5) (Dhanoa et al., *Tetrahedron Letters*, 33(13):1725–1728 (1992)), which incorporate Chns.
Figure 3A:
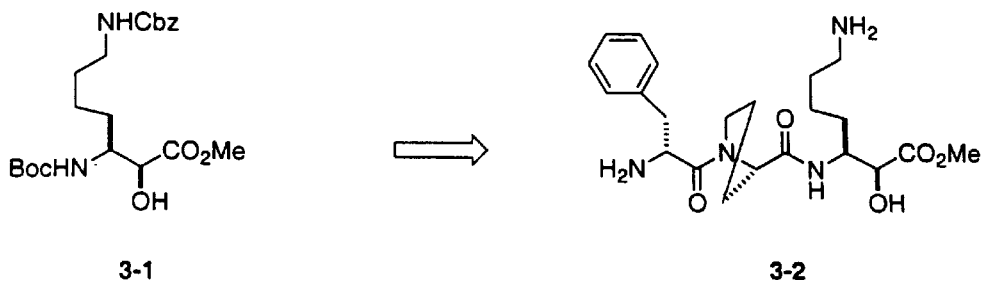
FIG. 3A depicts the structure for an α-hydroxyhomolysine derivative (3-1), and a $P_1$-α-hydroxyhomolysine derivative thrombin inhibitor 3-2 (E. J. Iwanowicz et al., *Bioorganic & Medicinal Chemistry Letters* 2(12):1607–1612 (1992)) that incorporates the α-hydroxyhomolysine derivative.
Figure 3B:
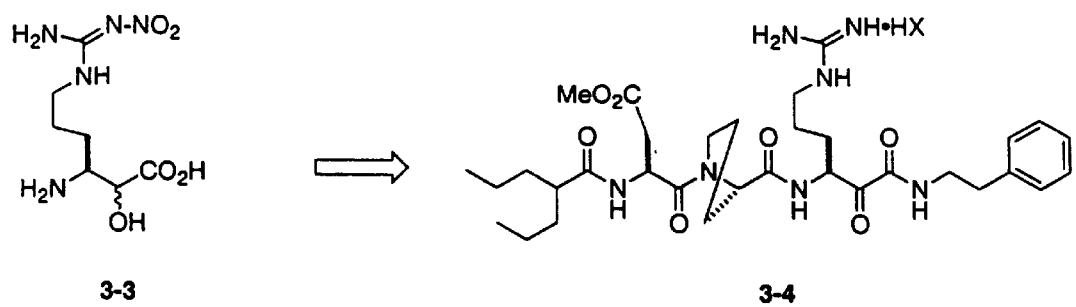
FIG. 3B depicts the structure for an α-hydroxyhomoarginine derivative (3-3) and a thrombin inhibitor that incorporates the derivative, a $P_1$-ketoarginine amide derivative (T. Webb, U.S. Pat. No. 5,371,072) (3-4).
Figure 3C:
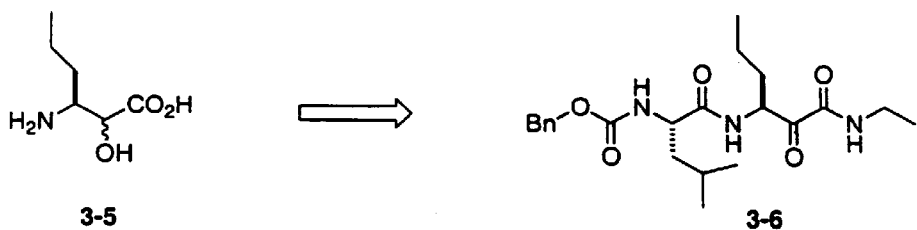
FIG. 3C depicts the structure for 2-hydroxy-3-amino-hexanoic acid (3-5), and a cysteine protease inhibitor that incorporates the acid, a P-norvaline ketoamide peptide derivative (3-6).
Figure 4A:
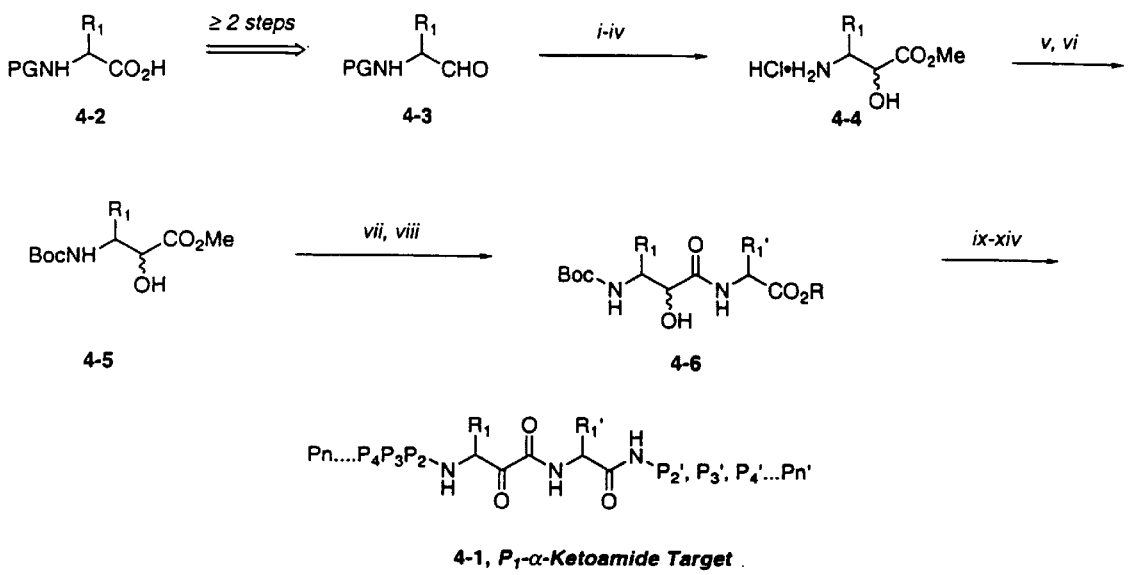
FIG. 4A depicts Scheme 1, which is a scheme for a conventional approach for synthesizing α-hydroxy-β-amino acid derivatives as precursors for $P_1$-α-ketoamide enzyme inhibitors (4-1).
Figure 4B:
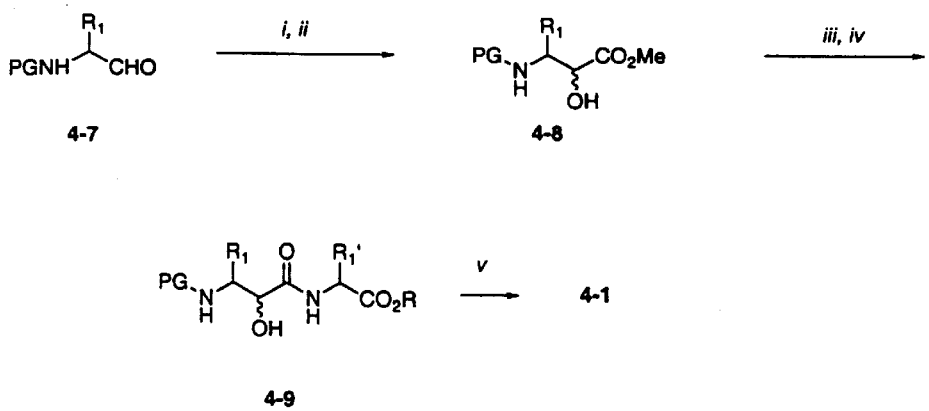
FIG. 4B depicts Scheme 2, which is an alternative approach for synthesizing α-hydroxy-β-amino acid derivatives used to synthesize compounds such as 4-1.
Figure 5:
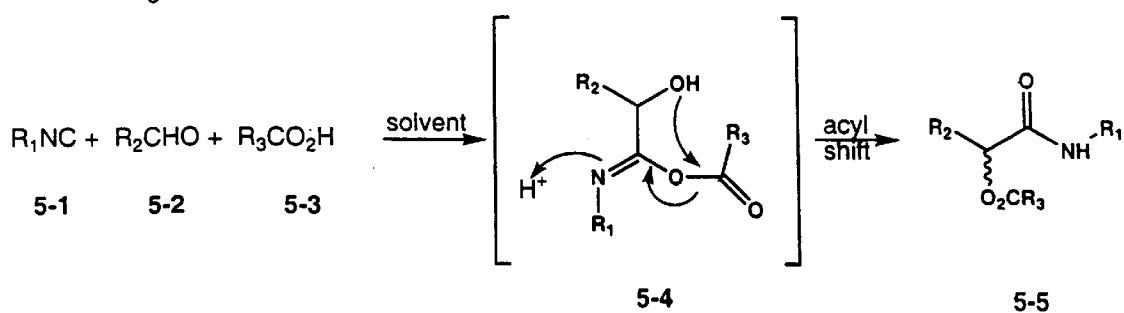
FIG. 5 depicts Scheme 3, which is the reaction scheme for the Passerini reaction.

The present invention is directed to methods of making an α-hydroxy aminoamide derivative of the formula (A):

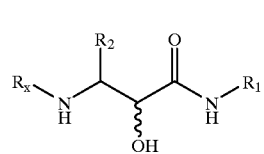

(A)

wherein (i) R$_x$ is —PG or —C(O)R$_3$ where PG is a protecting group;

(ii)
 (a) R$_1$, R$_2$ and R$_3$ are independently selected from the group consisting of alkyl of 1 to about 12 carbon atoms, cycloalkyl of 3 to about 12 carbon atoms, alkenyl of 2 to about 12 carbon atoms, cycloalkenyl of 5 to about 12 carbon atoms, and alkynyl 3 to about 12 carbon atoms, all optionally substituted with 1 to 3 substituents independently selected from Y$_1$, Y$_2$ and/or Y$_3$ aryl of about 5 to about 14 carbon atoms which is optionally mono—, di- or tri-substituted with Y$_1$, Y$_2$, and/or Y$_3$; heteroaryl of about 5 to about 14 ring atoms, with the ring atoms selected from carbon atoms and heteroatoms, wherein the heteroatoms are selected from oxygen, nitrogen and sulfur and which is optionally mono—, di—, tri-substituted with Y$_1$, Y$_2$ and/or Y$_3$; aralkyl of about 6 to about 18 carbon atoms which is optionally mono—, di- or tri-substituted on the aryl ring with Y$_1$, Y$_2$ and/or Y$_3$; and heteroaralkyl of about 5 to about 18 carbon atoms having about 5 to about 14 ring atoms with the ring atoms selected from carbon atoms and heteroatoms, wherein the heteroatoms are selected from oxygen, nitrogen and sulfur and which is optionally mono, di- or tri-substituted on the ring with Y$_1$, Y$_2$ and/or Y$_3$;

(b) alternatively R$_1$ is —CH(R$_5$)C(O)W$_1$ or a peptidyl substituent of the formula —(Xaa$_1$)$_n$W$_2$ wherein R$_5$ is hydrogen, alkyl of 1 to about 12 carbon atoms, cycloalkyl of 3 to about 12 carbon atoms, aryl of 5 to about 14 carbon atoms, or aralkyl of about 7 to about 15 carbon atoms, all optionally substituted with 1 to 3 substituents independently selected from hydroxy, sulfhydryl, alkylthio, carboxyl, amide, amino alkylamino, indolyl, 3-N-formylindolyl, benzyloxy, halobenzyloxy, guanidino, nitroguanidino or imidazolyl optionally substituted with alkoxyalkyl; W$_1$ and W$_2$ are independently selected from —OH, -OZ$_1$, —SH, —SZ$_1$, —NH$_2$, —NHZ$_1$ and —NZ$_1$Z$_2$, wherein each Xaa$_1$ is an independently selected amino acid residue and n is an integer from 1 to 10; or (c) alternatively R$_3$C(O)—is W$_1$CH(R$_5$)C(O)— or R$_4$ wherein R$_4$ is a peptide substituent of the formula Z$_1$X(Xaa$_2$)$_r$— wherein each Xaa$_2$ is an independently selected amino acid residue, r is an integer from 1 to 10 and X is —C(O)—, —S(O)$_2$—, —OC(O)—, or a direct link;

(iii) each Y$_1$, Y$_2$ and Y$_3$ is independently selected from the group consisting of halogen, cyano, nitro, tetrazolyl, guanidino, amidino, methylguanidino, —CH$_3$, —CH$_2$CH$_3$, —CH$_2$CH$_2$CH$_3$, —CH(CH$_3$)$_2$, —CH$_2$CF$_3$, —CH(CF$_3$)$_2$, —OCF$_3$, —OCF$_2$H, —OCF$_2$CF$_3$, —OC(O)NH$_2$, —OC(O)NHZ$_1$, —OC(O)NZ$_1$Z$_2$, —NHC(O)Z$_1$, —NHC(O)NH$_2$, —NHC(O)NHZ$_1$, —NHC(O)NHZ$_1$Z$_2$, —C(O)OH, —C(O)OZ$_1$, —C(O)NH$_2$, —C(O)NHZ$_1$, —C(O)NZ$_1$Z$_2$, —P(O)$_3$H$_2$, —P(O)$_3$(Z$_1$)$_2$, —S(O)$_3$H, —S(O)$_m$Z$_1$, —Z$_1$, —OZ$_1$, —OH, —NH$_2$, —NHZ$_1$, —NZ$_1$Z$_2$, and —S(O)$_m$(CF$_2$)$_q$CF$_3$, wherein m is 0, 1 or 2, q is an integer from 0 to 5; and (iv) each Z$_1$ and Z$_2$ is independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms. These methods comprise the following steps (a), (b) and optionally (c) as set forth below.

(a) First, a protected aminoaldehyde of the formula PGNHCH(R$_2$)CHO, an isonitrile of the formula R$_1$NC, and a carboxy compound of the formula YCO$_2$H wherein Y is —CF$_3$ or —R$_3$ and R$_1$, R$_2$, and R$_3$ are as defined in conjunction with formula (A), are combined in an inert organic solvent to give an amino acyloxy-carboxamide derivative of the formula:

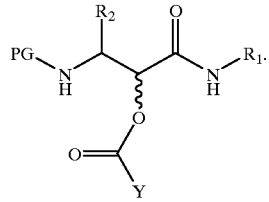

(B)

This reaction is generally conducted at a temperature of about –20° C. to about 40° C. and is generally complete within about 12 to about 240 hours. Suitable organic solvents include dichloromethane, methanol, tetrahydrofuran, combinations thereof, or the like. Where Y is CF$_3$, it is preferable to include a mild organic base such as pyridine.

(b)
(1) To prepare those compounds of formula (A) wherein R$_x$ is PG, the derivative of formula (B) is subjected to selective hydrolysis conditions to remove the α-acyloxy group to yield a compound of formula (A) wherein a R$_x$ is PG. Suitable hydrolysis conditions for compounds where Y is CF$_3$ include extractive aqueous procedures including basic and acidic aqueous extraction. See also Example 3. Suitable hydrolysis conditions wherein Y is R$_3$ include an alkali metal alkoxide in an alcohol, preferably methanol or ethanol.

(b)
(2) To prepare those compounds of formula (A) wherein R$_x$ is —C(O)R$_3$, the derivative of formula (B) is subjected to PG group removal conditions and, if necessary, the pH is adjusted to about 6 to about 9 to effect acyl migration and yield a compound of formula (A) wherein R$_x$ is —C(O)R$_3$. Suitable PG group removal conditions will depend on the PG group and include those summarized in the specification hereinbelow.

According to an alternate aspect, this method may further comprise step (c):

(c) The derivative of formula (A) is then oxidized to give an α-ketoamide derivative of formula (C):

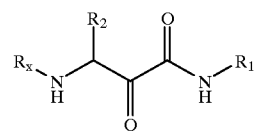

(C)

wherein R$_1$, R$_2$ and R$_x$ are as defined in conjunction with formula (A). A variety of suitable and mild methods for the oxidation of the α-hydroxyamide to the α-ketoamide function have been developed. Oxidation may be effected with the following systems: EDC, DCAA, DMSO, toluene, 0° C. to RT; Pyr.SO$_3$, DMSO, trialkylamine (Et$_3$N, DIPEA) in dichloromethane at about –78° C. to room temperature; Dess-Martin periodinane method at about 0° C. to room temperature; or PDC or PCC in DMF or dichloromethane at about 0° C. to room temperature. Preferred oxidizing conditions include use of EDC and DCA in DMSO and toluene. Further description of oxidation conditions is set forth hereinbelow.

Thus, according to one embodiment of the present invention, R$_x$ is PG and YCO$_2$H is TFA, this embodiment may be termed the "TFA Scheme" or "TFA Methods". According to an alternate embodiment R$_x$ may be either PG, or —C(O)R$_3$ and YCO$_2$H is R$_3$CO$_2$H; this embodiment is termed the "Complex Scheme" or "Complex Methods."

I. TFA SCHEME AND TFA METHODS

Figure 6:
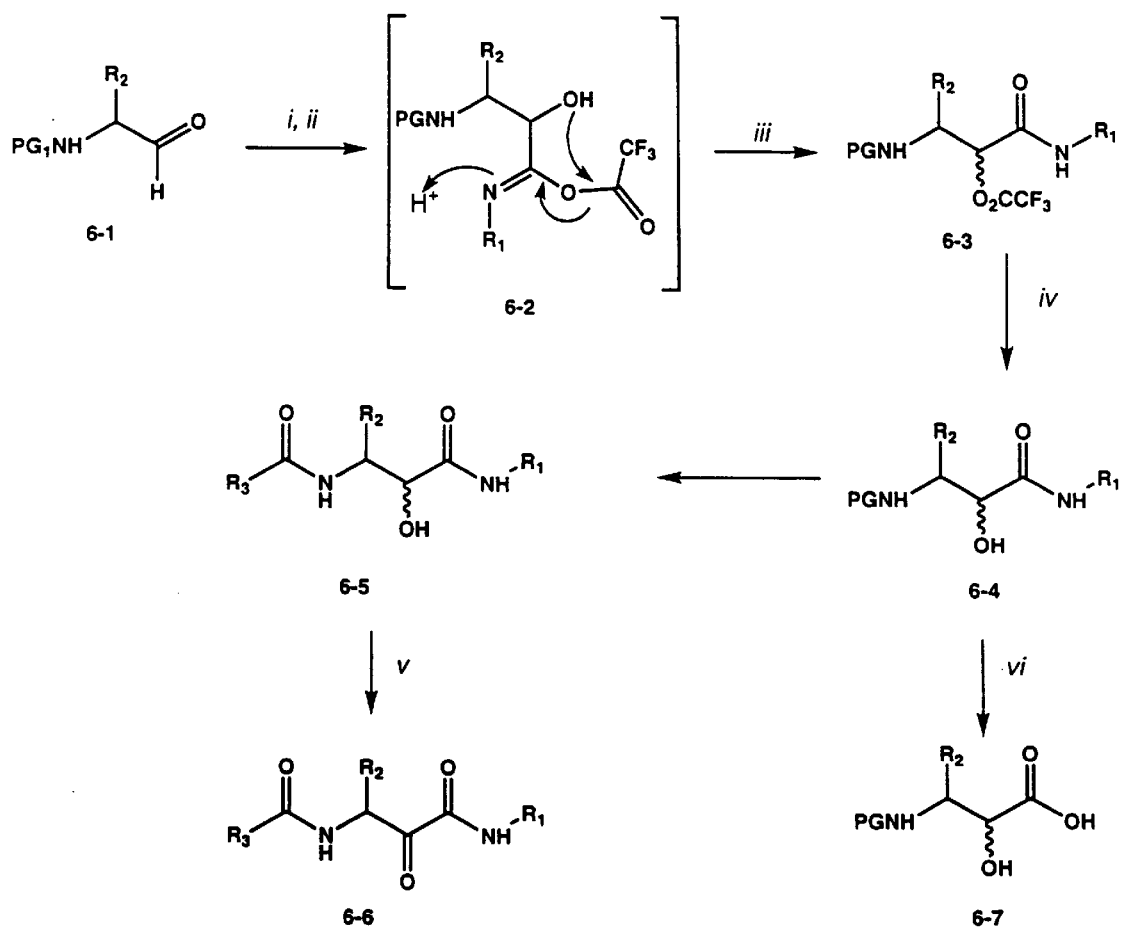
FIG. 6 depicts Scheme 4, which depicts reaction steps in the Trifluoroacetic acid (TFA) reaction method ("TFA-scheme") of the present invention. This reaction scheme depicts synthesis of α-hydroxy-β-aminoamide derivatives (6-4) and their use in preparation of α-ketoamide derivatives (6-6) and α-hydroxy-β-amino carboxy derivatives (6-7). In this figure, (i) through (vi) are defined as follows: (i) CF$_3$CO$_2$H, R$_1$NC; (ii) CH$_2$Cl$_2$, mild organic base such as pyridine; (iii) acyl shift; (iv) hydrolytic work-up for selective hydrolysis of CF$_3$CO group; (v) oxidation; and (vi) for when R$_1$ is t-butyl; acid hydrolysis, reprotection.

According to one embodiment, the methods of the present invention provide novel variations of the Passerini reaction which have resulted in useful synthetic protocols for the novel and rapid assembly of α-hydroxy-β-amino acid derivatives, shown as 6-4 in FIG. 6 (Scheme 4). According to one novel variation, depicted in FIG. 6 (Scheme 4), reaction of a blocked aminoaldehyde 6-1 with the isonitrile R$_1$NC and trifluoroacetic acid in the presence of a mild organic base (such as pyridine and its alkyl derivatives), preferably in an inert organic solvent (such as dichloromethane) at a temperature of about –10° C. to about room temperature yields via intermediate (6-2), the unstable trifluoroacetate derivative (6-3), which, upon mildly hydrolytic conditions such as a mildly basic aqueous extractive workup and/or silica gel flash chromatographic purification, leads to the rapid loss of the trifluoroacetyl group and directly provides a α-hydroxy-β-protected aminoamide derivative (6-4).

Although Passerini reactions employing either a mineral acid, such as sulfuric acid, or trifluoroacetic acid have been reported, the results were substrate-dependent. The sulfuric acid conditions reportedly used were very harsh. (See, Hagedorn and Eholzer, *Chem. Ber.* Jahrg. 98:936 (1965).) The trifluoroacetic acid conditions used in the reported procedures usually led to erratic product distributions accompanied by significant amounts of undesirable by-products and only low to modest yields of useful α-hydroxyamide products (See, Lumma, *J. Org. Chem.* 46:3668 (1981)).

The methods of Applicants' invention provide intermediate 6-4 which is a useful precursor for both the preparation of α-ketoamide protease inhibitors 6-6 (via intermediate (6-5) and α-hydroxy-β-amino acid derivative 6-7. Acidic hydrolysis of intermediate 6-4 where R$_1$ is t-butyl, typically with a mineral acid such as hydrochloric acid at a temperature from about 50° C. to reflux and optional reprotection of the β-amino group (when PG is Boc) delivers the α-hydroxy-β-amino carboxylic acid derivative 6-7.

Alternately, deprotection of the β-amino group of 6-4 followed by an acylation reaction delivers a suitable advanced intermediate 6-5. A large variety of functionality, including delicate and sensitive moieties, may be contained within the context of the $P_1$–$P_3$ residues of 6-5. Oxidation of 6-5 affords the desired α-ketoamide derivative 6-6.

The resultant ketoamide moiety of α-ketoamide derivative 6-6 can be masked with a suitable semicarbazone protecting group. This offers the added advantage of providing a second functional handle to the molecule, allowing for convenient tethering via an appropriate linker onto a specified resin matrix from which subsequent chemistries may be executed, e.g., synthesis of libraries and solid phase synthesis of desired chemical entities. Upon completion, the semicarbazone group is removed to yield the final product. See FIG. 15.

Thus, according to this embodiment, the TFA scheme of the present invention provides methods which include TFA Methods I through V described below.

In one aspect, the invention is a method (TFA Method I) of making an α-hydroxy β-protected aminoamide derivative having the formula (TFA-I):

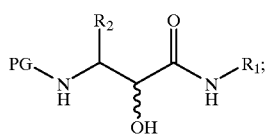

(TFA-I)

wherein PG is a protecting group, $R_1$ and $R_2$ are as defined in connection with formula (A) hereinabove, and $R_1$ is derived from an isonitrile $R_1NC$, which comprises the steps:

(a) combining an N-terminally blocked aminoaldehyde PGNHCH[$R_2$]CHO, an isonitrile $R_1NC$, trifluoroacetic acid, and a mild organic base in an inert organic solvent at a temperature from about −10° C. to about room temperature for a time of about 12 hours to about 72 hours, to give a trifluoroacetate derivative of the formula:

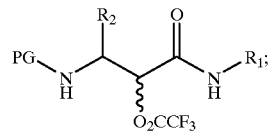

(b) treating the trifluoroacetate derivative from step (a) with hydrolysis conditions such as a hydrolytic work up via extractive aqueous procedures, whereby the trifluoroacetyl group hydrolyses to yield an α-hydroxy β-protected aminoamide derivative; and (c) optionally isolating the α-hydroxy β-protected aminoamide derivative of step (b) so made.

The invention also provides certain α-hydroxy β-protected aminoamide derivatives made by TFA Method I, as well as compositions comprising or incorporating an α-hydroxy β-protected aminoamide derivative.

TFA Method I is further described and exemplified in Examples 3 and 5 to 8, Table 1, and in other portions of the specification.

In a second aspect, the present invention is directed to a method (TFA Method II) of making an α-hydroxyl-β-amino carboxylic acid derivative having the formula (TFA-II):

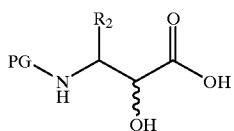

(TFA-II)

wherein PG and $R_2$ are as defined in connection with formula (A), which comprises the steps of:

(a) subjecting an α-hydroxy β-protected aminoamide derivative (TFA-I) made by TFA Method I to hydrolysis; and (b) optionally, recovering the α-hydroxyl-β-amino carboxylic acid derivative product (TFA-II) of hydrolysis. When the PG is Boc, TFA Method II further comprises the additional step of reprotecting the β-amino functionality after step (b).

The invention also contemplates certain α-hydroxyl-β-amino carboxylic acid derivatives made by TFA Method II, as well as compositions comprising or incorporating a α-hydroxyl-β-amino carboxylic acid derivative.

TFA Method II is further described and exemplified in Example 6 and in other portions of the specification.

In a further aspect, the invention provides a method (TFA Method III) of making an α-ketoamide derivative having the formula (TFA-III):

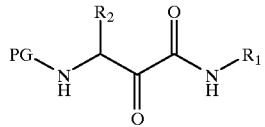

(TFA-III)

wherein PG, $R_1$, and $R_2$ are as defined in conjunction with formula (A) and $R_1$ is derived from an isonitrile $R_1NC$, which comprises the steps of:

(a) oxidizing the α-hydroxy group of an α-hydroxy β-protected aminoamide derivative (TFA-I) made by TFA Method I to give an α-ketoamide derivative; and (b) optionally isolating the α-ketoamide derivative.

The invention also provides certain α-ketoamide derivatives made by TFA Method III, as well as compositions comprising or incorporating an α-ketoamide derivative.

TFA Method III is further described and exemplified in Example 5 (part a), Example 7, and Example 8, and in other portions of the specification.

An additional aspect of the invention is directed to a method (TFA Method IV) of making a semicarbazone-protected ketoamide derivative having the formula (TFA-IV):

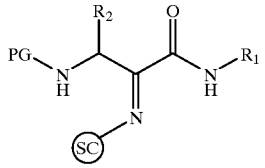

(TFA-IV)

wherein PG, $R_1$ and $R_2$ are as defined in connection with formula (A), $R_1$ is derived from an isonitrile of formula $R_1NC$, and SC is a semicarbazone of the formula —NHCONHQ, wherein Q is selected from the group consisting of hydrogen, alkyl of 1 to about 12 carbon atoms; alkenyl of 2 to about 12 carbon atoms; alkynyl of 3 to about 12 carbon atoms, aryl of 5 to about 18 carbon atoms; heteroaryl of 5 to about 18 ring atoms with the ring atoms selected from carbon atoms and heteroatoms wherein the heteroatoms are selected from oxygen, nitrogen and sulfur; aralkyl; di-arylalkyl and tri-arylalkyl; which comprises the steps of:

(a) combining an α-ketoamide derivative made by TFA Method III with a semicarbazide of formula NH$_2$NHCONHQ under conditions permitting formation of a semicarbazone-protected ketoamide derivative; and (b) optionally isolating the semicarbazone-protected α-ketoamide derivative thus formed.

According to an additional aspect, TFA Method IV comprises the further steps (TFA Method IV') of: (a) removing the group =N—SC from the protected α-ketoamide derivative to give a deprotected α-ketoamide derivative of formula (TFA-III); and (c) optionally isolating the deprotected α-ketoamide derivative.

The invention also provides certain semicarbazone-protected or deprotected α-ketoamide derivatives made by TFA Method IV or IV', as well as compositions comprising or incorporating a semicarbazone-protected or deprotected α-ketoamide derivative.

TFA Methods IV and IV' are further described and exemplified in Example 5 (parts b and c), and Example 8, and in other portions of the specification.

A further aspect of the invention is directed to a method (TFA Method V) of making a peptidyl ketoamide enzyme inhibitor having the formula (TFA-V):

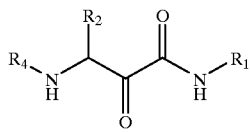

(TFA-V)

wherein $R_1$, $R_2$ and $R_4$ are as defined in connection with formula (A). According to a preferred aspect, $R_1$, $R_2$, and $R_4$ are selected so that the resulting compound of formula (TFA-V) comprises the $P_3$-$P_2$-$P_1$-$P_1'$ position of peptide residues relative to the scissile bond of $P_1$-$P_1'$, where $R_2$ is the amino acid side chain at $P_1'$ $R_1$ is a peptidyl substituent corresponding to $P_1'$, and $R_4$ is a peptidyl substituent corresponding to $P_3$-$P_2$. TFA Method V comprises the steps of:

(a) removing protecting group PG from a derivative made by any of TFA Methods II, III, IV or IV', to form a deprotected derivative;

(b) combining the deprotected derivative with an intermediate of the formula $R_4$-LG, wherein LG is a leaving group, under conditions permitting bond formation between the deprotected amino of the derivative and the $R_4$ group to form an elongated peptidyl composition, (c) if a derivative made by TFA Method I or IV is used in step (a), subjecting the elongated peptidyl composition to oxidation to form a peptidyl ketoamide enzyme inhibitor of formula (TFA-V) (if a derivative of either formula (TFA-III) or formula (TFA-IV) is used in step (a) no oxidation step is needed; however, if a derivative of formula (TFA-IV) is used, a step which effects removal of the =N—SC group is needed); and (d) optionally isolating the peptidyl ketoamide enzyme inhibitor thus formed.

Suitable leaving groups LG for the intermediate $R_4$-LG include halogen, —OH, lower alkoxy, —OSO$_2$CF$_3$, —OSO$_2$CH$_3$, —OSO$_2$(p-Me-phenyl), and the like. Preferred halogens include Cl, F and Br.

The present invention also provides certain novel peptidyl ketoamide enzyme inhibitors made by TFA Method V, as well as compositions comprising or incorporating such as peptidyl ketoamide enzyme inhibitors.

TFA Method V is further described and exemplified in Example 8 and in other portions of the specification.

II. COMPLEX SCHEME AND COMPLEX METHODS

Figure 7:
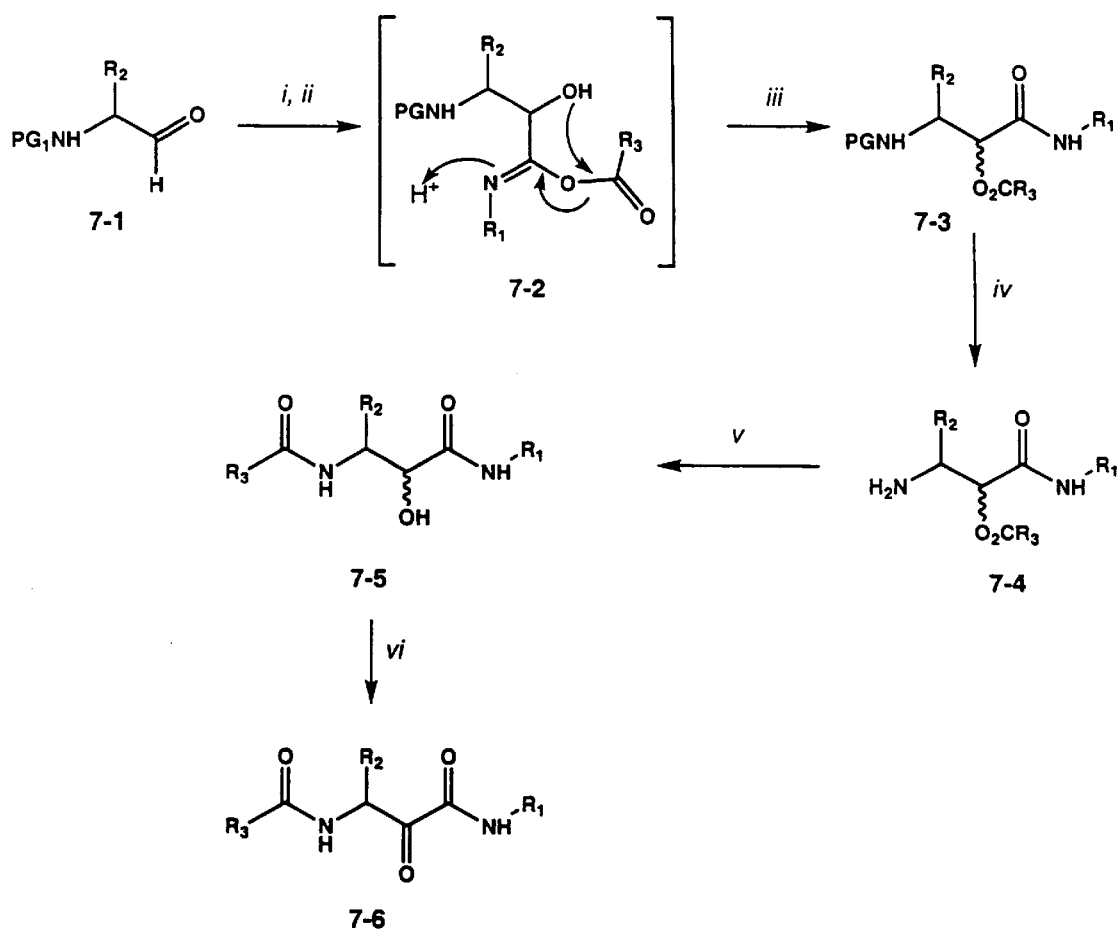
FIG. 7 depicts Scheme 5, which depicts reaction steps of one aspect of the Complex reaction methods of the present invention ("Complex scheme"). This reaction scheme depicts synthesis of α-hydroxy-β-aminoamide derivatives (7-5) and their use in synthesizing α-ketoamide derivatives (7-6). In this figure, (i) through (vi) are defined as follows: (i) R$_3$CO$_2$H, R$_1$NC; (ii) CH$_2$Cl$_2$ or MeOH, 0° to room temperature; (iii) acyl shift; (iv) removal of amino protecting group (PG$_1$); (v) acyl group migration to give 7-5; (vi) oxidation to give 7-6.

A second embodiment of the present invention, termed the Complex Scheme and outlined in FIG. 7/Scheme 5, includes further extensions of the Passerini reaction which Applicants have developed. This embodiment provides an α-hydroxy-β-amino acid derivative 7-5 or an α-ketoamide derivative 7-6, wherein PG, $R_1$, $R_2$, and $R_3$ are as defined in connection with formula (A).

According to this embodiment, a tandem three-step process is executed which involves a sequential addition reaction, a-amino group deprotection, and adjustment of the reaction solution pH to about 6 to 9, wherein an acyl migration ensues. Each step of this tandem process occurs with high efficiency and under mild conditions. Thus, the addition reaction of protected α-aminoaldehyde 7-1 with an isonitrile $R_1$NC and a carboxylic acid $R_3$CO$_2$H in a suitable solvent, e.g., methanol, ethanol, dichloromethane, tetrahydrofuran or mixtures thereof, over a temperature range of about −20° C. to about 40° C. generates the intermediate 7-2, which rapidly undergoes an acyl shift and proton transfer to afford the β-protected amino α-acyloxycarboxamide derivative 7-3. Removal of the β-amino-protecting group using conventional deprotection procedures and, if needed, adjustment of the solution pH to a value of between 5 and 12, typically to pH values between 6 to 9, in suitable inert aqueous and/or organic solvents, using conditions known to those skilled in the art of organic synthesis, affords the intermediate 7-4. Intermediate 7-4 undergoes a facile acyl migration under these mild conditions at temperatures of about −20° C. to about 80° C., preferably at temperatures of about 0° C. to about 25° C., and delivers the functionalized α-hydroxyamide product 7-5. Optional orthogonal deprotection, followed by oxidation of 7-5, as described, produces the ketoamide target compound 7-6.

In one aspect, the present invention is directed to a method (Complex Method I) of making an α-hydroxyl-β-amino amide derivative having the formula (CI):

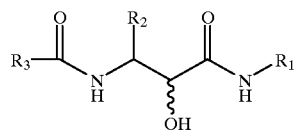

(CI)

wherein PG, $R_1$, $R_2$, and $R_3$ are as defined in conjunction with formula (A) and $R_1$ and is derived from an isonitrile $R_1$NC, and $R_3$ is derived from the carboxylic acid $R_3$CO$_2$H, which comprises the steps:

(a) combining an N-terminally blocked aminoaldehyde of the formula PGNHCH(R$_2$)CHO, an isonitrile R$_1$NC, and a carboxylic acid R$_3$CO$_2$H, in an inert organic solvent at a temperature from about −20° C. to about 40° C. for a time of about 12 hours to about 240 hours, to form a mixture comprising an amino α-acyloxycarboxamide derivative 7-3 (CIA) of the formula:

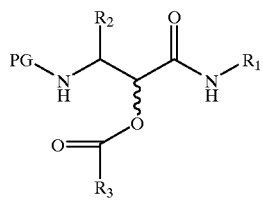

(CIA)

(b) removing PG from the amino a-acyloxycarboxamide derivative and, if required, adjusting the pH to a value between about 6 and about 9, to effect acyl migration and formation of an α-hydroxy-β-aminoamide derivative 7-5 of formula CI; and (c) optionally isolating the α-hydroxy β-aminoamide derivative thus formed.

The invention also provides certain α-hydroxy β-aminoamide derivatives made by Complex Method I, as well as compositions comprising or incorporating an α-hydroxy β-aminoamide derivative.

Complex Method I is further described and exemplified in Example 4, Example 9 (steps a, b, c), Example 10 (steps f, g, h), and Tables 2 and 3, and in other portions of the specification.

In another aspect, the present invention is directed to a method (Complex Method II) of making an α-ketoamide derivative having the formula (CII):

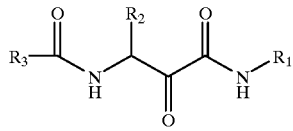

(CII)

wherein $R_1$, $R_{21}$ and $R_3$ are as defined in conjunction with formula (A) and $R_1$ is derived from an isonitrile $R_1NC$, and $R_3$ is derived from a carboxylic acid $R_3CO_2H$, which comprises the steps:

(a) oxidizing the α-hydroxy β-aminoamide derivative (CI), 7-5, made by Complex Method I to give an α-ketoamide derivative 7-6 of formula CII, and (b) optionally isolating the α-ketoamide derivative product of oxidation.

The invention is also directed to certain α-ketoamide derivatives made by Complex Method II, as well as compositions comprising or incorporating such an α-ketoamide derivative.

Complex Method II is further described and exemplified in Example 9 (step d) and in other portions of the specification.

Optionally, Complex Method II can include further steps to make (Complex Method III) a semicarbazone-protected ketoamide derivative having the formula (CIII):

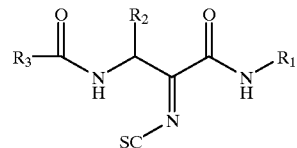

(CIII)

wherein $R_1$, $R_2$, and $R_3$ are as defined in conjunction with formula (A), $R_1$ is derived from an isonitrile $R_1NC$, $R_3$ is derived from a carboxylic acid $R_3CO_2H$, and SC is a semicarbazone with the formula —NHCONHQ, wherein Q is selected from the group consisting of hydrogen, alkyl of 1 to about 12 carbon atoms, alkenyl of 2 to about 12 carbon atoms, alkynyl of 3 to about 12 carbon atoms, aryl of 5 to about 18 carbon atoms, heteroaryl of 5 to about 18 ring atoms with the ring atoms selected from carbon atoms and heteroatoms wherein the heteroatoms are selected from oxygen, nitrogen and sulfur, aralkyl, di-arylalkyl and tri-arylalkyl which comprises the additional steps:

(a) combining an α-ketoamide derivative made by Complex Method II with a semicarbazide with the formula $NH_2NHCONHQ$ under conditions permitting formation of a semicarbazone-protected ketoamide derivative of formula (CIII); and (b) optionally isolating the semicarbazone-protected ketoamide derivative thus formed.

Additionally, Complex Method III may comprise the further steps (Complex Method III') of: (a) removing the group =N—SC from the semicarbazone-protected ketoamide derivative to form a deprotected ketoamide derivative; and (b) optionally isolating the α-ketoamide derivative thus formed.

The invention also is directed to certain semicarbazone-protected or deprotected α-ketoamide derivatives made by Complex Methods III or III', as well as compositions comprising or incorporating such a semicarbazone-protected or deprotected α-ketoamide derivative.

Complex Methods III and III' are further described and exemplified in Examples 5, 7, and 8 for TFA Methods IV and IV', except that, instead of using the product of TFA Method III as the starting material, the product of Complex Method III is used as the starting material. Complex Methods III and III' also are further described and exemplified in other portions of the specification.

Another aspect of the invention is directed to a method (Complex Method IV) of making a peptidyl ketoamide enzyme inhibitor having the formula (CIV):

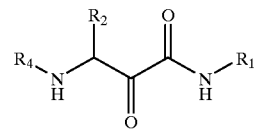

(CIV)

wherein $R_1$, $R_2$ and R4 are as defined in connection with formula (A). According to a preferred aspect of this method, $R_1$, $R_2$ and $R_4$ are selected so as to define the $P_3$-$P_2$-$P_1$-$P_1'$ position of peptide residues relative to the scissile bond of $P_1$-$P_1'$, where $R_2$ is the amino acid side chain at $P_1$, $R_1$ is a peptidyl substituent corresponding to $P_1'$, and $R_4$ is a peptidyl substituent corresponding to $P_3$-$P_2$. Complex method IV comprises the steps of:

(a) combining an N-terminally blocked aminoaldehyde of the formula PGNHCH($R_2$)CHO, an isonitrile $R_1$NC, and a carboxylic acid $R_3CO_2H$, wherein the $R_3$C(O)— group of the carboxylic acid group provides the $R_4$ group of the peptidyl product ketoamide enzyme inhibitor, in an inert organic solvent at a temperature from about −20° C. to about 40° C. for a time of about 12 hours to about 240 hours, to form a mixture comprising a β-amino α-acyloxycarboxamide derivative of the formula:

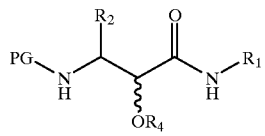

(b) removing protecting group PG from the β-amino α-acyloxycarboxamide derivative and, if needed, adjusting the pH to a value between about 6 and about 9, to effect acyl migration and the formation of an α-hydroxy-β-aminoamide derivative of the formula:

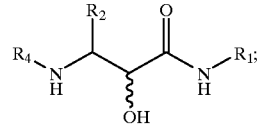

(c) oxidizing the α-hydroxy group of the α-hydroxy-β-aminoamide derivative to oxidation to form a peptidyl ketoamide enzyme inhibitor of formula (CIV); and (d) optionally isolating the product peptidyl ketoamide enzyme inhibitor thus formed.

The invention is also directed to certain peptidyl ketoamide enzyme inhibitors made by Complex Method IV, as well as to compositions comprising or incorporating a peptidyl ketoamide enzyme inhibitor.

Complex Method IV is further described and exemplified in Example 9 (steps a to e) and in other portions of the specification.

In another aspect, the invention is directed to a method (Complex Method V) of making an α-hydroxy β-protected aminoamide derivative having the formula (CV):

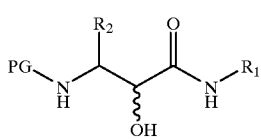
(CV)

wherein, PG is a protecting group, $R_1$ and $R_2$ are as defined in conjunction with formula (A) and $R_1$ is derived from an isonitrile $R_1$NC, which comprises the steps:

(a) combining an N-terminally blocked aminoaldehyde of the formula PGNHCH($R_2$)CHO, an isonitrile $R_1$NC, and a carboxylic acid $R_3CO_2H$, wherein $R_3$ is defined in conjunction with formula (A), in an inert organic solvent at a temperature from about −20° C. to about 40° C. for a time of about 12 hours to about 240 hours, to form a mixture comprising an amino a-acyloxycarboxamide derivative;

(b) subjecting the amino α-acyloxycarboxamide derivative to selective hydrolysis with an alkali metal alkoxide to form an α-hydroxy β-protected aminoamide derivative of formula (CV); and (c) optionally isolating the α-hydroxy β-protected aminoamide derivative thus formed.

The invention also provides certain α-hydroxy β-protected aminoamide derivatives made by Complex Method V, as well as compositions comprising or incorporating such as α-hydroxy β-protected aminoamide derivative.

The α-hydroxy β-protected aminoamide derivatives made by Complex Method V have the same formula as those made by TFA Method I, and can replace the TFA Method I compounds in all respects, including use in TFA Methods II, III, and V described hereinabove.

Complex Method V is further described and exemplified in Example 11 and in other portions of the specification.

III. General Comments, Considerations, and Preferred Aspects of the TFA and Complex Reactions A. Comments pertaining to both TFA and complex reactions 1. Protecting Groups In practicing the methods of the present invention, the following considerations apply to the selection of a-amino protecting groups, side chain protecting groups, and carboxy protecting groups. In selecting suitable α-amino protecting groups (PG) to be used during the synthesis of the N-terminally-blocked aminoaldehydes of formulas (6-1) and (7-1) (see FIGS. 6 and 7), the a-amino protecting group should (i) render the a-amino function inert under the conditions employed in the coupling reaction, (ii) be readily removable after the coupling reaction under conditions that will not remove side chain or carboxy terminus protecting groups and (iii) eliminate the possibility of racemization upon activation prior to coupling.

A suitable α-amino protecting group, PG, may be selected from the group consisting of acid labile α-amino protecting groups known to those of skill in the art (cleavage conditions for such groups are noted below in brackets or text). Suitable protecting groups, PG, include the following:

(a) triphenylmethyl (trityl); this group is cleaved under very mild acid conditions [1% TFA];

(b) tert-butyloxy carbonyl (Boc), t-amyloxycarbonyl, adamantyloxycarbonyl, 4-methoxy benzyloxycarbonyl; these protecting groups require moderately strong acids for their removal, such acids capable of removing those groups include as trifluoroacetic acid, hydrochloric, or boron trifluoride in acetic acid; and (c) benzyloxycarbonyl (CBz), 2-chlorobenzyloxycarbonyl (2-ClZ), cycloalkyloxycarbonyl, and isopropyloxycarbonyl; these protecting groups require stronger acids for their removal, such acids include hydrogen fluoride, hydrogen bromide or boron trifluoroacetate in trifluoro acetic acid. The CBz and the 2-ClZ groups may also be cleaved by hydrogenation under palladium on carbon in methanol.

A suitable a-amino protecting group, PG, also may be selected from the group consisting of base labile α-amino protecting groups. These groups include fluorenylmethyloxycarbonyl and allyloxycarbonyl. For instance, fluorenylmethyloxycarbonyl (Fmoc) may be cleaved by using 20% piperidine/DMF or excess diethylamine in THF. The cleavage of another suitable a-amino protecting group, allyloxycarbonyl (Alloc) may be assisted by Pd(O) catalyst transfer of the allyl group to a nucleophile such as morpholine, dimedone, tributyl tin hydride and N-methyl aniline.

Preferred α-amino protecting groups (PG) include Boc, Fmoc, Alloc, and Cbz.

An amino acid side-chain protecting group should: (i) render the protected side chain functional group inert under the conditions employed in the coupling reaction, (ii) be stable under the conditions employed in removing the α-amino or the carboxy terminus protecting groups, and (iii) be readily removable upon completion of the desired peptide under reaction conditions that will not alter the structure of the peptide chain.

A suitable amino acid side chain protecting group (methods for cleavage of these protecting groups are shown in brackets []) may be selected from such groups known to those skilled in the art and include:

(a) for protection of lysine amino group, any of the groups mentioned above for the protection of α-amino groups;

(b) for protection of the arginine guanidino group, preferred protecting groups include nitro [$H_2$/Pd/C, HF], benzyloxycarbonyl (CBz) [HF, TFMSA, TMSOTf, $H_2$/Pd/C], tert-butyloxycarbonyl (Boc) [TFA], 2,2,5,7, 8-pentamethylchroman-6-sulfonyl (Pmc) [TFA], 2,3,6-trimethyl-4-methoxyphenylsulfonyl (Mtr) [TFA], p-toluenesulfonyl (Tos) [HF, TFMSA], mesitylene-2-sulphonyl (Mts) [HF, TFMSA], allyloxycarbonyl (Alloc) [Pd(0), morpholine or dimedone];

(c) for protection of serine and threonine hydroxyl groups, suitable protecting groups include trityl [1% TFA], tert-butyl [TFA], benzyl, and substituted benzyl groups such as 4-methoxybenzyl, 4-chlorobenzyl, 2-chlorobenzyl, and 2,6-dichlorobenzyl which are cleaved by a similar method [HF, TFMSA, $H_2$/Pd/C];

(d) for protection of tyrosine phenolic group, suitable protecting groups include as tert-butyl [TFA], trityl [1% TFA], and benzyl, 2-bromobenzyl and 2,6-dichlorobenzyl, all cleaved by the same reagents [HF, TFMSA, $H_2$/Pd/C];

(e) for protection of aspartic and glutamic acid side chain carboxy groups, suitable protecting groups include methyl [$OH^-$, $H^+$], ethyl [$OH^-$, $H^+$], t-butyl [TFA], allyl [Pd(O), morpholine], cyclohexyl [HF, TMSOTf], or benzyl groups [HF, TFMSA, TMSOTf, $H_2$/Pd/C];

(f) for protection of asparagine and glutamine side chains, suitable protecting groups include trityl [TFA] and xanthyl [TFA];

(g) for protection of a histidine imidazole group, suitable protecting groups include 2,4-dinitrophenyl (Dnp) [thiophenol], trityl [TFA], benzyloxymethyl (Bom) [HF, TFMSA, TMSOTf, $H_2$/Pd/C], p-toluene sulfonyl (Tos) [HF, TFMSA], and benzyloxycarbonyl (Cbz) [HF, $H_2$/Pd/C];

(h) for protection of a cysteine sulfhydryl group, suitable protecting groups include trityl [TFA], 4-methylbenzyl (pMeBzl) [HF, TFMSA], 4-methoxybenzyl (pMeOBzl) [HF, TFMSA], acetamidomethyl (Acm) [$I_2$, $Hg^{2+}$], tert-Butyl (tBu) [$Hg^{2+}$]; and (i) for protection of a tryptophan indole group, suitable protecting groups include formyl [10% piperidine in DMF, followed by HF] and tert-butyloxycarbonyl (Boc) [TFA].

A carboxy terminus protecting group ($PG_2$ within $R_1$ of $R_1NC$) should: (i) render the protected functional group inert under the conditions employed in the coupling reaction, (ii) be stable under the conditions employed in removing the α-amino or the side chain protecting groups, and (iii) be readily removable upon completion of the desired peptide under reaction conditions that will not alter the structure of the peptide chain.

For the protection of the carboxy terminus of amino acids suitable protecting groups include methyl [$OH^-$, $H^+$], ethyl [$OH^-$, $H^+$], tert-butyl [TFA], benzyl [$OH^-$, $H_2$/Pd/C] and allyl [Pd(0), morpholine] groups.

With respect to steps within the Methods of the present invention that employ oxidation, orthogonal deprotection is optional.

2. $R_2$ Groups

According to a preferred aspect of the present invention, the $R_2$ group of the N-terminally blocked aminoaldehyde PGNHCH($R_2$)CHO starting material is selected from any suitably protected side chain of a natural or unnatural amino acid. The starting aminoaldehydes are obtained by methods known in the art and/or described in Example 1 herein.

3. Isonitrile Compound ($R_1NC$)

Any isonitrile is suitable for use in the methods of the present invention, including those made by the method of Seebach in Chem. Ber. 121:507–517 (1988), and Pospisek, in Collection Czechoslovak Chem. Commun. 52:514–521 (1987). The synthesis of allyl isocyanoacetate is a preferred isonitrile, and its synthesis is provided in Example 2, herein. Commercially available isonitriles also are suitable for use in the present invention, including those selected from the group consisting of tert-butyl isocyanide, 1,1,3,3-tetramethylbutyl isocyanide, benzyl isocyanide, p-toluene sulfonyl methyl isocyanide, cyclohexyl isocyanide, hexyl isocyanide, 2,6-dimethylphenyl isocyanide, i-propyl isocyanide, 2-morpholine ethyl isocyanide, and (trimethylsilyl)methyl isocyanide.

Preferred isonitriles for use in the methods of the present invention include those wherein $R_1NC$ is ethyl, allyl and t-butyl isocyanoacetate. Especially preferred isonitriles are methyl isocyanoacetate, ethyl isocyanoacetate, tert-butyl isocyanide, tert-butyl isocyanoacetate, and allyl isocyanoacetate, with tert-butyl isocyanide and allyl isocyanoacetate being most preferred.

4. Mild Organic Base

Mild organic bases suitable for use in methods of the invention are those that have the characteristic of being a non-nucleophilic hindered organic base. Suitable mild organic bases include pyridine, collidine, lutidine, 2,6-di-tert-butyl pyridine. Preferred mild organic bases include collidine and 2,6-di-tert-butylpyridine.

5. Preferred Organic Solvents

Preferred organic solvents suitable for use in methods of the present invention include dichloromethane, methanol, ethanol, tetrahydrofuran, acetonitrile, and mixtures thereof. A referred inert organic solvent is dichloromethane.

6. Oxidation Conditions

The oxidation conditions used in methods of the present invention are those commonly known in the art, including the Moffatt, Von-Doering and Dess-Martin reactions, and the following:

(i) pyridinium chlorochromate in dichloromethane or DMF (*J. Org. Chem.* 50:2607 (1985));

(ii) pyridinium dichromate in dichloromethane or DMF (*J. Org. Chem.* 41:380 (1976));

(iii) pyridinium dichromate, acetic anhydride in dichloromethane (*Tet. Lett.* 26:1699 (1985));

(iv) pyridine-sulfur trioxide, triethylamine, dimethyl sulfoxide in dichloromethane (Von Doering oxidation; see Example 1b);

(v) pyridine-sulfur trioxide, N,N-diisopropylethylamine, dimethylsulfoxide in dichloromethane (Von Doering oxidation; see Example 1b);

(vi) oxalyl chloride, dimethyl sulfoxide, triethylamine in dichloromethane (Swern oxidation; see Example 1b);

(vii) dichloroacetic acid, EDC, dimethylsulfoxide in dichloromethane or toluene (Moffat oxidation; see Example 1b);

(viii) Dess Martin Periodinane in dichloromethane (see Example 1b);

(ix) IBX reagent in dichloromethane (*Tet. Lett.* 35:8019 (1994));

(x) 4-methoxy-TEMPO or TEMPO catalyst, NaOCl, in dichloromethane/water 2-phase system (*J. Am. Chem. Soc.* 106:3374 (1984)).

7. Semicarbazone Formation and Removal

Figure 8:
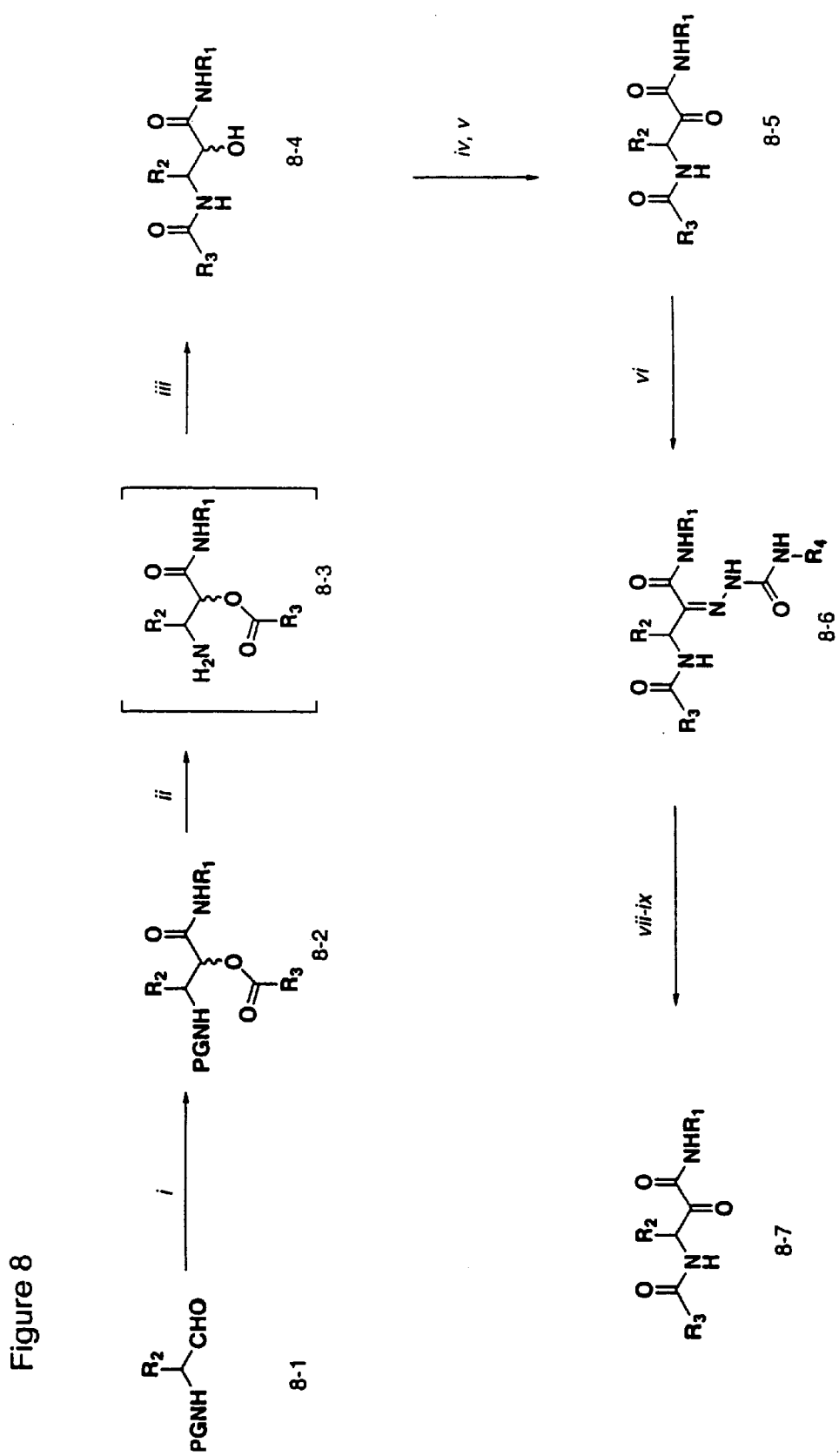
FIG. 8 depicts Scheme 6, which depicts reaction steps of one aspect of the Complex scheme for formation of a ketoamide target compound and formation of semicarbazone-protected intermediate, and steps in semicarbazone-protection and deprotection of an α-ketoamide derivative made by a method of the present invention. This method depicts synthesis of a ketoamide target compound or intermediate (8-5) which subsequently may be used to synthesize an elaborated ketoamide target compound or intermediate (8-7). In this figure (i) through (ix) are defined as follows: (i) R$_1$NC, R$_3$CO$_2$H, solvent; (ii) removal of protecting group (PG); (iii) acyl migration; (iv) optional side chain deprotection; (v) oxidation; (vi) semicarbazone formation; (vii) optional side chain deprotection; (viii) optional further chemistry; and (ix) deblocking of side-chain groups, deblocking of semicarbazone.

FIG. 8/Scheme 6 depicts the conversion of a generic ketoamide (8-5) to the semicarbazone derivative (8-6), and removal of the semicarbazone protecting group by selective cleavage via an exchange process to produce the final elaborated target ketoamide derivative (8-7). Conversion of ketoamide (8-5) to semicarbazone derivative (8-6) is carried out under classical conditions by condensation with the appropriate semicarbazide (diphenylmethylsemicarbazide) derivative in the presence of an aqueous alcoholic solvent combination over a concentration range of 0.001M to 0.25M, typically concentrations of about 0.01M to 0.1M are used. Preferably, a mildly basic inorganic salt, such as sodium acetate, is added to maintain a reaction pH of about 6 to about 9. The reaction is routinely performed at about ambient temperature to reflux, preferably at about refluxing temperature of about 70° C. to about 100° C. to afford the semicarbazone derivative (8-6).

The intermediate (8-6) is versatile and can be subjected to a variety of further chemistries. Optional side chain deprotection and selective synthetic manipulations of the newly exposed functionality is possible. For example, the $R_3X_1$- group of 8-6 may be removed and a different $R_3$-group coupled in its place to give the corresponding semicarbazone derivative 8-6, cleavage of the semicarbazone group gives the α-ketoamide 8-7.

In TFA Method IV and Complex Method III, a semicarbazide with the formula $H_2NNHCONHQ$, wherein Q is hydrogen, alkyl, aryl or aralkyl is suitable. Preferred semicarbazides are diphenylmethyl semicarbazide and simple semicarbazide. Preferred alcohols for use in step (a) are methanol, ethanol, and isopropanol. Especially preferred reaction conditions are, combining in (a), the product of TFA Method III or Complex Method II, respectively, with either i) diphenylmethyl semicarbazide, $NaOAc.3H_2O$, EtOH, and $H_2O$, or ii) semicarbazide with methanol and pyridine.

In TFA Method IV' and Complex Method III' the semicarbazone protecting group is selectively cleaved via an exchange process to produce the final elaborated target ketoamide derivative (8-7) (for Complex Method III'). Suitable reagents for the exchange/deprotection step include conditions selected from the group consisting of:

(i) 12N HCl, acetone, water, DCM (2:1:1:1);

(ii) 12N HCl, water, acetone, pyruvic acid (4:3:2:2);

(iii) 6N HCl, 2,4-pentanedione, DCM, acetone (3:1:1:1);

(iv) 12N HCl, water, 2,4-pentanedione, DCM, acetone (4:3:2:2:2);

(v) TFA, water, DCM, 2,4-pentanedione (9:1:2:2);

(vi) 12N HCl, water, methyl pyruvate, acetone (4:3:2:2); and (vii) TFA, water, DCM, pyruvic acid (9:1:2:2).

The exchange occurs over the temperature range of about −10° C. to about 60° C., preferably at about 20° C. to about 30° C. and over a time period of about 30 minutes to about 20 hours, typically about 6 to about 8 hours.

Examples 5, 7, and 8 describe semicarbazone protection and deprotection of ketoamide made using the TFA reactions. The teachings of those examples, as well as that available in the art, is applied to practice semicarbazone protection and deprotection of ketoamides made using the Complex reactions (Complex Methods III and III').

8. General Reaction Conditions

Reaction progress is routinely monitored by conventional analytical techniques such as RP-HPLC or TLC analysis (silica gel; UV, PMA visualization; EtOAc, hexane; ether, hexane, dichloromethane, hexane; dichloromethane, ethyl acetate mixtures); dichloromethane, methanol mixtures; dichloromethane, isopropanol mixtures.

9. Preferred Selections of $R_1$, $R_2$, and $R_3$

Methods of the present invention are preferably used to synthesize inhibitors of serine proteases and inhibitors of cysteine proteases. Preferred inhibitors are those that target thrombin, Factor Xa, NS3 protease of Hepatitis C Virus, calpain, and aspartyl protease.

Accordingly, certain preferred selections are set forth in Table I:

TABLE I

Preferred Compounds of Formula (CII)

| Inhibitor Type | —$NHR_1$ | $R_2$ | $R_3C(O)$— |
|---|---|---|---|
| Thrombin Inhibitor (Serine Protease) | phenethylamide | Arg side chain | Pro |
| Factor Xa (Serine Protease) | phenethylamide | Arg side chain | Pro,Gly |
| Calpain (Cysteine Protease) | $NHCH_2CH_3$ | Hydrophobic groups | Leu |
| HIV Enzyme (Aspartyl Protease) | NHPhe | Phe side chain | Val |

A composition comprising a compound made by the methods of the present invention can be a peptide or a peptide mimetic. Preferred uses for compositions made by the methods of the present invention are pharmaceutical or therapeutic agents, such as enzyme inhibitors, research tools, such as members of a combinatorial chemical library or ligands on an affinity column useful for purification. Preferred compositions are peptide inhibitors of serine proteases or cysteine proteases. Preferred inhibitors of serine proteases are those that inhibit thrombin. Factor Xa, or the NS3 protease of the Hepatitis C virus. A preferred inhibitor of a cysteine protease is a calpain inhibitor. A preferred inhibitor of an aspartyl protease is an HIV enzyme inhibitor.

Compositions comprising or incorporating compounds made by the methods of the present invention include solid supports. Preferred are solid supports such as Merrifield resin, PAM and MBHA resins. Especially preferred in this regard are solid supports used in the synthesis of peptides, or solid supports used to make combinatorial chemical libraries incorporating a compound made by a method of the present invention.

B. Comments Pertaining More Particularly to TFA Reactions

In TFA Method I, the α-hydroxy β-protected aminoamide derivative is preferably purified by a method selected from the group consisting of basic and acidic aqueous extraction, chromatography, and recrystallization. Especially preferred is aqueous extraction. In the event aqueous extraction does not yield product at the desired level of purity, then column chromatography is preferred. Recrystallization is an additional method used to improve the purity of product. The reaction is preferably performed at room temperature for 24 hours.

C. Comments Pertaining to Complex Methods

1. Complex Method I

In one embodiment, step (a) of Complex Method I also includes a mild organic base.

Typically, a reaction is initiated at about 0° C. and after about 0.5 to about 2 hours, the ice bath is removed and the reaction is stirred at ambient temperature. In cases where the aldehyde component is of intrinsically lower reactivity, the reaction is allowed to stir uncapped at ambient temperature for about 1 to about 8 days so as to allow for slow evaporation of solvent. The reaction is worked-up via extractive procedures and the crude residue preferably is purified by flash column chromatography on silica gel eluting with gradient systems of ethyl acetate, hexane; dichloromethane, ethyl acetate; dichloromethane, methanol; dichloromethane, ethanol or dichloromethane, isopropanol mixtures.

This reaction method delivers adducts in moderate to high overall yields. Since all of the atoms of the individual starting materials are retained in the adduct, such reactions are considered as examples of an efficient "atom economical" process. For example, pure product is obtained in the yields indicated in Table III as colorless to yellow foams. The 19 adducts in Table III embrace a broad range of structural variety and functionality.

Reactant concentrations are oftentimes important in determining not only the reaction rate but also the yield and quality of the desired adduct 8-2 (see FIG. 8/Scheme 6). A range of reactant concentrations from about 0.05 to about 0.5M, typically about 0.25M, are preferred for this process.

The next step entails removal of the α-amino protecting group. When PG is Cbz, removal is effected by treatment of the substrate 8-2 with hydrogen gas in the presence of a catalyst, such as Palladium on charcoal in a suitable inert solvent including methanol, ethanol, ethyl acetate or tetrahydrofuran. Under the conditions of this reaction, the intermediate α-acyloxy-β-aminoamide 8-3 is generated as the free base form and thus may spontaneously undergo the desired acyl migration in situ to provide the desired adduct 8-4.

If isolation of the intermediate 8-3 is desired under these conditions, then an appropriate mineral acid such as hydrochloric acid, sulfuric acid or the like is added to the solution before initiation of the reaction so as to trap the amine in the form of the corresponding salt. The salt form of 8-3 is stable and will not undergo the acyl migration unless a basic reagent is subsequently added to regenerate the free amino intermediate.

In those cases where the α-amino protecting group is Boc, an acidic reagent is employed for deblocking. Treatment of adduct 8-2 with a suitable strong acid reagent such as trifluoroacetic acid, optionally in the presence of an inert solvent such as dichloromethane at about −20° C. to about 30° C. provides the stable trifluoroacetate salt of 8-3. Alternatively, treatment of adduct 8-2 with a suitable acidic reagent such as hydrogen chloride, optionally in the presence of an inert solvent such as methanol, ethanol, dichloromethane, dioxane, tetrahydrofuran, or ethyl acetate at about −20° C. to about 30° C. provides the stable hydrochloride salt of 8-3.

When the α-amino protecting group is Fmoc, a basic organic reagent is usually employed for deblocking. Thus, treatment of adduct 8-2 with a suitable secondary amine reagent such as diethylamine or piperidine usually in the presence of an inert solvent such as dichloromethane, acetonitrile, dioxane, tetrahydrofuran, or ethyl acetate at about −20° C. to about 30° C. provides the free amine 8-3. Under these conditions or after additional reaction time (typically about 2 to 120 hours) the intermediate free base α-acyloxy-β-amino amide 8-3 may undergo an acyl migration in situ to provide the adduct 8-4.

If isolation of the intermediate 8-3 is desired under these conditions, then, as before, an appropriate mineral acid such as hydrochloric acid, sulfuric acid or the like is added to the reaction solution so as to trap the amine in the form of the corresponding salt. In this case, the mineral acid must be added after complete removal of the Fmoc protecting group.

In cases where the α-amino protecting group is Alloc, a reagent system featuring an organopalladium catalyst such as tetrakis(triphenylphosphine)palladium is employed for the deblocking procedure. The palladium reagent initially complexes with the protecting group and cleaves off the allyl group to form a π-allyl palladium species. The resultant intermediate immediately decarboxylates to form the amine 8-3. The π-allyl palladium complex reacts with a suitable acceptor species such as morpholine, piperidine or dimedone to transfer the allyl moiety which then terminates the deblocking process and affords the intermediate 8-3.

Under these conditions or after additional reaction time (typically about 2 to about 120 hours) the intermediate free base α-acyloxy-β-aminoamide 8-3 may undergo an acyl migration in situ to provide the adduct 8-4. If isolation of the intermediate 8-3 is desired under these conditions, then an appropriate mineral acid such as hydrochloric acid, sulfuric acid or the like is added to the reaction solution so as to trap the amine in the form of the corresponding salt. In this case, the mineral acid must be added after complete removal of the Alloc protecting group. The reaction is conducted in an inert solvent such as dichloromethane, acetonitrile, dioxane, tetrahydrofuran, or ethyl acetate at about −20° C. to about 30° C., preferably at about 20° C. to about 30° C. If the reaction is not performed in the presence of such mineral acids, the intermediate α-acyloxy-β-aminoamide 8-3 may undergo acyl migration in situ or upon solvent evaporation to provide the desired adduct 8-4.

The intermediate 8-3 or its salt forms are prepared as described above. Intermediate 8-3 generated in situ as the free base from deprotection of the Cbz Fmoc, or Alloc-precursors may undergo partial acyl migration during the course of the reaction or upon concentration of the reaction solution. By virtue of the reagents employed, deprotection of the Boc-derivatives lead directly to the hydrochloride or trifluoroacetate salt forms. These salt derivatives are relatively stable and can be stored for prolonged periods and will only undergo migration after the pH is adjusted to 7. The key acyl migration of intermediate 8-3 to 8-4 can be performed most efficiently over the pH range of about 7 to about 10, preferably at pH~8 to 9 over the temperature range of about −20° C. to about 50° C., preferably from about 0° C. to ambient temperature.

For salt forms of 8-3, the intermediate is dissolved in an appropriate solvent such as methanol, ethanol, water, acetonitrile, N,N-dimethylformamide, dichloromethane, dioxane, tetrahydrofuran, ethyl acetate, or combinations thereof, cooled to about 0° C., and the pH is adjusted as described above. The reaction is stirred at ambient temperature for about 1 to about 120 hours, progress being monitored by tlc, RP-HPLC and ninhydrin color analysis, and worked up after completion of the migration. As discussed above, in those cases where the free amine form of 8-3 is generated in situ by deprotection of a Cbz- or Fmoc-, or Alloc- precursor, the migration reaction may occur spontaneously to produce 8-4. Suitable bases include alkali metal hydroxides, dialkyl amines, trialkylamines and pyridine derivatives.

With the α-hydroxy-β-acylamide intermediate 8-4 in hand, optional side chain deprotection and selective synthetic manipulations of the newly exposed functionality is possible.

2. Complex Method II

In Complex Method II, oxidation of the secondary hydroxyl group to the ketoamide 8-5 is readily effected employing a range of mild oxidation conditions noted above and in the Examples.

A range of suitable inert solvents may be used, including those noted above, in the temperature range of about −78° C. to about 50° C.

3. Complex Method III

Conversion of the generic ketoamide 8-5 to the semicarbazone derivative 8-6 is carried out under classical conditions by condensation with the appropriate semicarbazide derivative in the presence of an aqueous alcohol solvent as described previously.

4. Complex Method III'

Finally, the semicarbazone protecting group is selectively cleaved via an exchange process to produce the final elaborated target ketoamide derivative 8-7. Suitable reagents and conditions for the exchange/deprotection step are those described previously.

5. Complex Method V

In Complex Method V, the step (b) hydrolysis is preferably performed with an alkali metal alkoxide; preferred alkoxides include lithium or sodium alkoxide. Methanol or ethanol are preferred reagents in this step, as well.

To assist in understanding the present invention, the following Examples are included which describe the results of several experiments. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

EXAMPLE 1

Synthesis of Protected Amino Acid Starting Materials Used in Methods TFA-I, Complex I, and Complex V Protected amino acid derivatives are converted into protected α-aminoaldehyde derivatives following the procedures outlined below and those employing procedures known in the art. Starting materials within the noted structural formulas are commercially available and/or may be synthesized using conventional methods. In each case, the noted protocol yields a protected α-aminoaldehyde derivative that may be used in either or both the TFA and Complex reactions, for which examples are provided herein below.

α-Aminoaldehydes primarily are obtained from α-amino acids. The synthetic route for these compounds usually proceeds via esters or active amides of α-amino acids, which are then reduced. A second approach is based on α-amino alcohols obtained from α-amino acids, which are oxidized to afford the desired α-amino aldehydes. Detailed summaries of reductive and oxidative procedures are listed in Chem. Rev. 89:149–164 (1989). Below are described some of the more commonly used methods.

A. Reductive Methods

1. Formation and Reduction of Active Amides

The preparation of PG-α-aminoaldehydes is based on reduction of N-methoxy-N-methyl carboxamides with lithium aluminum hydride (See, J-A Fehrentz and B. Castro, *Synthesis* page 676 (1983). FIG. 9A provides a reaction scheme for the reactions employing reagents i through iii, wherein i through iii are defined as: i) EDC, HOBt, MeO(Me)NH, NMM, 25° C. or IBCF, NMM, THF, −5° C., followed by MeO(Me)NH, −5° C. to RT; ii) LiAlH$_4$, THF, −40 C.; and iii) H$^+$.

Figure 10A:
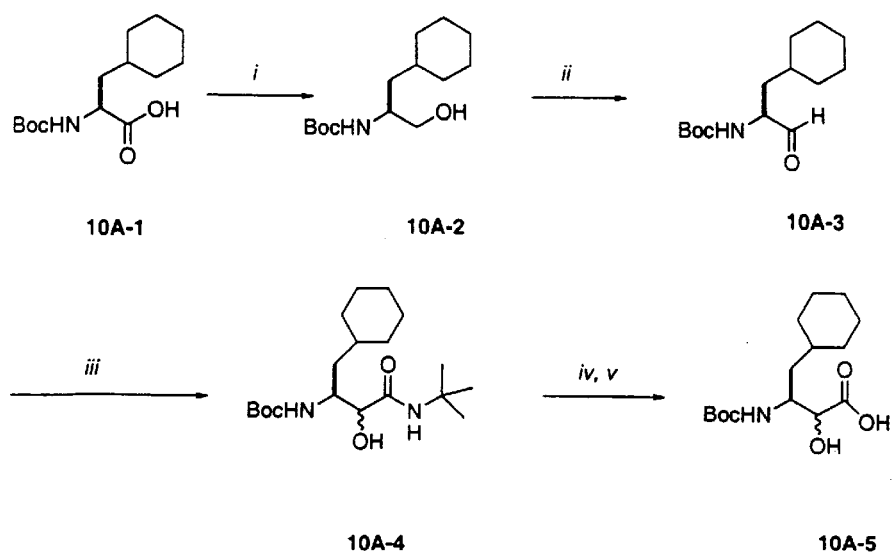
Figure 10B:
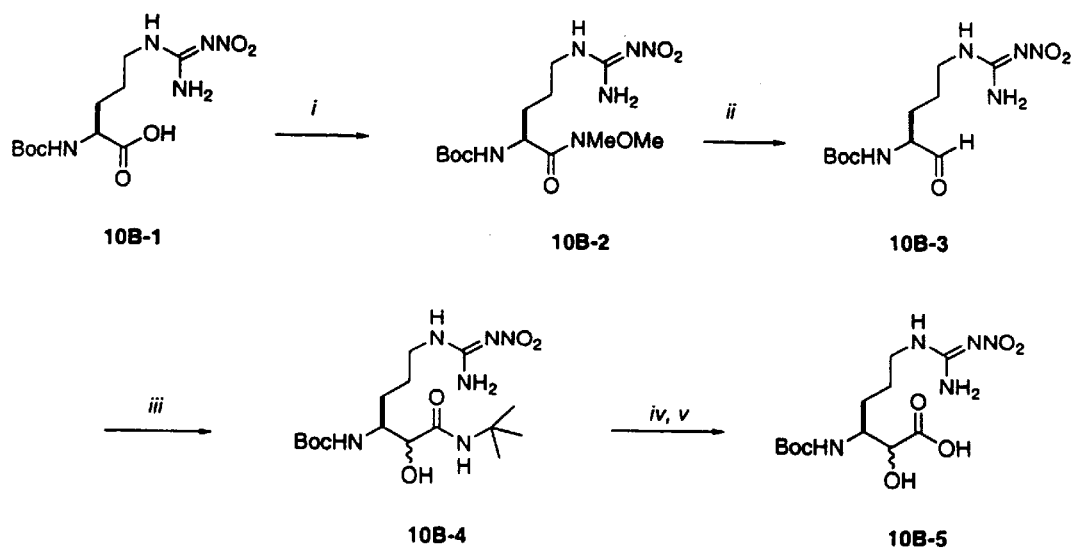
FIG. 10B depicts the synthesis of a protected arginine aldehyde (10B-3) described in Example 1a, and its use to synthesize α-hydroxy-β-amino(tert-butyloxycarbonyl) (nitro) homoarginine (10B-5b) described in Example 6b.

FIG. 10B depicts the synthesis of protected arginine aldehydes 10B-3, which result from the procedure described below.

To a solution of commercially available Boc-Arg(NO$_2$)—OH 10B-1 (5 g, 15.7 mmol) in acetonitrile (62 ml) was added successively, N,O-dimethylhydroxylamine hydrochloride (2 g, 20.4 mmol) and N-hydroxybenzotriazole (2.76 g, 18.1 mmol). The reaction flask was cooled to 0° C, and EDC.HCl (3.31 g, 17.3 mmol) and N-methylmorpholine (2.24 ml, 20.41 mmol) were added. After 15 minutes, the bath was removed and the reaction was allowed to proceed overnight at room temperature. The acetonitrile was removed under reduced pressure and the remaining residue was dissolved in ethyl acetate and washed with three 50 ml portions of water, 1N saturated sodium bisulfate, saturated sodium bicarbonate and brine. The organic layer was concentrated to yield a white foam (3.87 mg, 68%). TLC (silica gel, ethyl acetate) (R$_f$=0.37) confirmed the presence of only one spot. The product N$^α$-tert-butyloxycarbonyl-arginine (nitro) N-methyl O-methyl carboxamide 10B-2 was used in the next step without further purification. NMR δ ppm (CDCl$_3$): 5.65 (d, 1H), 4.7 (t, 1H), 3.8 (s, 3H), 3.6 (m, 1H), 3.3 (m, 1H), 3.2 (s, 3H), 1.7–1.8 (m, 3H), 1.6–1.7 (m, 1H), 1.4 (s, 9H).

A solution of 1M LAH in THF (70 ml) in a three neck round bottom flask equipped with a thermometer, under N$_2$ was cooled to −78° C. with a dry ice/acetone bath. A solution of 10B-2 (3.8 g, 10.5 mmol) in 30 ml THF was added via a canula to the first flask, dropwise. The reaction mixture was stirred at −78° C. for 20 minutes and then slowly brought to 0° C. and stirred an additional 40 minutes at 0° C. The reaction mixture was cooled down with a dry ice/acetone bath and quenched by the dropwise addition of 1N NaHSO4 until all bubbling had stopped. The reaction mixture was then diluted with ethyl acetate (50 ml) and extracted twice with a 1N NaHSO$_4$ (20 ml each) solution. The organic layer was dried over sodium sulfate and concentrated under reduced pressure. The crude yellow solid obtained N$^α$-tert-butyloxycarbonyl-arginine (nitro) aldehyde 10B-3 (2.27 g, 71.4%) was used in the next step (see Example 6b) without further purification.

2. Formation of PG-α-Aminoesters and Reduction to PG-α-Aminoaldehydes

Reference: (*Chem. Pharm. Bull.* 23:3081–3087 (1975)). FIG. 9B depicts a reaction scheme for the reactions employing the reagents i through iii which are defined as follows: i) SOCl$_2$, MeOH; ii) (i-Bu)$_2$AlH (DIBALH), n-hexane, toluene, −50° C.; and iii) H+.

3. Synthesis of Chiral N-Protected α-Amino Aldehydes by Reduction of N-Protected N-Carboxy Anhydrides References: (*Tet. Lett.* 35:9031–9034 (1994); and *J. Am. Chem. Soc.* 112:7414–7416 (1990)).

FIG. 9C depicts a reaction scheme for reactions employing the reagents i and ii which are defined as follows: i) LTEPA (lithium tris[(3-ethyl-3-pentyl)oxy]aluminum hydride) or Li(OtBu)$_3$AlH, THF, −5° C.; and ii) H+.

4. Synthesis of Chiral N-Protected α-Amino Aldehydes by Triethylsilane Reductive Reaction of N-Fmoc-Protected α-Aminothioesters References: (*J. Org. Chem.* 58:2313–2316 (1993); and *J. Am. Chem. Soc.* 112:7050–7051 (1990)).

FIG. 9D depicts a reaction scheme for reactions employing the reagents i and ii which are defined as: i) BnSH (or EtSH), DCC, THF; and ii) Et$_3$SiH, Pd/C, acetone.

5. Synthesis of Chiral N-Protected α-Amino Aldehydes by Reduction of Corresponding Acid Halides References: (*Tetrahedron Lett.* 36:7281–7284 (1995)).

FIG. 9E depicts a reaction scheme for reactions employing the reagents i through iii which are defined as follows: i) $SOCl_2$, DCM, RT; ii) $LiAlH(OtBu)_3$, THF, −78° C., 20 minutes; and iii) H+.

B. Oxidative Methods

These methods are based on the oxidation of α-amino alcohols, e.g., by use of any one of the Von Doering, Moffatt, Swern or Dess-Martin periodinane oxidation procedures. The N-protected α-amino alcohols can be obtained by borane-tetrahydrofuran reduction of N-protected α-amino acids or by sodium borohydride-lithium chloride and sodium borohydride-calcium chloride reduction of the corresponding methyl esters. The synthesis of N-protected α-amino alcohol intermediate (step I), and its oxidation to the α-amino aldehyde (step II), is discussed below:

1. Step I: Synthesis of N-Protected α-Amino Alcohol Intermediate a. Borane-Tetrahydrofuran Reduction of N-Protected α-Amino Acids Reference: (J. Org. Chem. 46:4799 (1981)).

FIG. 9F depicts a general reaction scheme for these reactions. FIG. 10A depicts a reaction scheme for the synthesis of 10A-2, Nα-tert-butyloxy-carbonyl-cyclohexylalaninol.

To a solution of tert-butyloxycarbonyl-cyclohexyl alanine.DCHA salt (10.57 g, 23.35 mmol) in 200 ml methanol and 50 ml water was added enough Dowex (50 X8-400) ion exchange resin to obtain an acidic solution, pH~3, as judged by pH paper. After stirring for half an hour, the resin was removed by filtration. The filtrate was concentrated and dried in vacuo to obtain a clear oil 10A-1, (6.31 g, 99.6%). Thin layer chromatography in 9:1 dichloromethane:methanol gave only one spot ($R_f$=0.35).

To a chilled solution of 10A-1 (6.31 g, 23.25 mmol) in tetrahydrofuran (93 ml) was added diborane.tetrahydrofuran complex (1M solution in THF, 93 ml, 93.0 mmol). The reaction proceeded for 10 minutes at 0° C., followed by 90 minutes at room temperature. The reaction was quenched by the dropwise addition of 1N sodium bisulfate (5 ml) at 0° C. The reaction mixture was then diluted with ethyl acetate and washed twice with 20 ml portions of water and brine. The organic layer was dried and concentrated to a clear oil (5.46 g, 91.3%). Thin layer chromatography in 9:1 dichloromethane:methanol gave only one spot ($R_f$=0.69). NMR δ ppm ($CDCl_3$): 4.5 (bs, 1H), 3.8 (bs, 1H), 3.7 (dd, 1H), 3.5 (dd, 1H), 2.4 (bs, 1H), 1.6–1.8 (m, 5H), 1.4 (s, 9H), 1.1–1.3 (m, 5H), 0.8–1.0 (m, 3H).

b. Reduction Of N-Protected α-Amino Acid Methyl Esters By Sodium Borohydride-Lithium Chloride And Sodium Borohydride-Calcium Chloride References: (*Tetrahedron Lett.* 23:1193 (1982)) (*J. Org. Chem.* 52:1487 (1987)).

FIG. 9G depicts a general reaction scheme for these reactions employing the reagents i and ii which are defined as: i) $SOCl_2$, MeOH; and ii) $NaBH_4$, $CaCl_2$ (or LiCl), MeOH, THF.

Figure 11:
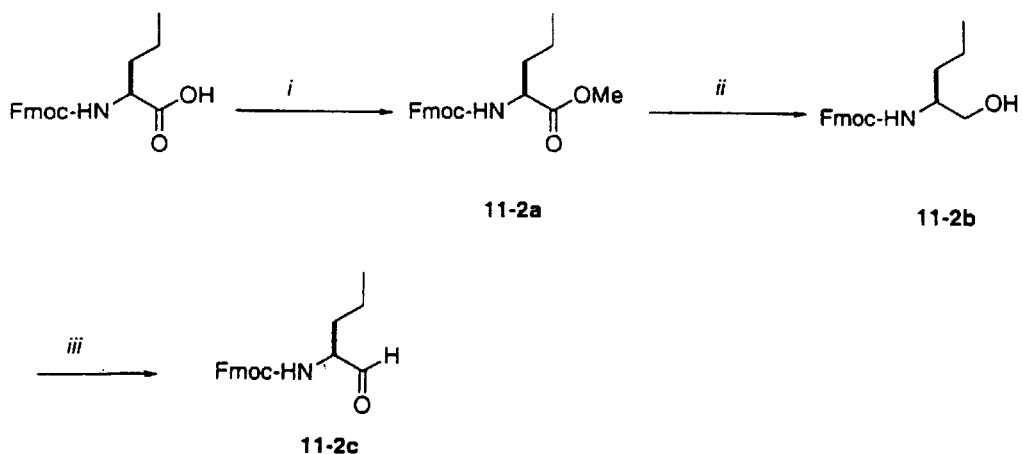
FIG. 11 depicts the synthesis of a protected norvaline aldehyde (11-2c) described in Example 1b. In this figure, (i) through (iii) are defined as follows: (i) SOCl$_2$, MeOH (anhydrous); (ii) CaCl$_2$, NaBH$_4$, MeOH, THF; and (iii) pyridine.SO$_3$, DMSO, DCM, TEA.

FIG. 11 depicts a reaction scheme for the synthesis of 11-2b, 9-fluorenylmethoxy-carbonyl-norvalinol, a description of the synthesis of which follows. To a chilled solution of Fmoc-norvaline (25 g, 73.75 mmol) in anhydrous methanol (469 ml), was added thionyl chloride (53.76 ml, 737.5 mmol) over one hour. Thin layer chromatography in ethyl acetate after an hour confirmed the completion of the reaction ($R_f$=0.85). The reaction mixture was concentrated and the remaining residue was dissolved in ethyl acetate. The organic layer was washed with several 200 ml portions of saturated sodium bicarbonate followed by brine. The organic layer was dried and concentrated to afford the title compound 9-fluorenylmethoxy-carbonyl-norvaline methyl ester 11-2a as a white solid (26.03 g) in quantitative yield. NMR δ ppm ($CD_3OD$): 7.7 (m, 2H), 7.6 (m, 2H), 7.4 (m, 2H), 7.3 (m, 2H), 4.3 (m, 2H), 4.1 (m, 2H), 3.7 (s, 3H), 1.7 (m, 1H), 1.6 (m, 1H), 1.4 (m, 2H), 0.95 (t, 3H).

To the product 11-2a of the previous step (26.03 g, 73.75 mmol) in THF (123 ml) and methanol (246 ml) was added calcium chloride (16.37 g, 147.49 mmol). The reaction mixture was cooled to 0° C. and sodium borohydride (11.16 g, 294.98 mmol) was added in several portions. To the thick paste obtained, 500 ml methanol was added and the reaction was allowed to stir at room temperature for 90 minutes. Thin layer chromatography in 2:3 ethyl acetate:hexane confirmed the completion of the reaction ($R_f$=0.25). The reaction was quenched with the slow addition of 100 ml water at 0° C. The methanol was removed under reduced pressure and the remaining aqueous phase was diluted with ethyl acetate. The organic layer was washed three times each with 500 ml portions of water, saturated sodium bicarbonate and brine. The organic layer was dried over sodium sulfate and concentrated to a white solid, 9-fluorenylmethoxy-carbonyl-norvalinol 11-2b (21.70 g, 90.5%). NMR δ ppm (CD3OD): 7.8 (m, 2H), 7.7 (m, 2H), 7.4 (m, 2H), 7.3 (m, 2H), 4.3–4.5 (m, 2H), 4.2 (m, 1H), 3.6 (s, 1H), 3.5 (s, 2H), 1.5 (m, 1H), 1.3–1.4 (m, 3H), 0.99 (m, 3H).

2. Step II: Oxidation of N-protected α-Amino Alcohol (Intermediate Obtained in Step I) to N-Protected α-Amino Aldehyde a. von-Doering Oxidation Reagents used are: $Pyr.SO_3$, DMSO, TEA References: (J. Am. Chem. Soc. 89:5505 (1967); *Chem. Pharm. Bull* 30:1921–1924 (1982); *J. Org. Chem.* 51: 3921–3926 (1986); and *J. Org. Chem.* 45:1864 (1980)).

FIG. 9H depicts a general reaction scheme for reactions of this type. FIG. 10A depicts a reaction scheme for synthesis of (10A-3), N-α-tert-butyloxycarbonyl-cyclohexylalaninal, by the von-Doering oxidation, as outlined below in (a). FIG. 11 provides a scheme for synthesis of 11-2c, 9-fluorenylmethoxy-carbonyl-norvalinal, by the von-Doering oxidation.

i. Synthesis of N-α-tert-Butyloxy-Carbonyl-Cyclohexylalaninal by the von-Doering Oxidation 10A-3

To the α-amino alcohol 10A-2 (see FIG. 10A) (5.46 g, 21.22 mmol) in anhydrous dichloromethane (194 ml) was added triethylamine (17.74 ml, 127.29 mmol); the resulting solution was cooled to 0° C. A suspension of pyridine sulfur trioxide complex (20.26 g, 127.3 mmol) in anhydrous dimethylsulfoxide (32 ml) was added to the chilled solution. After 90 minutes, TLC in 1:1 ethyl acetate:hexane confirmed the completion of the reaction. The dichloromethane was removed under reduced pressure and the remaining residue was dissolved in ethyl acetate and washed twice with several 50 ml portions of water, 1N saturated sodium bisulfate, saturated sodium bicarbonate and brine. The organic layer was concentrated to yield a white solid. Theoretical yield (5.42 g) was assumed and the product was used in the next synthesis step (see Example 3) without further purification.

ii. Synthesis of 9-Fluorenylmethoxy-Carbonyl-Norvalinal by the von-Doering Oxidation 11-2c To the α-amino alcohol 11-2b (21.70 g, 66.8 mmol) in dichloromethane (668 ml) was added triethylamine (37.23 ml, 267.1 mmol) and the solution was cooled to 0° C. A suspension of pyridine sulfur trioxide complex (42.51 g, 267.1 mmol) in dimethylsulfoxide (96 ml) was added to the chilled solution. After one hour, TLC in 2:3 ethyl acetate- :hexane confirmed completion of the reaction. The dichloromethane was removed under reduced pressure and the remaining residue was dissolved in ethyl acetate and washed with several 50 ml portions of water, 1N saturated sodium bisulfate, saturated sodium bicarbonate and brine. The organic layer was concentrated to yield a white solid. Theoretical yield (21.57 g) was assumed and the reaction was taken to the next step without further purification.

b. Moffatt Oxidation

Reagents used are EDC, DCA, DMSO, toluene, and 0° C. to RT. (Reference: *J. Am. Chem. Soc.* 110:7217–7218 (1988)).

FIG. 9H depicts a general reaction scheme for reactions of this kind.

c. Swern Oxidation

Reagents used are: oxalyl chloride, DMSO, DCM, and −60° C. (References: *J. Org. Chem.*, 43: . . . (1978); *Org. Prep. and Proced. Int.* 25:437–443 (1993)). FIG. 9H depicts a general reaction scheme for reactions of this kind.

d. Dess-Martin Periodinane Oxidation

Reagents used are: Dess Martin reagent, and DCM at RT. (Reference: *J. Am. Chem. Soc.* 113:7277–7287 (1991)). FIG. 9H depicts a general reaction scheme for reactions of this kind.

EXAMPLE 2

Synthesis of Allyl Isocyanoacetate

Figure 12:
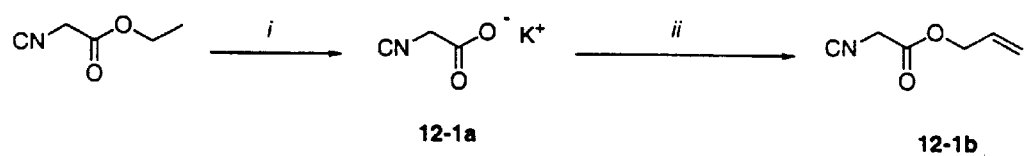
FIG. 12 depicts the synthesis scheme for alkyl isocyanoacetate described in Example 2. In this figure, (i) and (ii) are defined as follows: (i) KOH, ethanol; and (ii) allyl bromide, acetonitrile, heating.

The compound synthesized according to this Example is an isonitrile reagent that can be used in both the TFA and Complex Methods, for which Examples are provided hereinbelow. The synthesis scheme is depicted in FIG. 12.

Ethyl isocyanoacetate (96.6 ml, 0.88 mol) was added dropwise to a chilled solution of ethanol (1.5 L) and potassium hydroxide (59.52 g, 1.06 mol). The reaction mixture was slowly warmed to room temperature. After two hours the precipitated product was filtered on a glass funnel and washed with several portions of chilled ethanol. The potassium salt of isocyanoacetic acid thus obtained was dried in vacuo to a golden-brown solid (99.92 g, 91.8%).

To the product of the previous step (99.92 g, 0.81 mol) dissolved in acetonitrile (810 ml), was added allyl bromide (92 ml, 1.05 mol). After refluxing for four hours a dark brown solution was obtained. The reaction mixture was concentrated and the remaining residue was dissolved in ether (1.5 L) and washed three times with water (500 ml). The organic layer was dried and concentrated to a dark brown syrup. The crude product was purified by vacuum distillation at 7 mm Hg (98° C.) to a clear oil (78.92 g, 77.7%). NMR δ ppm (CDCl$_3$): 5.9 (m, 1 H), 5.3 (m, 2H), 4.7 (d, 2H), 4.25 (s, 2H).

EXAMPLE 3

General Protocol for Formation of α-Hydroxy-β-Protected Amino Acid Derivatives (Passerini Adduct) from Protected α-Aminoaldehyde Derivatives (TFA Method I)

The general procedure detailed below, and depicted in FIG. 6/Scheme 4, comprises oxidizing [O] a protected α-amino alcohol (made pursuant to Example 1 or other methods), and then combining the resulting α-aminoaldehyde with an isonitrile (e.g., allyl isocyanoacetate from Example 2, t-butyl isocyanide), trifluoroacetic acid, a mild organic base (e.g., pyridine), and an inert organic solvent (e.g. dichloromethane) at a temperature between 0° C. and 40° C.

Trifluoroacetic acid (2 eq) was added dropwise to a cooled solution (0° C.) of the crude protected α-aminoaldehyde formed after oxidation (1 eq; see Example 1), allyl isocyanoacetate (1.2 eq; see Example 2), and pyridine (4 eq) in dichloromethane (0.25M to 0.5M). After 0.5 hour the bath was removed and the reaction was left to stir uncapped at ambient temperature for 12 to 48 hours. The thick yellow to brown slurry was dissolved in ethyl acetate and extracted successively three times each with 1N hydrochloric acid, saturated sodium bicarbonate and brine. The organic layer was dried over sodium sulfate and concentrated. The yellow to brown oil was purified by flash column chromatography in ethyl acetate/hexane or dichloromethane/methanol mixtures. Pure product was obtained in 60–87% yield as a white to yellow foam.

Table II depicts a representative variety of starting amino acids and their sidechains, α-amino PG, and isonitrile used to synthesize a variety of α-hydroxy-β-protected amino acid derivatives using the procedures of Examples 1 through 3. These compounds were synthesized using a mild base (such as pyridine) and an inert organic solvent (such as dichloromethane).

Figures 20A, 20B:
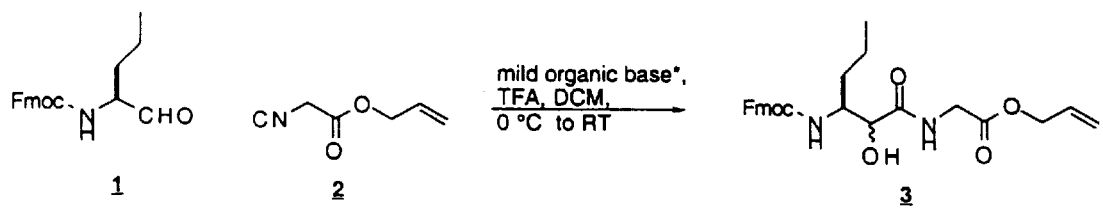
FIG. 20A depicts a reaction scheme for preparation of an α-hydroxy-β-protected amino acid derivative using the TFA scheme using Fmoc-norvaline aldehyde and allylisocyanoacetate in dichloromethane and utilizing a number of mild organic bases.
FIG. 20B gives the yield obtained for the respective mild organic bases.

In addition to pyridine, other mild organic bases may be used. Results observed by carrying out the TFA scheme of the present invention between Fmoc-norvaline aldehyde and allylisocyano-acetate in dichloromethane using other representative organized bases are summarized in FIG. 20. These results indicate that the more hindered analogs of pyridine such as 2,6-di-t-butyl-pyridine, 2,4,6-collidine and 2,6-lutidine give a higher yield of the desired product adduct 14-3 (see FIG. 14) and, accordingly, their use may be preferred over pyridine.

TABLE II

α-Hydroxy-β-Protected Amino Acid Derivatives of Formula TFA-I Prepared Using the TFA Procedure Described in Example 3 From α-Aminoaldehyde Derivatives[1]

| R$_1$ | R$_2$ (Amino Acid) | PG |
|---|---|---|
| —CH$_2$CO$_2$-allyl | H (Gly) | Fmoc |
| —CH$_2$CO$_2$-allyl | CH$_3$ (Ala) | Fmoc |
| —CH$_2$CO$_2$-allyl | —CH$_2$O-t-Bu (Ser(t-Bu)) | Fmoc |
| —CH$_2$CO$_2$—CH$_3$ | —CH(CH$_3$)$_2$ (Val) | Boc |
| —CH$_2$CO$_2$-t-Bu | —CH(CH$_3$)$_2$ (Val) | Fmoc |
| —CH$_2$CO$_2$—CH$_3$ | —CH(CH$_3$)$_2$ (Val) | Fmoc |
| —CH$_2$CO$_2$-allyl | —CH(CH$_3$)$_2$ (Val) | Fmoc |
| —CH$_2$CO$_2$-allyl | —(CH$_2$)$_2$CH$_3$ (norVal) | Fmoc |
| —CH$_2$CO$_2$—CH$_3$ | —(CH$_2$)$_2$CH$_3$ (norVal) | Boc |
| —CH$_2$CO$_2$-allyl | —CH$_2$CH(CH$_3$)$_2$ (Leu) | Fmoc |
| —CH$_2$CO$_2$-allyl | —CH$_2$-Phe (Phe) | Fmoc |
| —CH$_2$CO$_2$-allyl | —CH$_2$—Ph—O-t-Bu (Tyr(t-Bu)) | Fmoc |
| —CH$_2$CO$_2$—CH$_2$CH$_3$ | —CH$_2$—Ph—O-t-Bu (Tyr(t-Bu)) | Fmoc |
| —CH$_2$CO$_2$-allyl | —CH$_2$CO$_2$-t-Bu (Asp(t-Bu)) | Fmoc |
| —CH$_2$CO$_2$-allyl | —(CH$_2$)$_3$NHC(=NH)NH—PMC (Arg(Pmc)) | Fmoc |
| —CH$_2$CO$_2$—CH$_2$CH$_2$ | —(CH$_2$)$_3$NHC(=NH)NHNO$_2$ (Arg(NO$_2$)) | Fmoc |
| —CH$_2$CO$_2$-allyl | —(CH$_2$)$_3$NHC(=NH)NHNO$_2$ (Arg(NO$_2$)) | Boc |
| —CH$_2$CO$_2$-allyl | —(CH$_2$)$_4$NH(Boc) (Lys(Boc)) | Fmoc |

[1]These α-hydroxy-β-protected amino acid derivatives were synthesized using a mild base, such as pyridine, and an inert solvent, such as dichoromethane.

EXAMPLE 4

General Protocol for Formation of α-Hydroxy-β-Protected Aminoamide Derivatives (Passerini Adduct) from Protected α-Aminoaldehyde Derivatives (Complex Method I)

The general procedure described below, and shown in FIG. 7/Scheme 5, comprises oxidizing a protected α-amino alcohol (made pursuant to Example 1 or other methods), and then combining the resultant α-aminoaldehyde 7-1 with an isonitrile (e.g., allyl isocyanoacetate of Example 2), a carboxylic acid derivative (e.g., Alloc-Pro, $BnSO_2$-7Lac-Gly), an organic solvent (e.g. dichloromethane, methanol), and optionally a mild organic base (e.g., pyridine), at a temperature between 0° C. and 40° C. After removal of the α-amino PG and subsequent acyl group migration, the desired α-hydroxy-β-protected aminoamide derivative is formed.

The carboxylic acid ($R_3CO_2H$, 1–2 equiv.) was added to a solution of the protected α-aminoaldehyde (PGNHCH [$R_2$] CHO, 1 eq) and isonitrile derivative ($R_1$NC, 1.0–1.3 equiv.) at 0° C. in dichloromethane, ethanol, or methanol (0.05 to 0.5M concentration range, typically 0.25M). After about 0.5 to 2 hours, the ice bath was removed and the reaction was stirred at ambient temperature for about 1 to 8 days, progress being monitored by RP-HPLC or TLC analysis (silica gel; uv, PMA visualization; EtOAc, hexane; ether, hexane, dichloromethane, hexane; dichloromethane, ethyl acetare mixtures). Depending on the reactivity of the starting amino aldehyde, the reaction was allowed to stir uncapped at ambient temperature for about 1 to 8 days so as to allow for slow evaporation of solvent. The more reactive starting amino aldehydes required less time for reaction than the less reactive aldehydes. Solvent removal affords a thick yellow to brown slurry which was dissolved in ethyl acetate or dichloromethane, extracted successively three times each with 1N hydrochloric acid, saturated sodium bicarbonate and brine. The organic layer was dried over sodium or magnesium sulfate, filtered and concentrated. The crude residue was purified by flash column chromatography on silica gel eluting with gradient systems of ethyl acetate/hexane, dichloromethane/ethyl acetate, dichloromethane/methanol, dichloromethane/ethanol, or dichloromethane/isopropanol mixtures. Pure product was obtained in the yields indicated in Table III as a colorless to yellow foam.

The procedures of Examples 9 and 10 were followed to remove the protecting group, PG, and to effect acyl migration to form the new α-hydroxy-β-amino amide derivative. In general, these steps entail removal of the α-amino protecting group. The reagents and conditions use to effect removal depend on the nature of the protecting group to be removed, as described hereinabove. The resulting α-acyloxy-β-aminoamide intermediate, when obtained as a free base, undergoes acyl migration in situ to provide the desired α-hydroxy-β-amino amide derivative product. However, acyl migration is unlikely to occur when the α-acyloxy-β-amino amide is generated in its salt form, because such salt derivatives are relatively stable. In that case, acyl migration is effected by adjusting the reaction pH to about 8 to 9, and provides the desired α-hydroxy-β-amino amide derivative product.

Table III displays a representative variety of α-amino PG, $R_2$ amino acid side chains, $R_3$ carboxylic acid groups, $R_1$ isonitrile groups, and inert solvents used to synthesize a variety of α-hydroxy-β-protected aminoamide derivatives, with the stated yields, using the Complex Procedure described in this Example.

TABLE III

α-acyloxy-β-Protected Amino Acid Derivatives of Formula 7-3 (CIA) Prepared Using the Complex Method as Described in Example 4 From Protected α-Aminoaldehyde Derivatives

| Compound used to make | PG | $R_1$ | $R_2$ | —C(O)$R_2$ | Solvent | % Yield |
|---|---|---|---|---|---|---|
| | Boc | —$CH_2CO_2CH_2CH_3$ | (S)—$(CH_2)_3$NHC($NH_2$)=$NNO_2$ | Fmoc-Pro | EtOH | 51 |
| | Boc | —$CH_2CO_2CH_2CH_3$ | (S)—$(CH_2)_3$NHC($NH_2$)=$NNO_2$ | Alloc-Pro | EtOH | 50 |
| | Boc | —$CH_2CO_2CH_2CH_3$ | (S)—$(CH_2)_3$NHC($NH_2$)=$NNO_2$ | Ac | EtOH | 35 to 48 |
| | Boc | —$CH_2CO_2CH_2CH_3$ | (S)—$(CH_2)_3$NHC($NH_2$)=$NNO_2$ | Bz | EtOH | 57 |
| | Boc | —$CH_2CO_2CH_2CH_3$ | (S)—$(CH_2)_3$NHC($NH_2$)=$NNO_2$ | —C(O)$CH_2CH_2$Ph | EtOH | 60 to 62 |
| | Fmoc | —$CH_2CO_2CH_2CH_3$ | (S)—$(CH_2)_3$NHC($NH_2$)=$NNO_2$ | Ac | $CH_2Cl_2$ | 76 |
| [A][1] | Boc | Phe-Tyr($Cl_2$Bn)—OMe | (S)—$(CH_2)_3$NHC($NH_2$)=$NNO_2$ | Alloc-Pro | $CH_2Cl_2$ | 59 |
| [B][2] | Boc | —$CH_2CO_2CH_2CH_3$ | (S)—$(CH_2)_3$NHC($NH_2$)=$NNO_2$ | $BnSO_2$-7Lac-Gly | MeOH | 39 |
| [C][3] | Fmoc | PhEt | (S)—$(CH_2)_3$NHC($NH_2$)=$NNO_2$ | Ph(3-OMe)$SO_2$-Pdn-Gly | MeOH | 38 |
| | Fmoc | —$CH_2CO_2$t-Bu | (S)-i-Propyl | Ac | $CH_2Cl_2$ | 84 |
| | Fmoc | —$CH_2CO_2$t-Bu | (S)-i-Propyl | Formyl | $CH_2Cl_2$ | 50[4] |
| | Boc | —$CH_2CO_2CH_3$ | (S)-i-Propyl | Ac | $CH_2Cl_2$ | 66 |
| | Fmoc | Leu-OMe | (S)—Me | d-Boc-Orn(Z) | $CH_2Cl_2$ | 43 |
| [E][5] | Fmoc | Leu-O—Me | (S)—Me | 1-Boc-Orn(Z) | $CH_2Cl_2$ | 75–80 |
| | Cbz | —$CH_2CO_2CH_2CH_3$ | (S)—Bn | Bz | $CH_2Cl_2$ | 44 |
| | Fmoc | —$CH_2CO_2Ch_2CH_3$ | (S)—Bn | Bz | $CH_2Cl_2$ | 69 |
| | Boc | —$CH_2CO_2CH_2CH_3$ | (S)—Bn | Ac | $CH_2Cl_2$ | 67 |
| | Fmoc | —$CH_2CO_2CH_2CH_3$ | (S)—$(CH_2)_3$NHC($NH_2$)=$NNO_2$ | $BnSO_2$-d-Arg($NO_2$)-Sar | $CH_2Cl_2$ | 31[6] |
| [G][7] | Boc | —$CH_2CO_2$-allyl | (S)—$(CH_2)_3$NHYC($NH_2$)=$NNO_2$ | PrPent-Asp(OMe) Pro | $CH_2Cl_2$ | 83 |

Figure 19A:
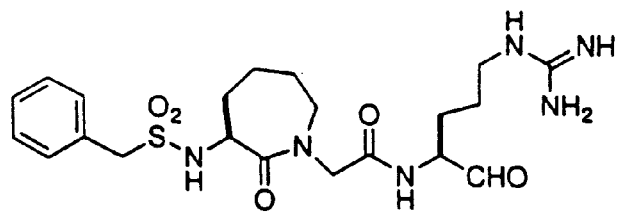
FIGS. 19A to 19D depict the structures of several compounds within Table 2.
Figure 19B:
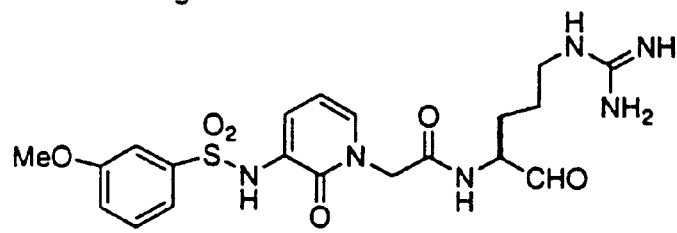
Figure 19C:
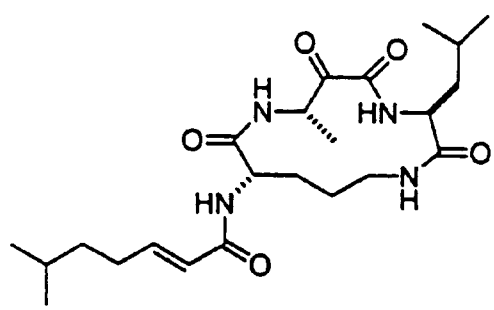
Figure 19D:
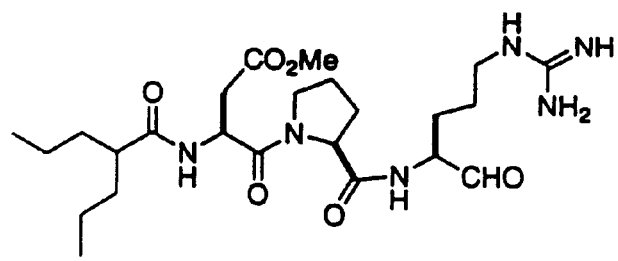

[1] cyclotheonamide intermediate (see Example 10, FIG. 17)
[2] a thrombin inhibitor (see FIG. 19A)
[3] Thrombin inhibitor (See FIG. 19B)
[4] $R_3$ is labile in MeOH
[5] Eurystatin intermediate (see FIG. 19C)
[6] $CH_2Cl_2$:EtOH about 3:1
[7] Thrombin inhibitor (see FIG. 19D)

Table IV displays an additional variety of starting amino acids and their sidechains ($R_2$ carbonyl), N-terminal protecting groups (PG), carboxylic acids ($R_3$), isonitriles ($R_1$), a mild organic base (pyridine), and inert organic solvent (dichloromethane) used to synthesize a variety of α-hydroxy-β-protected aminoamide derivatives using the procedure described in this Example. The intermediates of Table III and Table IV were used to make a variety of target protease inhibitors, as noted in the Tables.

concentrated. The theoretical yield was assumed and the oxidation adduct 13-1 was taken to the next step without further purification.

To the oxidation adduct 13-1 (1 eq) dissolved in a 3:1 mixture of ethanol and water (0.06 M) were added, successively, diphenylmethyl semicarbazide (2 eq) and sodium acetate.$3H_2O$ (1.2 eq). The reaction mixture was refluxed until the completion of reaction was confirmed by TLC. Ethanol was removed under reduced pressure and the

TABLE IV

α-Hydroxy-β-Protected Amino Acid Derivatives Prepared Using the Procedure Described in Example 4

A. Complex Method (Formula CIA)[1]

| PG | $R_1$ | $R_2$ (Amino Acid) | Carboxylic Acid ($R_3C(O)$—) |
|---|---|---|---|
| Boc | —$CH_2CO_2CH_3$ | —$CH(CH_3)_2$ (Val) | Ac |
| Fmoc | —$CH_2CO_2$-t-Bu | —$CH(CH_3)_2$ (Val) | Formyl |
| Fmoc | —$CH_2CO_2$-t-Bu | —$CH(CH_3)_2$ (Val) | Ac |
| Boc | —$Ch_2CO_2CH_3$ | —$(CH_2)_2CH_3$ (norVal) | Ac |
| Boc | —$CH_2CO_2CH_2CH_3$ | —$CH_2Ph$ (Phe) | Ac |
| Cbz | —$CH_2CO_2CH_2CH_3$ | —$CH_2Ph$ (Phe) | $PhCO_2H$ |
| Fmoc | —$CH_2CO_2CH_2CH_3$ | —$CH_2Ph$ (Phe) | $PhCO_2H$ |
| Fmoc | —$CH_2CO_2CH_2CH_3$ | 4-t-Bu$PhCH_2$-(Tyr(t-Bu)) | $BnSO_2$-d-Arg($NO_2$)-Sar |
| Fmoc | —$CH_2CO_2CH_2CH_3$ | —$(CH_2)_3NHC(=NH)NHPmc$ (Arg(Pmc)) | Ac |
| Boc | —$CH_2CO_2CH_2CH_3$ | —$(CH_2)_3NHC(=NH)NHNO_2$ (Arg ($NO_2$)) | Ac |
| Boc | —$CH_2CO_2CH_2CH_3$ | —$(CH_2)_3NHC(=NH)NHNO_2$ (Arg($NO_2$)) | Bz |
| Boc | —$CH_2CO_2CH_2CH_3$ | —$(CH_2)_3NHC(=NH)NHNO_2$ (Arg($NO_2$)) | $PhCH_2CH_2C(O)$— |
| Boc | —$CH_2CO_2CH_2CH_3$ | —$(CH_2)_3NH(=NH)NHNO_2$ (Arg($NO_2$)) | Alloc-Pro |
| Boc | —$CH_2CO_2CH_2CH_3$ | (($CH_2)_3NH(=NH)NHNO_2$ (Arg($NO_2$)) | Fmoc-Pro |
| Boc | —$CH_2CO_2CH_2CH_3$ | —$(CH_2)_3NH(=NH)NHNO_2$ (Arg($NO_2$)) | $BnSO_2$-norLeu (cyclo)-Gly |

[1]These α-acyloxy-β-protected amino acid derivatives may optionally be synthesized using a mild base, such as pyridine, in an organic solvent, such as dichloromethane

B. TFA Method (Formula TFA-I)[1]

| PG | $R_1$ | $R_2$ (Amino Acid) |
|---|---|---|
| Boc | —$CH_2CO_2$-allyl | —$Ch_2Ph$ (Phe) |
| Boc | —$CH_2CO_2CH_2CH_3$ | —$Ch_2Ph$ (Phe) |
| Boc | —H | —$CH_2Ph$ (Phe) |

[1]These α-hydroxy-β-protected amino acid derivatives were synthesized using a mild base, such as pyridine, and an organic solvent, such as dichloromethane

EXAMPLE 5

General Protocol for Synthesis of Semicarbazone Protected α-Ketoamide Derivatives using α-Hydroxy-β-Protected Amino Acid Derivatives from TFA Method of Example 3 (TFA Methods III, IV, and IV']

Figure 13:
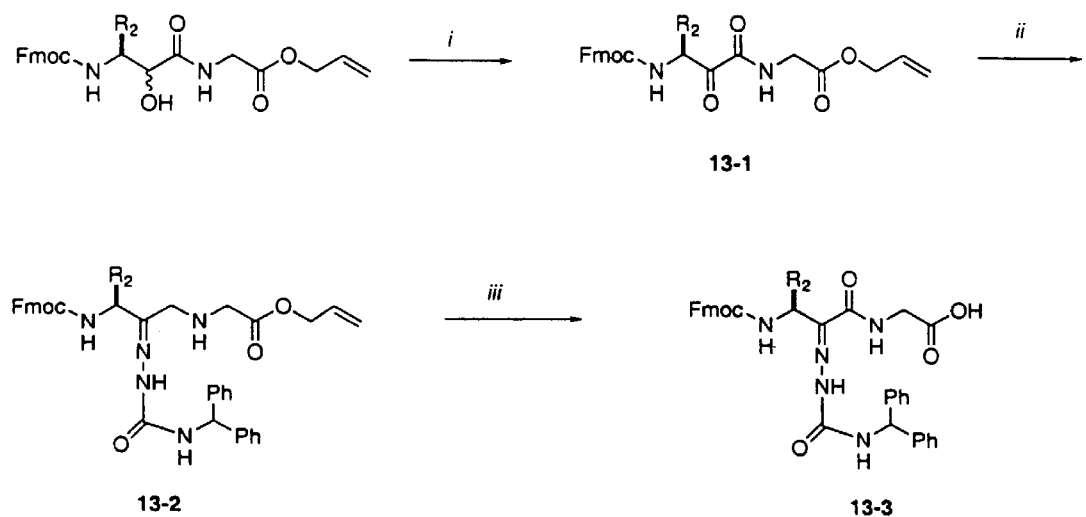
FIG. 13 depicts the synthesis of a semicarbazone-protected α-ketoamide derivative using an α-hydroxy-β-protected amino acid derivative from the TFA scheme, as described in Example 5. In this figure, (i) through (iii) are defined as follows: (i) EDC, DCA, DMSO, toluene, 0° C. to room temperature; (ii) diphenylmethyl semicarbazide, NaOAc.3H$_2$O, ethanol, water, heat; and (iii) dimedone, Pd(PPh$_3$)$_4$, THF.

FIG. 13 depicts a reaction scheme corresponding to the procedures in this Example.

Under a stream of nitrogen, the α-hydroxy-β-protected amino acid derivative from Example 3 (1 eq) was dissolved in a 1:1 mixture of dimethylsulfoxide (DMSO) and toluene (0.05M final concentration). Water soluble carbodiimide (EDC, 10 eq) was then added in one batch. The reaction mixture was cooled to 0° C., and dichloroacetic acid (DCA, 5 eq) was added dropwise. After the addition of dichloroacetic acid was completed, the reaction was stirred for 15 minutes at 0° C. and 1 h at room temperature. Water was added at 0° C. and the toluene was removed under reduced pressure. The remaining residue was diluted with ethyl acetate and washed several times with a saturated sodium bicarbonate solution followed by 1N sodium bisulfate and brine. The organic layer was dried over sodium sulfate and remaining residue was dissolved in ethyl acetate and washed twice with 1N sodium bisulfate, saturated sodium bicarbonate, followed by brine. The organic layer was dried and concentrated and the remaining residue was subjected to flash column chromatography in an ethyl acetate/ hexane solvent system. Pure product 13-2 was obtained in 60 to 98% yield as a white foam.

When allyl isocyanoacetate was the isonitrile used in the procedure of Example 3 to make the α-hydroxy-β-protected amino acid derivative, the following steps were followed for allyl ester deprotection of the semicarbazone protected α-ketoamide derivative.

To the protected product 13-2 (1 eq) in THF (0.02 M) was added dimedone (5 eq) followed by tetrakis(triphenylphosphine)palladium(O) catalyst (0.1 eq). The completion of the reaction was confirmed after 90 minutes using a 9:1 dichloromethane: methanol TLC system. The reaction mixture was concentrated and the remaining residue was dissolved in ethyl acetate and extracted three times with 0.1M potassium biphosphate. The organic layer was then treated with sodium bisulfite and the two phase system was stirred for 15 minutes. The phases were separated and the latter procedure was repeated twice more. The organic layer was dried and concentrated and subjected to purification by flash column chromatography. The pure product 13-3 was obtained as a white solid in 77–100% yield.

Table V depicts a variety of starting amino acids and their sidechains and N- and C-terminal protecting groups used to synthesize a variety of semicarbazone protected α-ketoamide derivatives using the procedure of Example 5.

TABLE V

Semicarbazone Derivatives of Formula (TFA-IV) Prepared Using the Procedure Described in Example 5

| Pr | $R_1$ | $R_2$ (Amino Acid) | % Yield | TLC ($R_f$ syn + anti isomers)[1] |
|---|---|---|---|---|
| Fmoc | —CH$_2$CO$_2$allyl | —CH(CH$_3$)$_2$ (Val) | 89.4 | 9MC:1M (0.05, 0.17) |
| Fmoc | —CH$_2$CO$_2$allyl | —(CH$_2$)$_2$CH$_3$ (norVal) | 93.6 | 9MC:1M (0.03, 0.13) |
| Fmoc | —CH$_2$CO$_2$allyl | —CH$_2$CH(CH$_3$)$_2$ (Leu) | 85.7 | 9MC:1M (0.07, 0.17) |
| Fmoc | —CH$_2$CO$_2$allyl | —(CH$_2$)$_3$CH$_3$ (norLeu) | 87.3 | 9MC:1M (0.07, 0.17) |
| Fmoc | —CH$_2$CO$_2$allyl | —CH$_2$CH$_3$ (Abu) | 100 | 9MC:1M (0.05, 0.15) |
| Fmoc | —CH$_2$CO$_2$allyl | —CH(O-t-Bu)CH$_3$ (Thr(tBu)) | 77.4 | 9MC:1M (0.03, 0.13) |
| Fmoc | —CH$_2$CO$_2$allyl | —CH(O-t-Bu)CH$_3$ (alloThr(t-Bu)) | 95.5 | 9MC:1M (0.03, 0.10) |

[1]MC = methylene chloride
M = Methanol

A specific Example of the synthesis of a semicarbazone-protected α-ketoamide derivative using the TFA Procedure of Example 3, and the allyl ester deprotection described in this Example, is provided in Example 7. The semicarbazone group is removed to yield a deprotected α-ketoamide derivative following the procedures set forth in Example 8 and hereinabove.

EXAMPLE 6

General Protocol for Synthesis of α-Hydroxy-β-Amino Acids using α-Hydroxy-β-Protected Amino Acid Derivatives from TFA Method I of Example 3 (TFA Method II)

The product of TFA Method I of Example 3 is the starting material to make α-hydroxy acids, which are useful intermediates for the synthesis of biologically active compounds which include serine protease inhibitors, such as inhibitors of thrombin and Factor Xa.

The synthesis of α-hydroxy-β-N-(tert-butyloxy-carbonyl) amino-4-cyclohexylbutanoic acid is exemplified in Example 6(A) below, and FIG. 10A. The synthesis of α-hydroxy-3-N-(tert-butoxycarbonyl)amino-6-ω-nitroguanidino) hexanoic acid 10B-5 is exemplified in (B), and FIG. 10B.

A. Cyclohexyl Alanine

The synthetic scheme is depicted in FIG. 10A.

To a solution of tert-butyloxycarbonyl-cyclohexylalaninal 10A-3 (5.42 g, 21.22 mmol; from Example 1) in dichloromethane (85 ml), was added tert-butyl isocyanide (2.88 ml, 25.46 mmol) and pyridine (6.86 ml, 84.86 mmol). The reaction mixture was cooled to 0° C. and trifluoroacetic acid (4.23 ml, 42.43 mmol) was added dropwise. The reaction was stirred at 0° C. for 1 hour, and then stirred uncapped at room temperature for 48 hours. TLC taken in 1:1 ethyl acetate: hexane ($R_f$=0.36) confirmed the completion of the reaction. The reaction mixture was concentrated and subjected to flash column chromatography on silica gel using a gradient run from 30:70 ethyl acetate:hexane to 40:60 ethyl acetate: hexane. Fractions containing the desired product N-Boc-cyclohexyl-norstatine tert-butylamide 10A-4 were pooled and concentrated to give an off white foam (3.49 g, 46.2%). NMR δ ppm (CDCl$_3$): 6.5–6.6 (2s, 1H), 4.8–5. (m, 1H), 3.9–4.05 (2dd, 2H), 3.85 (m, 1H), 1.6–1.9 (m, 7H), 1.4 (s, 1H), 1.35 (s, 1H), 1.1–1.3 (m, 3H), 0.8–1.0 (m, 1H).

The product 10A-4 (3.29 g, 9.24 mmol) was dissolved in 60 ml 6N HCl and was refluxed for twelve hours. The reaction was cooled to room temperature and was extracted three times with 100 ml portions of dichloromethane to remove colored impurities. The aqueous layer was concentrated using toluene as an azeotrope. The off white foam obtained (2.7 g) gave the correct mass (MH$^+$201.5) and the 2-hydroxy-3-amino-4-cyclohexyl butanoic acid (or "cyclohexylnorstatine") product was taken to the next step without further purification.

The crude product from the previous step, 10A-4, (1.92 g, 8.03 mmol) was dissolved in 20 ml each dioxane and water. Potassium carbonate (2.22 g, 16.07 mmol), followed by di-tert-butyl dicarbonate (3.51 g, 16.07 mmol), were added successively, and the reaction mixture was let to stir over night at room temperature. The dioxane was removed under reduced pressure and the remaining residue was diluted with water and was extracted twice with 20 ml portions of diethylether. The aqueous layer was acidified to pH 2–3 with 1N sodium bisulfate and was extracted with three 25 ml portions of ethyl acetate. The organic layer was dried over sodium sulfate and the 2-hydroxy-3-N-(tert-butoxycarbonyl)-4-cyclohexyl butanoic acid (or "N-Boc cyclohexylnorstatine") 10A-5, was concentrated to a white foam (1.74 g, 72%). NMR δ ppm (CD$_3$OD): 4.1 (m, 3H), 1.9 (m, 2H), 1.7 (m, 6H), (1.4–1.45 2s, 9H), 1.1–1.4 (m, 4H), 0.8–1.05 (m, 1H).

B. Arginine

The synthetic scheme is provided in FIG. 10B.

To a solution of tert-butyloxycarbonyl-argininyl(nitro) aldehyde 10B-3 (0.45 g, 1.5 mmol; from Example 1) in dichloromethane (6 ml), was added tert-butyl isocyanide (201 ml, 1.8 mmol) and pyridine (485 μl, 6 mmol). The reaction mixture was cooled to 0° C. and trifluoroacetic acid (231 μl, 3 mmol) was added dropwise. The reaction was stirred at 0° C. for 1 h, and then at room temperature for 48 hours. TLC taken in ethyl acetate ($R_f$ diastereomers=0.26, 0.37) confirmed the completion of the reaction. The reaction mixture was extracted three times each with 5 ml portions of 1N sodium bisulfate, saturated sodium bicarbonate and brine. The organic layer was dried and concentrated to an off white foam (0.56 g, 92%). No further purification steps were deemed necessary to yield 2-hydroxy-3-(N-tert-butoxycarbonyl)amino-6-(ω-nitroguanidino) hexanoic acid, tert-butylamide 10B-4. NMR δ ppm (CDCl$_3$): 6.75–6.8 (2s, 1H), 5.5 (d, 1H), 3.9–4.2 (m, 1H), 3.3–3.4 (m, 2H), 1.6–1.8 (m, 4H), 1.4–1.45 (2s, 9H), 1.35 (s, 9H).

The product of the previous step, 10B-4 (0.56 g, 1.38 mmol), was dissolved in 10 ml 6N HCl and was refluxed for twelve hours. The reaction was cooled to room temperature and the aqueous layer was extracted twice with dichloromethane (5 ml) to remove colored impurities. It was then concentrated to a sticky yellow solid. Analytical HPLC using a 4.6×250 mm reverse phase column, containing a C-18 resin comprised of 5 micron size gel particles with a 300 angstrom pore size, ran at 100% water (containing 0.1% trifluoroacetic acid) showed two diastereomeric peaks with the retention times of 3.8 and 4.2 minutes, respectively. Low resolution mass spectrum confirmed the desired mass (MH$^+$=250). Theoretical yield (0.39 g) was assumed and the compound 2-hydroxy-3-amino-6-(ω-nitroguanidino) hexanoic acid 10B-5a was taken to the next step without further purification. NMR δ ppm (D$_2$O): 4.45–4.6 (m), 3.7–3.8 (m), 3.3–3.4 (m), 3.1 (m), 2.1 (s), 1.8–1.9 (m), 1.4 (s).

The crude product from the previous step, 10B-5a (0.39 g, 1.38 mmol) was dissolved in 3 ml each dioxane and water. Sodium carbonate (326 mg, 3.08 mmol) followed by di-tert-butyl dicarbonate (744 mg, 3.41 mmol) were added successively, and the reaction mixture was let to stir over night at room temperature. The dioxane was removed under reduced pressure and the remaining residue was diluted with water and was extracted twice with 2 to 5 ml portions of diethylether. The aqueous layer was acidified to pH 2 to 3 with 1N sodium bisulfate and was extracted with three 3 ml portions of ethyl acetate. The organic layer was dried over sodium sulfate and concentrated to a white foam. The crude product was diluted with water (5–10 ml) and was subjected to HPLC purification using 2.2×25 cm reverse phase column, containing a C-18 resin comprised of 10 micron-size gel particles with a 300 angstrom pore size, eluting with a gradient ranging from 5–20% acetonitrile in water (containing 0.1% trifluoroacetic acid). The fractions containing the title compound, 2-hydroxy-3-N-(tert-butoxycarbonyl)amino-6-(ω-nitroguanidino) hexanoic acid, 10B-5b (250 mg, 52%), were pooled and lyophilized. Analytical HPLC using a 4.6×250 mm reverse phase column, containing a C-18 resin comprised of 5 micron size gel particles with a 300 angstrom pore size, using a gradient ranging from 5 to 50% acetonitrile in water (containing 0.1% trifluoroacetic acid) showed two diastereomeric peaks with the retention times of 9.5 and 10.5 minutes, respectively. NMR δ ppm (CD$_3$OD): 4.38 (d), 4.15 (d), 4.33 (bs), 4.19 (bs), 3.95 (m, 1H), 3.3 (m, 2H), 1.7 (m, 4H), 1.4 (s, 9H).

EXAMPLE 7

Specific Example of Synthesis of Semicarbazone Protected Intermediate Using TFA Procedure of Example 3 and Semicarbazone Protection Procedure of Example 5: Synthesis of 9-Fluorenylmethoxy Carbonyl-Norvalyl-α-Ketoamide (Diphenylmethyl Semicarbazone)-Glycine 14-6 (TFA Methods I, II, IV, IV)

Figure 14:
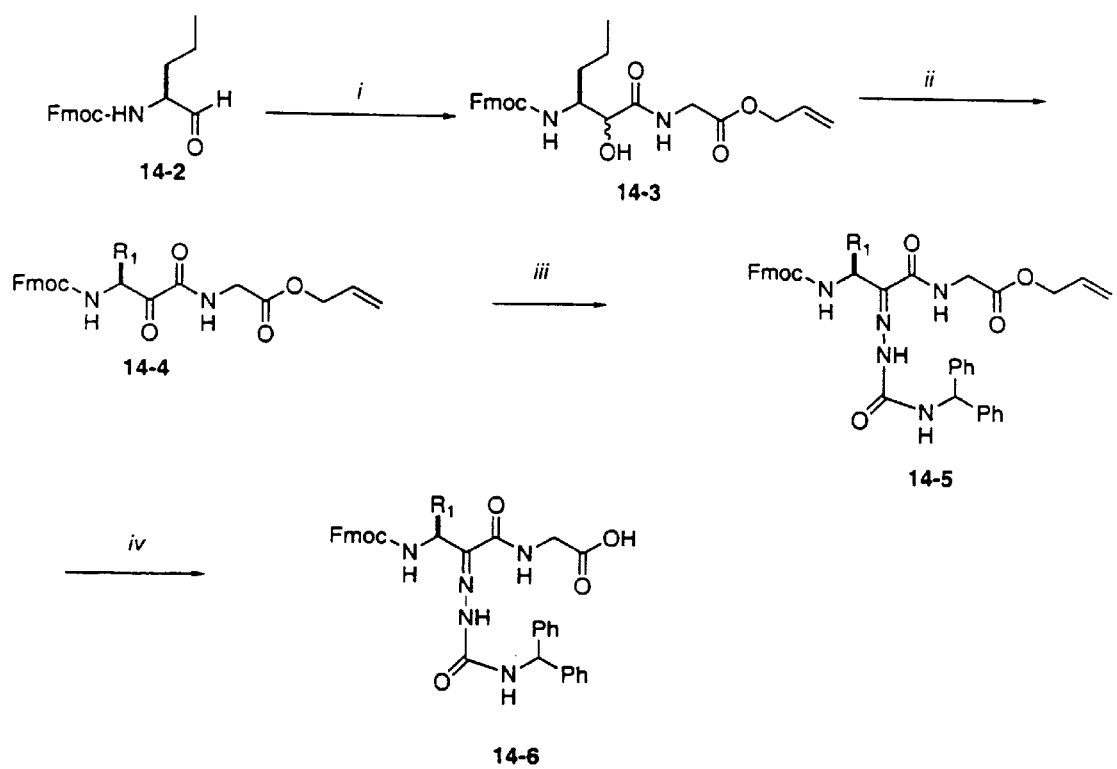
FIG. 14 depicts the reaction scheme for synthesizing a semicarbazone-protected intermediate described in Example 7. In this figure, (i) through (iv) are defined as follows: (i) CNCH$_2$CO$_2$allyl, TFA, pyridine, CH$_2$Cl$_2$, 0° C. to room temperature; (ii) EDC, DCA, DMSO, toluene, 0° C. to room temperature; (iii) diphenylmethyl semicarbazide, NaOAc.3H$_2$O, ethanol, water, heat; and (iv) dimedone, Pd(PPh$_3$)$_4$, THF.

The synthetic scheme for this Example, which yields an intermediate useful in the synthesis of cysteine and serine protease inhibitors, is depicted in FIG. 14.

A. Synthesis of N$^\alpha$-Fmoc-NorValyl-(CHOH)-Glycine-O-Allyl Ester 14-3

To a solution of Fmoc-norVal-aldehyde (14-2c; see Example 1) (5.47 g, 16.90 mmol) in dichloromethane (170 ml), was added allyl isocyanoacetate (2.46 ml, 20.28 mmol; see Example 2) and pyridine (5.47 ml, 67.61 mmol). The reaction mixture was cooled to 0° C. and trifluoroacetic acid (3.38 ml, 33.80 mmol) was added dropwise. The reaction was stirred at 0° C. for 1 hour, and then at room temperature for 48 hours. TLC taken in ethyl acetate confirmed the completion of the reaction. The reaction mix was concentrated and subjected to flash column chromatography using a gradient composed of 20:80 ethyl acetate: hexane to 70:30 ethyl acetate:hexane. Fractions containing the desired product were pooled and concentrated to a white foam (6.88 g, 87.3%). TLC in 50:50 ethyl acetate shows one spot (R$_f$= 0.37). NMR δ ppm (CD$_3$OD): 7.8 (m, 2H), 7.65 (m, 2H), 7.4 (m, 2H), 7.3 (m, 2H), 5.9 (m, 1H), 5.1–5.4 (m, 2H), 4.55–4.65 (m, 2H), 4.3–4.4 (m, 2H), 4.15–4.25 (m, 1H), 4.01 (s, 1H), 3.9–4.0 (m, 3H), 1.5–1.6 (m, 2H), 1.35–1.45 (m, 3H), 0.9 (m, 3H).

B. Synthesis of N$^\alpha$-Fmoc-NorValyl-(CO)-Glycine-O-Allyl Ester 14-4

Under a stream of nitrogen, the compound 14-3 from Example 7(A) (5.01 g, 10.77 mmol) was dissolved in 100 ml dimethylsulfoxide and 100 ml toluene. Water soluble carbodiimide (EDC, 20.6 g, 107.7 mmol) was then added in one batch. The reaction mixture was cooled to 0° C. and dichloroacetic acid (4.44 ml, 53.83 mmol) was added dropwise. After the addition of dichloroacetic acid was completed, the reaction was stirred for 15 minutes at 0° C. and 1 hour at room temperature. Water (70 ml) was added at 0° C. and the toluene was removed under reduced pressure. The remaining residue was diluted with ethyl acetate and washed several times with a saturated sodium bicarbonate solution followed by 1N sodium bisulfate and brine. The organic layer was dried over sodium sulfate and concentrated. The theoretical yield of 4.99 g was assumed and the reaction was taken to the next step without further purification. TLC in 50:50 ethyl acetate:hexane shows one spot (R$_f$=0.73).

C. Synthesis of N$^\alpha$-Fmoc-NorValyl-(dPsc)-Glycine-O-Allyl Ester 14-5

To the product of Example 7(B) (4.99 g, 10.75 mmol) dissolved in 130 ml ethanol and 42 ml water, were added diphenylmethyl semicarbazide (7.6 g, 21.5 mmol) and sodium acetate.3H$_2$O (1.76 g, 12.9 mmol), successively. The reaction mixture was refluxed for 90 minutes. The completion of reaction was confirmed by TLC taken in 1:1 ethyl acetate:hexane. Ethanol was removed under reduced pressure and the remaining residue was dissolved in ethyl acetate and washed twice with 10 ml portions of 1N sodium bisulfate, saturated sodium bicarbonate, followed by brine. The organic layer was dried and concentrated and the remaining residue was subjected to flash column chromatography in 20:80 ethyl acetate:hexane followed by 50:50 ethyl acetate: hexane. Fractions corresponding to the pure product were pulled and concentrated to give a white solid (5.76 g, 78%). TLC in 50:50 ethyl acetate:hexane shows two spots (syn and anti isomers) with R$_f$=0.42 and 0.5, respectively.

D. Synthesis of N$^\alpha$-Fmoc-NorValyl-(dPsc)-Glycine 14-6

To the product of Example 7(C) (4.53 g, 6.59 mmol) in THF (300 ml), was added dimedone (4.62 g, 32.97 mmol) followed by tetrakis(triphenylphosphine)palladium(O) catalyst (0.76 g, 0.66 mmol). The completion of the reaction was confirmed after 90 minutes using a 9:1 dichloromethane:methanol TLC system. The reaction mixture was concentrated and the remaining residue was dissolved in ethyl acetate and extracted three times with 50 ml portions of 0.1M potassium biphosphate. The organic layer was then treated with 50 ml sodium bisulfite and the two phase system was stirred for 15 minutes. The phases were separated and the procedure was repeated twice more. The organic layer was dried and concentrated and subjected to flash column chromatography starting with 20:80 ethyl acetate:hexane and gradually increasing the ethyl acetate concentration to 100%. This was followed with 9:1 dichloromethane:methanol solution. The fractions corresponding to the pure product were pooled and concentrated to obtain a white solid (3.99 g, 94%). TLC in 9:1 dichloromethane:methanol shows two spots (syn and anti isomers) with R$_f$=0.03 and 0.13, respectively. NMR δ ppm (CD$_3$OD): 7.75 (m, 2H), 7.6 (m, 3H), 7.2–7.4 (m, 14H), 6.1–6.2 (m, 1H), 4.25–4.4 (m, 2H), 4.1–4.2 (m, 2H), 3.85 (s, 2H), 1.6–1.8 (m, 2H), 1.3–1.5 (m, 2H), 0.95 (t, 3H).

EXAMPLE 8

General Procedure for Using TFA Procedure for Solid Phase Synthesis of a Ketoamide Library (TFA Methods I, III, IV, IV', V)

The TFA Procedure of Example 3 was used to construct a solid phase ketoamide library, in which each member of the library was 11 residues long:

Ac-P$_6$ P$_5$ P$_4$ P$_3$ P$_2$ P$_1$(CO)P$_1$' P$_2$' P$_3$' P$_4$' P$_5$'—NH$_2$

Figure 15:
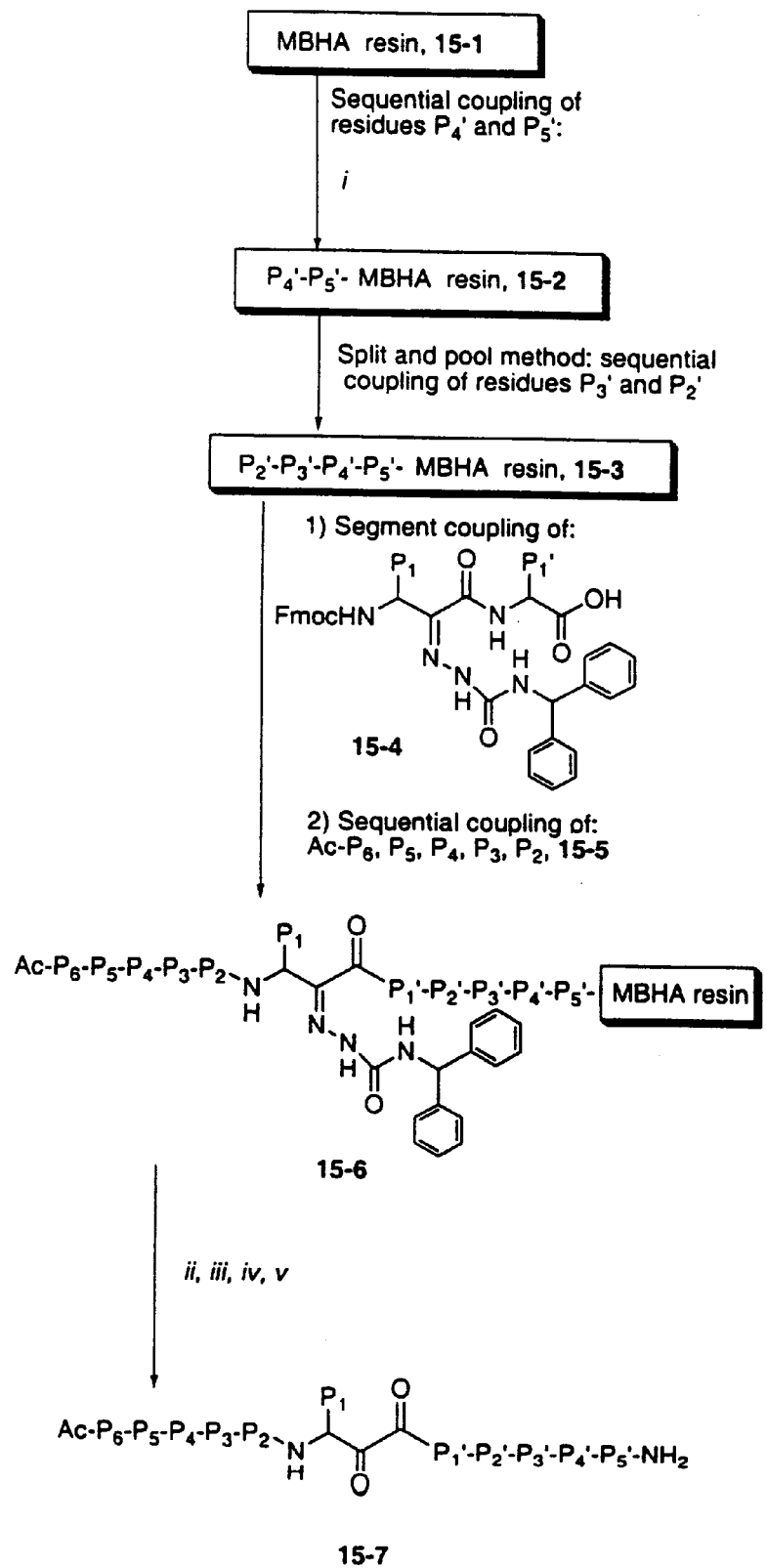
FIG. 15 depicts reactions used to synthesize a solid phase ketoamide library, as described in Example 8. In this figure, (i) through (v) are defined as follows: (i) sequential coupling depicted in FIG. 15 includes (a) a coupling step with TBTU/HOBt/DIEA/DMF and (b) a deprotection step; (ii) semicarbazone deprotection in polypropylene fitted columns, TFA/H$_2$O/pyruvic acid/DCM (9:1:2:2) (4×2 hours, then overnight); (iii) resin washed, dried and weighed; (iv) HF, Thioanisole; and (v) HPLC.

The library was designed to keep all residues constant, except residues P$_2$' and P$_3$', which varied and were incorporated into peptides during parallel synthesis. The P$_1$(CO)—P$_1$' site was a partially protected dipeptide of the general formula Fmoc-HN—(CHR)—(C=dPsc)-CO-Gly-OH, wherein dPsc denotes the diphenylmethyl semicarbazone protecting group on the ketoamide, and was obtained from the procedures set forth in Examples 3 and 5. The procedures in this Example are shown in FIG. 15.

Individual members of the library were synthesized in reaction vessels, such as Kan™ vessels obtained from Irori (11149 North Torrey Pines Rd., La Jolla, Calif. 92037), from their carboxy terminus using standard peptide synthetic techniques.

A total of 256 reaction vessels were used. The starting resin (33 mg MBHA resin purchased from NovaBiochem; substitution: 0.46 mmol/g) was weighed in each of the 256 vessels and was neutralized with a 5% solution of DIEA in DMF for 20 minutes. The Kan™ vessels were then drained and washed thoroughly with DMF, DCM and IPA.

The vessels were divided into three groups and each group was placed in a 500 ml polypropylene bottle. 250 ml of solvents were used in each bottle at each time for washings, deprotections and coupling reactions. The standard Fmoc/tBu protection strategy was employed and 3.5 eq of coupling reagents were used in each step. All couplings were achieved using TBTU/HOBt/DIEA coupling reagents in DMF.

Coupling of the first residue (P$_5$') was carried out at room temperature for 4 hours. Six reaction vessels were picked at random and the extent of coupling was determined for each vessel using the quantitative Kaiser ninhydrin test. Double coupling using fresh reagents was carried out when necessary. The reaction vessels were drained and washed successively with DMF, DCM, IPA, DCM and ether. The resin was then subjected to standard Fmoc cleavage (using 20% piperidine in DMF, 30 min) and another round of acylation was then carried out. The cycle was continued until the full peptide was assembled. When coupling to the variable regions P$_3$' and P$_2$', the split and pool method was adopted.

The reaction vessels were dried in vacuo and the resin from each vessel was transferred to a fritted disposable 4 ml polypropylene column.

For semicarbazone deprotection, the resin in each column was treated with the semicarbazone cleavage mixture consisting of a 9:1:2:2 solution of trifluoracetic acid:water:pyruvic acid:DCM for two hours (1 ml). After draining the cleavage cocktail, fresh reagent was added and the procedure was repeated three more times. Finally it was let to go once more over night.

The columns were drained and the resin was washed once each with DMF, DCM and IPA and dried in vacuo.

The peptide ketoamide was then subjected to HF cleavage using the standard protocol. The crude peptide was purified by HPLC and analyzed by mass spec and $^1$NMR spectroscopy. The overall yield of the peptides ranged from 2% to 28% with >97% purity in most cases.

EXAMPLE 9

Synthesis of a P$_1$-Ketoargininamide Thrombin Inhibitor Using the Complex Reaction of Example 4 (Complex Methods CI, CII, CIV)

Figure 16:
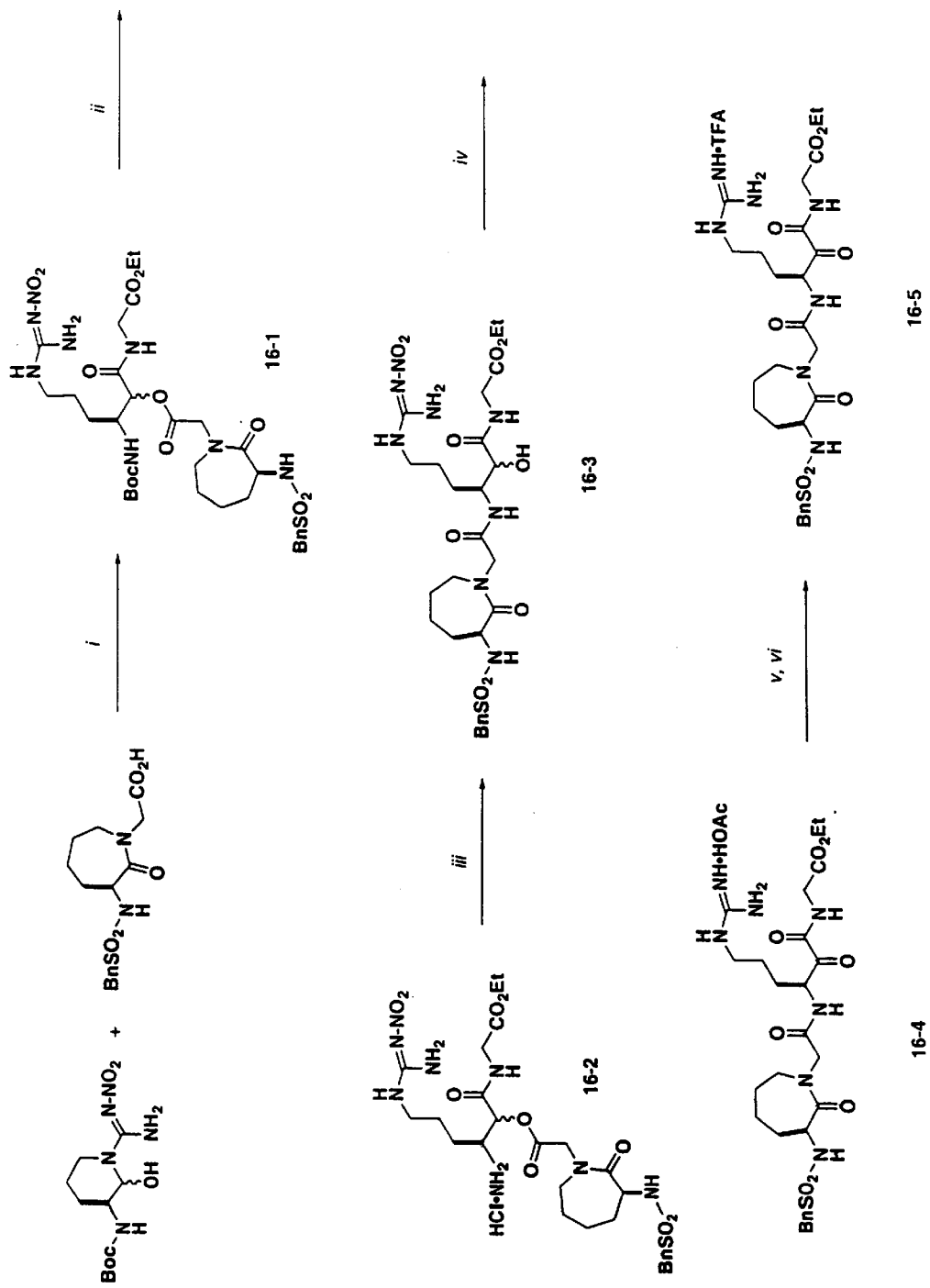
FIG. 16 depicts the reactions used to synthesize the α-ketoamide thrombin inhibitor described in Example 9. In this figure, (i) through (vi) are defined as: (i) CNCH$_2$CO$_2$Et, ethanol, room temperature, 39% yield; (ii) HCl, EtOAc, 0° C. to room temperature, approximately quantitative yield; (iii) Et$_3$N, ethanol, pH~8.5 to 9, 0° C. to room temperature, 63% yield; (iv) H$_2$, Pd/C, HOAc, ethanol, water, 45 psi, 95% yield; (v) EDC, DCAA, DMSO, toluene, 0° C. to room temperature; and (vi) HPLC, 57% yield.

FIG. 16 depicts the reaction scheme of this Example.
A. Synthesis of 16-1

To a solution of Boc-Arg(NO$_2$)—H (303.3 mg, 1.0 mmol) and 1-3-Benzylsulfonamido-2-azepinone-1-acetic acid (prepared according to Examples 27 to 31 of U.S. Pat. No. 5,703,208) (R$_3$X$_1$CO$_2$H) (341.4 mg, 1.0 mmol) in anhydrous ethanol (4 ml), was added ethyl isocyanoacetate (R$_1$NC) (113.1 mg, 109 ml, 1.0 mmole). The light red solution was stirred at ambient temperature for 16 hours, the cap was removed and the solvent was allowed to slowly evaporate. After several days, the resultant thick residue was dissolved in 100 ml of ethyl acetate and extracted successively with 20 ml portions of 1N HCl, saturated NaHCO$_3$ solution (2 times), water, brine, and then dried over anhydrous MgSO$_4$. Filtration and solvent removal gave a crude product which was purified by flash silica gel chromatography using dichloromethane:isopropanol 98:2 as eluent to afford 297 mg (39.2% yield) of product 16-1 as an amorphous colorless solid.

B. Deprotection to Give Intermediate 16-2

To a solution of 16-1 (259.0 mg, 0.34 mmol) in 1.5 ml of anhydrous ethyl acetate at 0° C., was added 12 N HCl in ethanol (566 mL, 6.8 mmol). After one hour the solvent was removed in vacuo. The residue was dissolved in fresh 10 ml portions of anhydrous acetonitrile and re-evaporated (repeated twice) and then evaporated once from a 10 ml portion of dichloromethane. High vacuum pumping for several hours afforded 237 mg (quantitative yield) of a tan powder.

C. Migration of Acyl Groups, 16-2 to 16-3: Preparation of BnSO$_2$-7Lac—G—R(NO$_2$)CH(OH)—Gly—OEt 16-3

To a solution of 16-2 (237 mg, 0.34 mmole) in 1.7 ml of ethanol was added Et$_3$N (68.9 mg, 0.68 mmol, 94 ml). The solution was stirred at ambient temperature for four days, the solvent was removed in vacuo, the residue was dissolved in 70 ml of ethyl acetate and extracted successively with 10 ml portions of 1N HCl (2 times), saturated NaHCO$_3$ solution (2 times), water, brine, and then dried over anhydrous MgSO$_4$. Filtration and solvent removal gave 158 mg (63.2 %) product which was essentially pure by TLC and NMR analysis. RP-HPLC analysis showed 2 peaks due to the presence of the diastereomeric α-hydroxy center.

D. Preparation of BnSO$_2$-7Lac—G—R(.HOAc)CH(OH)—Gly—OEt 16-4

To a solution of 16-3 (143 mg, 0.22 mmol) in 10 ml of ethanol, H$_2$O, acetic acid (4,1,1) was added 10% Pd/C (72 mg) and the mixture was hydrogenated at 45 psi on a Parr shaker overnight. After 16 hours, the solution was filtered, evaporated to dryness, and the residue was dissolved in acetonitrile and re-evaporated (repeated twice) and then evaporated from 10 ml portions of dichloromethane (repeated twice). High vacuum pumping for 3 days afforded 138 mg (95% yield) of product as an amorphous foam which was essentially pure by TLC and NMR analysis. RP-HPLC analysis (5–75) showed 2 peaks at 11.5 and 12 minutes due to the presence of the diastereomeric α-hydroxy center.

E. Preparation of BnSO$_2$-7Lac—G—R(.TFA)(CO))—Gly—OEt 16-5

To a solution of the dried acetate salt 16-4 (120 mg, 0.179 mmol) in 700 ml dry DMSO and 700 ml dry toluene, was added dichloroacetic acid (111.7 mg, 0.87 mmol, 5 equiv.). The solution was cooled to 0° and EDC (329.7 mg, 1.73 mmol) was added portionwise over 5 minutes. The cooling bath was removed and the yellow solution was stirred at ambient temperature for 90 minutes. The reaction was quenched with 20 mL H$_2$O and the aqueous layer was stored at 4° C. overnight. Purification by preparative RP-HPLC using a 15 to 30 acetonitrile-water gradient containing 0.1% TFA over 40 minutes, followed by fraction pooling and lyophilization, delivered 65 mg (51% yield) of product 16-5 as a colorless amorphous solid, homogeneous by TLC and RP-HPLC. Mass spectrum: 610 MH$^+$.

The product was shown to have thrombin inhibitory activity in standard in vitro assays designed to measure inhibitory activity and selectivity of the inhibitor toward thrombin versus other proteases.

EXAMPLE 10

Synthesis of a Highly Reactive $P_1$-α-Ketoargininamide Transition State Inhibitor Functionality Using the Complex Procedure of Example 4 (Complex Method CI)

Figures 17A, 17B:
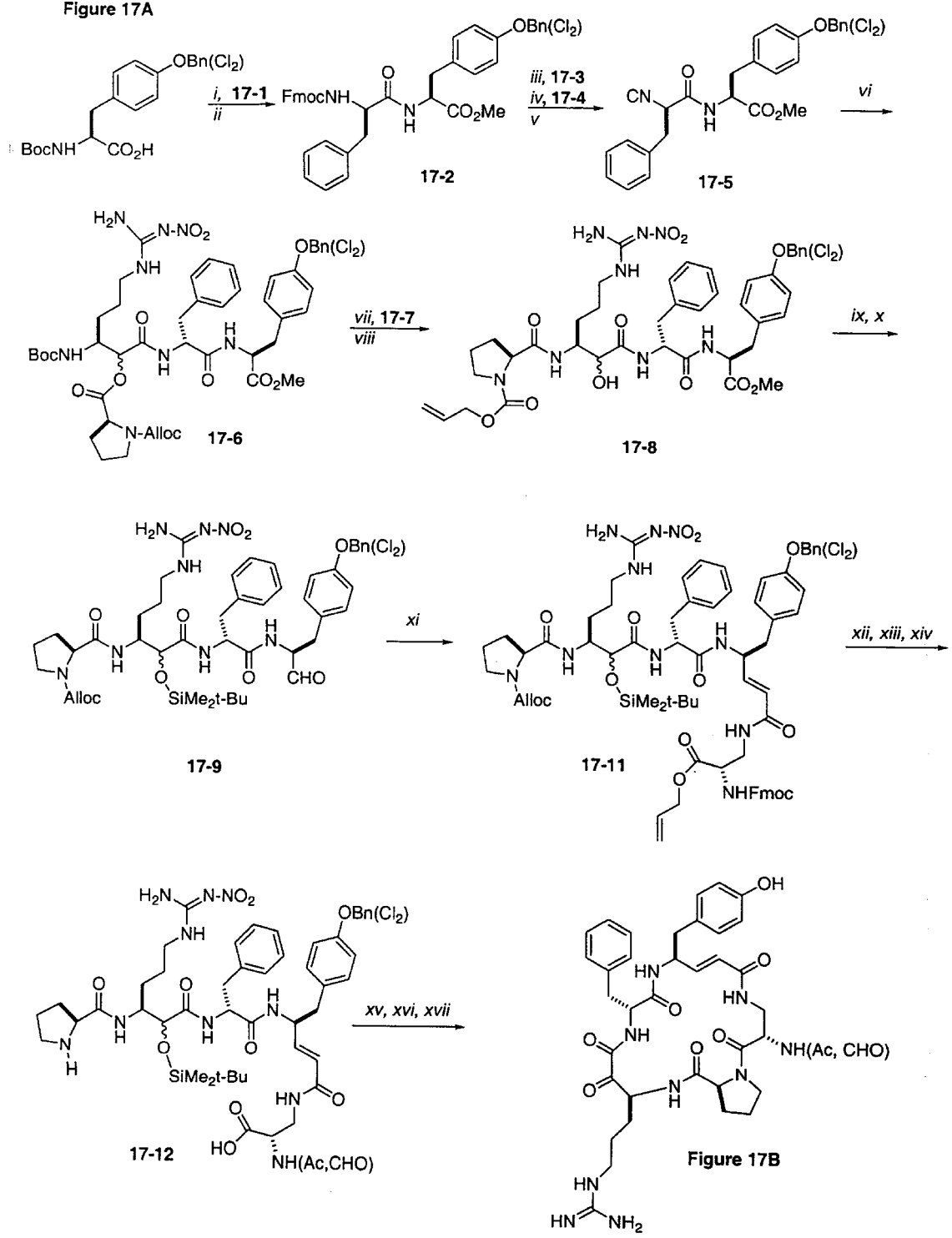
FIG. 17A depicts the reactions used to synthesize a P$_1$-α-ketoarginineamide intermediate (17-8) described in Example 10, which is used to make serine protease inhibitors and a reaction scheme using 17-8 to synthesize a cyclotheonamide depicted by FIG. 17B. In this figure, (i) through (xvii) are defined as follows: (i) MeOH, HCl, 0° C. to room temperature, 98% yield of Tyr(2,6—Cl$_2$Bn)—OMe.HCl (17-1); (ii) Fmoc-d—Phe—OH, EDC, HOBt, NMM, CH$_3$CN, room temperature, quantitative yield; (iii) Et$_2$NH, CH$_2$Cl$_2$, 0° C. to room temperature, 99% yield of d—Phe-Tyr(2,6—Cl$_2$Bn)—OMe (17-3); (iv) HCO$_2$H, Ac$_2$O, CH$_2$Cl$_2$, room temperature to reflux, 79% yield of N-formyl-d—Phe-Tyr(2,6—Cl$_2$Bn)—OMe (17-4); (v) CCl$_3$OCOCl, NMM, −40° C. to 0° C., CH$_2$Cl$_2$, 39% yield; (vi) Alloc-Pro-OH, Boc-Arg(NO$_2$)—H, CH$_2$Cl$_2$, 0° C. to room temperature, 2 days, 59% yield; (vii) HCl, MeOH, 0° C. to room temperature, quantitative yield of the hydrochloride salt (17-7); and (viii) Et$_3$N, pH about 8 to 9, MeOH, room temperature, 98% yield, acyl shift to yield intermediate (17-8); (ix) t-BuMe$_2$SiCl, imidazole, DMF; (x) reduce with DIBALH to generate aldehyde intermediate (17-9); (xi) reaction with stabilized ylide 17-10 to give 17-11; (xii) removal of Fmoc with diethylamine; (xiii) acylation of free amine with acetic or acetic-formic anhydride, optional DMAP catalyst; (xiv) simultaneous cleavage of allyl moieties with (Ph$_3$)$_4$Pd and dimedone in DMF to give intermediate (17-12); (xv) intramolecular macrocyclization under high dilution conditions with coupling agent (such as DPPA (diphenylphosphoryl azide) or BOP-Cl and DMAP); (xvi) removal of protecting groups with anhydrous HF; and (xvii) oxidation of secondary alcohol to give compounds of FIG. 17B.
FIG. 17B depicts the structures of cyclotheonamides A and B. Cyclotheonamide A has the N-formyl group and cyclotheonamide B has the N-acetyl group. The compounds of FIG. 17B are members of a cyclotheonamide family of macrocyclic peptides incorporating a highly reactive P$_1$-α-ketoargininamide transition state functionality which are active as serine protease inhibitors.
Figure 17C:
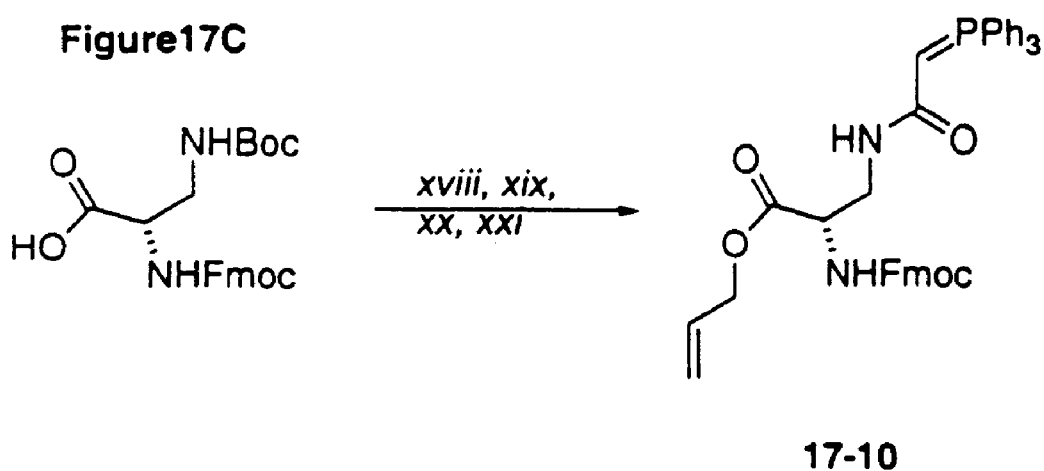
FIG. 17C depicts a reaction scheme for intermediate (17-10) which is prepared by a four step protocol from a—N-Fmoc-β-N-Boc-l-DAPA. In this figure, (xviii) to (xxi) are defined as follows: (xviii) allyl alcohol and PTSA catalyst; (xix) acylation of β-amino allyl ester with bromoacetyl bromide and base (such as triethylamine); (xx) triphenylphosphine to give phosphonium salt; and (xxi) hindered base (such as lithium bis-trimethylsilylamide) in THF to give ylide (17-10).

FIGS. 17A and 17C depict the reaction schemes described in this Example.

The compound 17-8 made following the method of this Example is an intermediate in the synthesis of peptides within the cyclotheonamide family of macrocyclic peptides, which are potent serine protease inhibitors. FIG. 17B depicts the structures for certain cyclotheonamide compounds. A reaction scheme for the preparation of the compounds depicted in FIG. 17B using intermediate 17-B is outlined. FIG. 17C depicts a reaction scheme for preparing the ylide 17-10.

A. Preparation of Tyr(2,6-$Cl_2$Bn)—OMe.Hydrochloride 17-1

Acetyl chloride (19.63 g, 0.25 mol, 17.8 ml) was added slowly to 200 ml anhydrous methanol at −5° C. to 5° C. with exclusion of moisture ($CaCl_2$ drying tube). After stirring the solution for 5 minutes, Boc-Tyr(2,6-$Cl_2$)—OH (11.04 g, 0.025 mol) was added rapidly over 2 minutes. The clear solution was stirred for 1 hour at 0° C., the bath was removed and the solution was allowed to stir at ambient temperature for 15 hours. After refluxing for one hour, the methanol was removed in vacuo, the residue was dissolved in 100 ml fresh methanol and evaporated. This procedure was repeated and the resultant colorless solid was washed with two small portions of methanol and collected by suction filtration. Vacuum drying overnight afforded 9.56 g (98% yield) of 17-1 as a colorless solid, judged pure by NMR and tlc analysis.

B. Preparation of Fmoc-d-Phe-Tyr(2,6-$Cl_2$Bn)—OMe 17-2

To a mixture of Fmoc-d-Phe—OH (7.75 g, 0.020 mol), 17-1 (8.60 g, 0.022 mol) and HOBt (3.66 g, 0.024 mol) in 100 ml anhydrous acetonitrile and 100 ml anhydrous DMF, was added EDC (4.27 g, 0.022 mol) followed by N-methyl morpholine (6.07 g, 0.060 mol, 6.60 ml). The resultant thick slurry was stirred at ambient temperature overnight and the solvents were removed. The residue was dissolved in 1700 ml of dichloromethane and extracted successively with 100 ml portions of 1N HCl (2 times), saturated $NaHCO_3$ solution (2 times), water, brine, and then dried over anhydrous $MgSO_4$. Filtration and solvent removal gave 27 g of the crude product as a colorless solid which was purified by Trituration with a small portion of cold methanol, collected by suction filtration and dried under vacuum to provide 14.5 g (quantitative yield) of 17-2 as a colorless solid. TLC (silica gel; EtOAc, $R_f$=0.37; UV, PMA visualization). Pure by NMR analysis.

C. Preparation of d-Phe-Tyr(2,6-$Cl_2$Bn)—OMe 17-3

To a slurry of 17-2 (7.23 g, 10.0 mmol) in 100 ml of dichloromethane was added diethylamine (7.34 g, 100 mmol, 10.4 ml). The reaction mixture was heated to reflux for 2 hours and then was stirred at ambient temperature overnight. Solvents were removed and the residue was triturated with 50 mL of ether, refrigerated overnight, and collected by suction filtration to afford 4.95 g (99% yield) of amino intermediate 17-3 which was judged to be >95% pure by NMR analysis and which was utilized immediately in Example 10(D).

D. Preparation of N-Formyl-d-Phe-Tyr(2 6-$Cl_2$Bn)—OMe 17-4

To a slurry of 17-3 (2.50 g, 5.00 mmol) in 10 ml of 96% formic acid and 10 ml of dichloromethane was added acetic anhydride (3.06 g, 30 mmol, 2.83 mL). The reaction mixture was stirred at ambient temperature overnight and then poured into 60 ml ice-water with vigorous stirring. The mixture was extracted three times with 200 mL of dichloromethane. The combined organic phases were extracted successively with 50 ml portions of 1N HCl, saturated $NaHCO_3$ solution (2 times), water, brine, and then dried over anhydrous $MgSO_4$. Filtration and solvent removal gave the crude product which was triturated with ether to afford 2.08 g (78.8% yield) of product 17-4 as a colorless solid. TLC (silica gel; EtOAc, Rf=0.41; UV, PMA visualization). The product was judged pure by NMR analysis.

E. Preparation of Isocyano-d-Phe-Tyr (2,6-$Cl_2$Bn)—OMe 17-5

To a slurry of 17-4 (1.58 g, 3.0 mmol) in 20 ml of anhydrous dichloromethane was added N-methylmorpholine (0.758 g, 7.5 mmol, 820 mL). After cooling to −40° C., diphosgene (326.4 mg, 1.65 mmol, 199 mL) dissolved in 5 mL of anhydrous dichloromethane was added dropwise. The resultant brown suspension was stirred at −40° C. for 2 hours, warmed to 0° C., and quenched with 6 ml of water. Dilution with 100 ml of dichloromethane was followed by extraction with 2×20 ml saturated $NaHCO_3$ solution and 10 mL of water. Drying over anhydrous $Na2SO_4$, filtration and solvent removal afforded the crude product. The crude product was purified by flash chromatography on silica gel, eluting with dichloromethane:ethyl acetate (1:1) to provide 600 mg (39.2% yield) of 17-5 as a red solid. This product was stored at 4° C. under nitrogen and utilized immediately in the following reaction of Example 10(F). TLC (silica gel; EtOAc, hexanes: 1, 1, Rf=0.45; UV, PMA visualization). Pure by NMR analysis.

F. Synthesis of 17-6 Using Complex Method CI

A solution of Boc-Arg($NO_2$)—H (382.2 mg, 1.26 mmol (see Example 1), N-Alloc-proline (as $R_3X_1CO_2H$) (298.0 mg, 1.50 mmol) and isonitrile 17-5 (as $R_1NC$) (590.0 mg, 1.15 mmol) in anhydrous dichloromethane (4.6 ml) was stirred at ambient temperature for 16 hours; then, the cap was removed and the solvent was allowed to slowly evaporate. After one day, the resultant thick residue was dissolved in 200 ml of ethyl acetate and extracted successively with 50 ml portions of 1N HCl, saturated $NaHCO_3$ solution (2 times), water, brine, and then dried over anhydrous $MgSO_4$. Filtration and solvent removal gave a crude product. The crude product was purified by flash silica gel chromatography using dichloromethane:isopropanol 98:2 as eluent to afford 690 mg (59.3% yield) of product 17-6 as an amorphous colorless solid. RP-HPLC analysis (5–75) showed two peaks at 21.1 and 21.3 minutes, respectively, due to the presence of the diastereomeric α-acyloxy center, indicative of retention of chiral integrity of the remaining four chiral centers.

TLC (silica gel; dichloromethane:isopropanol, 9:1, Rf=0.61; ethyl acetate, Rf=0.38, 0.31; UV, PMA visualization). Mass Spectrum: $MH^+$1013, $MNa^+$1036. $^1$H-NMR (400 MHz) analysis indicated an approximately 1,1 mixture of diastereomers at the newly formed α-acyloxy center, chemically pure.

G. Deprotection of Adduct 17-6 to Afford Hydrochloride Salt 17–7

To a solution of 17-6 (675 mg, 0.666 mmol) in 5 ml of anhydrous methanol at 0° C. was added freshly prepared 5N HCl in anhydrous methanol (10 ml, 50 mmol). After 40 minutes at 0° C. the solvent was removed in vacuo. The residue was dissolved in fresh 10 ml portions of anhydrous acetonitrile and re-evaporated (repeated twice) and then evaporated once from a 10 ml portion of dichloromethane. High vacuum pumping for several hours afforded 659 mg (103% of theory, ~quantitative yield) of 17-7 as a light brown foam which was used immediately in the following reaction. This product was judged to be >95% pure by NMR analysis.

H. Migration of acyl in 17-7: Preparation of Alloc-Pro-Arg (NO$_2$)CH(OH)-d-Phe-Tyr(2,6-Cl$_2$Bn)—OMe 17-8

To a solution of 17-7 (625 mg, 0.658 mmol) in 3.33 ml of anhydrous methanol was added Et$_3$N (134.6 mg, 1.33 mmol, 185 ml). The solution was stirred at ambient temperature for 2 hours, during which time a thick yellow slurry had formed. The solvent was removed and the residue was dissolved in 200 ml of ethyl acetate and extracted successively with 20 ml portions of 1N HCl, saturated NaHCO$_3$ solution (2 times), water, brine, and then dried over anhydrous MgSO$_4$. Filtration and solvent removal gave 588 mg (97.9 %) of product 17–8 which was essentially pure by TLC and NMR analysis. RP-HPLC analysis showed two peaks due to the presence of the diastereomeric α-hydroxy center. Mass spectrum: 913 MH$^+$, 935 Mna$^+$.

I. Preparation of Ylide 17-10

FIG. 17C depicts this reaction scheme.

Intermediate 17–10 may be prepared by a four step reaction scheme from the commercially available starting material α-N-Fmoc-β-N-Boc-l-DAPA. The starting material is treated with allyl alcohol and PTSA catalyst (step xviii). The resulting β-amino allyl ester is acylated with bromoacetyl bromide in the presence of a suitable base such as triethylamine (step xix), and then reacted with triphenyl phosphine to produce the corresponding phosphonium salt (step xx). The phosphonium is converted to the desired glide 17-10 with a hindered base such as lithium bis-trimethylsilylamide in THF solvent (step xxi).

J. Preparation of Cyclotheonamides from Intermediate 17-8

Intermediate 17–8 is protected with t-BuMe$_2$SiCl, imidazole and DMF (step ix) and then reduced with DIBALH (step x) to generate reactive aldehyde intermediate 17-9.

In step xi, the freshly prepared aldehyde intermediate 17-9 undergoes a Wittig-type olefination with the stabilized ylide 17-10 to give 17-11. The Fmoc protecting group is removed with diethylamine in step xii. The resulting free amine is acylated with acetic or acetic-formic anhydride, optionally in the presence of DMAP catalyst in step xiii. Simultaneous cleavage of both allyl moieties with (Ph$_3$)$_4$Pd and dimedone in THF in step xiv provides intermediate 17-12, which has either an N-acetyl or N-formyl-DAPA moiety. In step xv, intramolecular macrocyclization is effected under high dilution conditions with an appropriate coupling agent such as DPPA (diphenylphosphorylazide) or BOP-Cl and DMAP. In step xvi all remaining protecting groups are removed with anhydrous hydrogen fluoride in thioanisole. In step xvi a Moffatt or Dess-Martin oxidation of the secondary alcohol function gives yields of the compounds depicted in FIG. 17B. Cyclotheonamide A has an N-formyl group; cyclotheonamide B has an N-acetyl group.

EXAMPLE 11

Complex Reaction To Afford α-Hydroxy-β-Protected Aminoamide Derivatives; Condensation-Deacylation-Deprotection Protocol (Complex Method CV)

Figure 18:
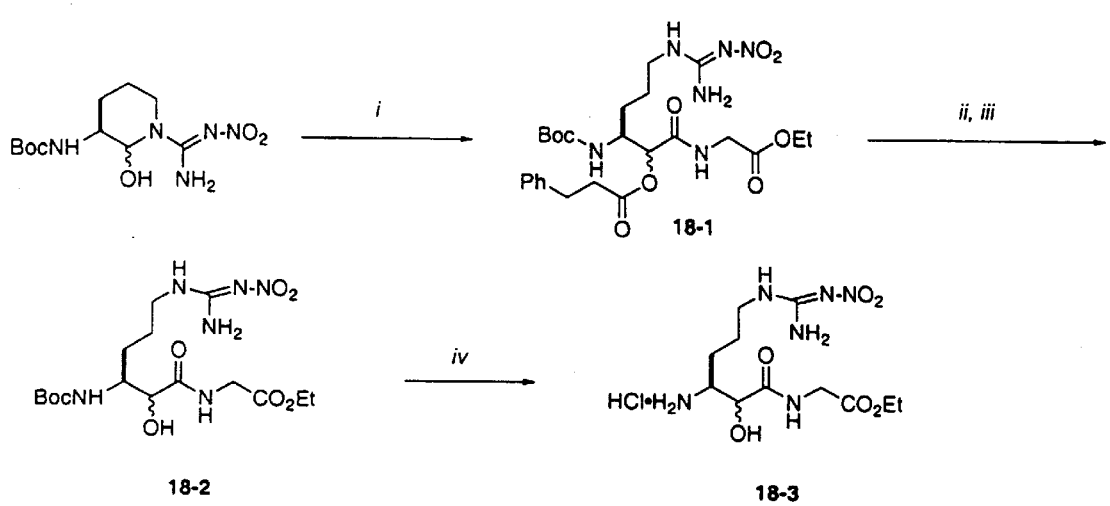
FIG. 18 depicts the reactions used in TFA-Method V and described in Example 11. In particular, this figure depicts a complex reaction method which may be used to synthesize α-hydroxy-β-protected aminoamide derivatives. In this figure, (i) through (iv) are defined as follows: (i) Ph(CH$_2$)$_2$CO$_2$H, CNCH$_2$CO$_2$Et, ethanol, room temperature, 5 days, 59% yield; (ii) NaOEt (catalytic amount), ethanol, 30 minutes, 0° C.; (iii) HOAc, 91% yield; and HCl, ethanol, 0° C., 10 minutes, approximately quantitative yield.

The reactions described in this Example, and compounds identified by number, are depicted in FIG. 18.

A. Synthesis of (Boc-Arg(NO$_2$)CH(O$_2$C-phenethyl)CO—Gly—OEt) 18-1

To a slurry of Boc-Arg(NO$_2$)—H (3.03 g, 10.0 mmol) and hydrocinnamic acid (1.50 g, 10.0 mmol) in anhydrous ethanol (40 ml), was added ethyl isocyanoacetate (1.13 g, 1.09 ml, 10.0 mmole). The resulting light red solution was stirred at ambient temperature for 14 hours, the cap was removed from the reaction vessel and the solvent was allowed to slowly evaporate. After 4 days, the resulting thick residue was dissolved in 300 ml of ethyl acetate and extracted successively with 30 ml portions of saturated NaHCO$_3$ solution, water, brine (2 times), and then dried over anhydrous MgSO$_4$. Filtration and solvent removal gave a crude product which was purified by flash silica gel chromatography using dichloromethane:isopropanol (96:4) as eluent to afford 3.36 g (59.4% yield) of product 18-1 as an amorphous colorless foam; TLC (silica gel, EtOAc): Rf=0.52.

B. Selective Cleavage of Acyl Moiety and Synthesis of (Boc-Arg(N$_2$)CH(OH)CO-Gly-OEt) 18-2

To a solution of 18-1 (3.40 g, 6.31 mmol) in anhydrous ethanol (25 ml) at ambient temperature under nitrogen, was added NaOEt solution (0.77 ml of 21% by weight solution, 1.89 mmol, 0.3 equiv.). After 30 minutes, the reaction mixture was quenched by addition of acetic acid (2 ml) and the solvents were removed in vacuo. The crude product was purified by flash silica gel chromatography using dichloromethane:isopropanol (9:1) as eluent to afford 2.48 g (91.0 % yield) of product 18-2 as a pale yellow foam. TLC (silica gel; dichloromethane, ethanol: 9,1): Rf=0.40 and 0.32.

C. Deprotection of Intermediate 18-2. Synthesis of (HCl.Arg (NO$_2$)CH(OH)CO-Gly-OEt) 18-3

Intermediate 18-2 (1.30 g, 3.00 mmol) was dissolved in 12 N HCl in ethanol (10 ml). After 10 minutes at ambient temperature, the solvent was removed in vacuo. The residue was dissolved in fresh 10 ml portions of anhydrous ethanol and re-evaporated (repeated twice) and then evaporated once from a 10 ml portion of acetonitrile. High vacuum pumping for several hours afforded 1.18 g (quantitative yield) of 18-3 as a colorless foam.

We claim:
1. A method of preparing a compound of formula (A):

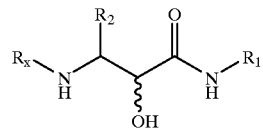

wherein
(i) $R_x$ is —PG or —C(O)R$_3$ where PG is a protecting group;
(ii)
(a) R$_1$, R$_2$ and R$_3$ are independently selected from the group consisting of alkyl of 1 to about 12 carbon atoms, cycloalkyl of 3 to about 12 carbon atoms, alkenyl of 2 to about 12 carbon atoms, cycloalkenyl of 5 to about 12 carbon atoms, and alkynyl 3 to about 12 carbon atoms, all optionally substituted with 1 to 3 substituents independently selected from the group consisting of Y$_1$, Y$_2$ and Y$_3$; aryl of about 5 to about 14 carbon atoms which is optionally mono-, di- or tri-substituted with Y$_1$, Y$_2$, or Y$_3$; heteroaryl of about 5 to about 14 ring atoms, with the ring atoms selected from carbon atoms and heteroatoms, wherein the heteroatoms are selected from oxygen, nitrogen and sulfur and which is optionally mono-, di-, tri-substituted with $Y_1$, $Y_2$ or $Y_3$; aralkyl of about 6 to about 18 carbon atoms which is optionally mono-, di- or tri-substituted on the aryl ring with $Y_1$, $Y_2$ or $Y_3$; and heteroaralkyl of about 5 to about 18 carbon atoms having about 5 to about 14 ring atoms with the ring atoms selected from carbon atoms and heteroatoms, wherein the heteroatoms are selected from oxygen, nitrogen and sulfur and which is optionally mono, di- or tri-substituted on the ring with $Y_1$, $Y_2$ or $Y_3$;

(b) alternatively $R_1$ is —CH($R_5$)C(O)$W_1$ or a peptidyl substituent of the formula —(Xaa$_1$)$_n$W$_2$, wherein $R_5$ is hydrogen, alkyl of 1 to about 12 carbon atoms, cycloalkyl of 3 to about 12 carbon atoms, aryl of 5 to about 14 carbon atoms, or aralkyl of about 7 to about 15 carbon atoms, all optionally substituted with 1 to 3 substituents independently selected from hydroxy, sulfhydryl, alkylthio, carboxyl, amide, amino alkylamino, indolyl, 3-N-formylindolyl, benzyloxy, halobenzyloxy, guanidino, nitroguanidino or imidazolyl optionally substituted with alkoxyalkyl; $W_1$ and $W_2$ are independently selected from —OH, —O$Z_1$, —SH, —S$Z_1$, —NH$_2$, —NH$Z_1$ and —N$Z_1Z_2$; each Xaa$_1$ is an independently selected amino acid residue and n is an integer from 1 to 10; or (c) alternatively $R_3$C(O)— is $W_1$CH($R_5$)C(O)— or $R_4$ wherein $R_4$ is a peptide substituent of the formula $Z_1$X(Xaa$_2$)$_r$— wherein each Xaa$_2$ is an independently selected amino acid residue, r is an integer from 1 to 10 and X is —C(O)—, —S(O)$_2$—, —OC(O)—, or a direct link;

(iii) each $Y_1$, $Y_2$ and $Y_3$ is independently selected from the group consisting of halogen, cyano, nitro, tetrazolyl, guanidino, amidino, methylguanidino, —CH$_3$, —CH$_2$CH$_3$, —CH$_2$CH$_2$CH$_3$, —CH(CH$_3$)$_2$, —CH$_2$CF$_3$, —CH(CF$_3$)$_2$, —OCF$_3$, —OCF$_2$H, —OCF$_2$CF$_3$, —OC(O)NH$_2$, —OC(O)NH$Z_1$, —OC(O)N$Z_1Z_2$, —NHC(O) $Z_1$, —NHC(O)NH$_2$, —NHC(O)NH$Z_1$, —NHC(O)NH$Z_1Z_2$, —C(O)OH, —C(O)O$Z_1$, —C(O)NH$_2$, —C(O)NH$Z_1$, —C(O)N$Z_1Z_2$, —P(O)$_3$H$_2$, —P(O)$_3$($Z_1$)$_2$, —S(O)$_3$H, —S(O)$_m$$Z_1$, —$Z_1$, —O$Z_1$, —OH, —NH$_2$, —NH$Z_1$, —N$Z_1Z_2$, and —S(O)$_m$(CF$_2$)$_q$CF$_3$, wherein m is 0, 1 or 2, q is an integer from 0 to 5; and (iv) each $Z_1$ and $Z_2$ is independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms; comprising the steps:

(a) reacting a protected amino-aldehyde of the formula PGNHCH($R_2$)CHO, an isonitrile of the formula $R_1$NC and a carboxy compound of the formula YCO$_2$H wherein Y is CF$_3$ or $R_3$ to give an aminoacyloxycarboxamide compound of formula (B):

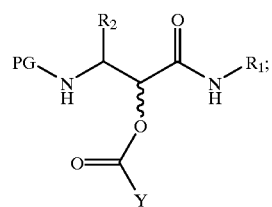

and (b)
(i) where $R_x$ is PG, treating the amino acyloxycarboxamide intermediate from step (a) under acyloxy group removing conditions to give said compound of formula (A); or
(ii) where $R_x$ is —C(O)$R_3$, treating the amino acyloxycarboxamide intermediate from step (a) under PG group removing conditions which include a pH of about 6 to about 9 to give said compound of formula (A).

2. A method according to claim 1 wherein $R_x$ is —C(O)$R_3$.

3. A method of preparing an α-ketoamide derivative of formula (C):

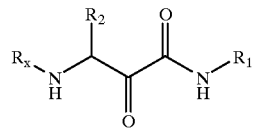

which comprises treating a compound of formula (A) prepared by the method of claim 1 under oxidizing conditions to oxidize the compound of formula (A) to give a compound of formula (C).

4. A method according to claim 3 wherein said oxidizing conditions comprise 1-ethyl-3-(3-dimethylaminopropyl) carbodiimide hydrochloride salt (EDC) and dichloroacetic acid DCA in dimethylsulfoxide (DMSO) and toluene.

5. A method according to claim 1 where wherein $R_x$ is PG.

6. A method according to claim 5 wherein Y is $R_3$.

7. A method according to claim 6 wherein said acyloxy group removing conditions comprise selective hydrolysis with an alkali metal alkoxide.

8. A method according to claim 5 wherein Y is —CF$_3$.

9. A method according to claim 8 wherein said acyloxy group removing conditions comprise extractive aqueous procedures.

10. A method according to claim 8 wherein step (a) includes a mild organic base.

11. A method of preparing a α-hydroxy-β-amino acid derivative comprising the steps of:

(a) contacting a blocked aminoaldehyde of the formula PGNHCH($R_2$)CHO with trifluoroacetic acid and an isonitrile compound of the formula $R_1$NC in the presence of a mild organic base to give a transient amino acyloxy trifluoroacetate derivative; and (b) treating the amino acyloxy trifluoroacetate derivative of step (a) under acyloxy removing conditions to give an α-hydroxy-β-amino acid derivative of formula (TFA-I):

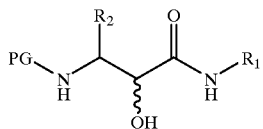

TFA-I wherein:
(i) PG is a protecting group; and
(ii)
  (a) $R_1$ and $R_2$ are independently selected from the group consisting of alkyl of 1 to about 12 carbon atoms, cycloalkyl of 3 to about 12 carbon atoms, alkenyl of 2 to about 12 carbon atoms, cycloalkenyl of 5 to about 12 carbon atoms, and alkynyl 3 to about 12 carbon atoms, all optionally substituted with 1 to 3 substituents independently selected from the group consisting of $Y_1$, $Y_2$ and $Y_3$; aryl of about 5 to about 14 carbon atoms which is optionally mono-, di- or tri-substituted with $Y_1$, $Y_2$, and/or $Y_3$; heteroaryl of about 5 to about 14 ring atoms, with the ring atoms selected from carbon atoms and heteroatoms, wherein the heteroatoms are selected from oxygen, nitrogen and sulfur and which is optionally mono-, di-, tri-substituted with $Y_1$, $Y_2$ and/or $Y_3$; aralkyl of about 6 to about 18 carbon atoms which is optionally mono-, di- or tri-substituted on the aryl ring with $Y_1$, $Y_2$ or $Y_3$; and heteroaralkyl of about 5 to about 18 carbon atoms having about 5 to about 14 ring atoms with the ring atoms selected from carbon atoms and heteroatoms, wherein the heteroatoms are selected from oxygen, nitrogen and sulfur and which is optionally mono, di- or tri-substituted on the ring with $Y_1$, $Y_2$ or $Y_3$; or
  (b) alternatively $R_1$ is —CH($R_5$)C(O)$W_1$, or a peptidyl substituent of the formula —(Xaa$_1$)$_n$W$_2$, wherein $R_5$ is hydrogen, alkyl of 1 to about 12 carbon atoms, cycloalkyl of 3 to about 12 carbon atoms, aryl of 5 to about 14 carbon atoms, or aralkyl of about 7 to about 15 carbon atoms, all optionally substituted with 1 to 3 substituents independently selected from hydroxy, sulfhydryl, alkylthio, carboxyl, amide, amino alkylamino, indolyl, 3-N-formylindolyl, benzyloxy, halobenzyloxy, guanidino, nitroguanidino or imidazolyl optionally substituted with alkoxyalkyl; $W_1$ and $W_2$ are independently selected from —OH, —OZ$_1$, —SH, —SZ$_1$, —NH$_2$, —NHZ$_1$ and —NZ$_1$Z$_2$; each Xaa$_1$ is an independently selected amino acid residue and n is an integer from 1 to 10;
(iii) each $Y_1$, $Y_2$ and $Y_3$ is independently selected from the group consisting of halogen, cyano, nitro, tetrazolyl, guanidino, amidino, methylguanidino, —CH$_3$, —CH$_2$CH$_3$, —CH$_2$CH$_2$CH$_3$, —CH(CH$_3$)$_2$, —CH$_2$CF$_3$, —CH(CF$_3$)$_2$, —OCF$_3$, —OCF$_2$H, —OCF$_2$CF$_3$, —OC(O)NH$_2$, —OC(O)NHZ$_1$, —OC(O)NZ$_1$Z$_2$, —NHC(O)Z$_1$, —NHC(O)NH$_2$, —NHC(O)NHZ$_1$, —NHC(O)NHZ$_1$Z$_2$, —C(O)OH, —C(O)OZ$_1$, —C(O)NH$_2$, —C(O)NHZ$_1$, —C(O)NZ$_1$Z$_2$, —P(O)$_3$H$_2$, —P(O)$_3$(Z$_1$)$_2$, —S(O)$_3$H, —S(O)$_m$Z$_1$, —Z$_1$, —OZ$_1$, —OH, —NH$_2$, —NHZ$_1$, —NZ$_1$Z$_2$, and —S(O)$_m$(CF$_2$)$_q$CF$_3$, wherein m is 0, 1 or 2, q is an integer from 0 to 5; and
(iv) and each Z$_1$ and Z$_2$ is independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms.

12. A method according to claim 11 further comprising the step of:
  (c) contacting the product of step (b) with an acid reagent under hydrolytic conditions to give an α-hydroxy-β-amino acid of the formula (TFA-II)

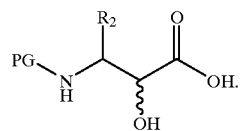

(TFA-II)

13. A method of preparing an α-ketoamide derivative of the formula (TFA-III):

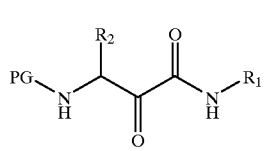

(TFA-III)

wherein
(i) PG is a protecting group; and
(ii)
  (a) $R_1$ and $R_2$ are independently selected from the group consisting of alkyl of 1 to about 12 carbon atoms, cycloalkyl of 3 to about 12 carbon atoms, alkenyl of 2 to about 12 carbon atoms, cycloalkenyl of 5 to about 12 carbon atoms, and alkynyl 3 to about 12 carbon atoms, all optionally substituted with 1 to 3 substituents independently selected from the group consisting of $Y_1$, $Y_2$ and $Y_3$; aryl of about 5 to about 14 carbon atoms which is optionally mono-, di- or tri-substituted with $Y_1$, $Y_2$, or $Y_3$; heteroaryl of about 5 to about 14 ring atoms, with the ring atoms selected from carbon atoms and heteroatoms, wherein the heteroatoms are selected from oxygen, nitrogen and sulfur and which is optionally mono-, di-, tri-substituted with $Y_1$, $Y_2$ or $Y_3$; aralkyl of about 6 to about 18 carbon atoms which is optionally mono-, di- or tri-substituted on the aryl ring with $Y_1$, $Y_2$ or $Y_3$; and heteroaralkyl of about 5 to about 18 carbon atoms having about 5 to about 14 ring atoms with the ring atoms selected from carbon atoms and heteroatoms, wherein the heteroatoms are selected from oxygen, nitrogen and sulfur and which is optionally mono, di- or tri-substituted on the ring with $Y_1$, $Y_2$ or $Y_3$; or
  (b) alternatively $R_1$ is —CH($R_5$)C(O)$W_1$, or a peptidyl substituent of the formula —(Xaa$_1$)$_n$W$_2$, wherein $R_5$ is hydrogen, alkyl of 1 to about 12 carbon atoms, cycloalkyl of 3 to about 12 carbon atoms, aryl of 5 to about 14 carbon atoms, or aralkyl of about 7 to about 15 carbon atoms, all optionally substituted with 1 to 3 substituents independently selected from hydroxy, sulfhydryl, alkylthio, carboxyl, amide, amino alkylamino, indolyl, 3-N-formylindolyl, benzyloxy, halobenzyloxy, guanidino, nitroguanidino or imidazolyl optionally substituted with alkoxyalkyl; $W_1$ and $W_2$ are independently selected from —OH, —$OZ_1$, —SH, —$SZ_1$, —$NH_2$, —$NHZ_1$ and —$NZ_1Z_2$; each $Xaa_1$ is an independently selected amino acid residue and n is an integer from 1 to 10;

(iii) each $Y_1$, $Y_2$ and Y3 is independently selected from the group consisting of halogen, cyano, nitro, tetrazolyl, guanidino, amidino, methylguanidino, —$CH_3$, —$CH_2CH_3$, —$CH_2CH_2CH_3$, —$CH(CH_3)_2$, —$CH_2CF_3$, —$CH(CF_3)_2$, —$OCF_3$, —$OCF_2H$, —$OCF_2CF_3$, —OC(O)$NH_2$, —OC(O)$NHZ_1$, —OC(O)$NZ_1Z_2$, —NHC(O)$Z_1$, —NHC(O)$NH_2$, —NHC(O)$NHZ_1$, —NHC(O)$NHZ_1Z_2$, —C(O)OH, —C(O)$OZ_1$, —C(O)$NH_2$, —C(O)$NHZ_1$, —C(O)$NZ_1Z_2$, —P(O)$_3H_2$, —P(O)$_3(Z_1)_2$, —S(O)$_3$H, —S(O)$_mZ_1$, —$Z_1$, —$OZ_1$, —OH, —$NH_2$, —$NHZ_1$, —$NZ_1Z_2$, and —S(O)$_m(CF_2)_qCF_3$, wherein m is 0, 1 or 2, q is an integer from 0 to 5; and (iv) and each $Z_1$ and $Z_2$ is independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms; comprising the steps of:

(a) contacting a blocked aminoaldehyde of the formula PGNHCG($R_2$)CHO with trifluoroacetic acid and an isonitrile compound of the formula $R_1$NC in the presence of a mild organic base to give a transient amino acyloxy trifluoroacetate derivative;

(b) treating the amino acyloxy trifluoroacetate derivative of step (a) under acyloxy removing conditions or to give an α-hydroxy-β-amino acid derivative of formula (TFA-I); and (c) treating the derivative from step (b) under oxidizing conditions to give an α-ketoamide derivative of formula (TFA-III).

14. A method of preparing a semicarbazone-protected ketoamide derivative of formula (TFA-IV)

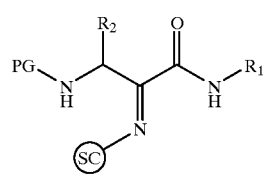

(TFA-IV)

wherein (i) PG is a protecting group; and (ii)

(a) $R_1$ and $R_2$ are independently selected from the group consisting of alkyl of 1 to about 12 carbon atoms, cycloalkyl of 3 to about 12 carbon atoms, alkenyl of 2 to about 12 carbon atoms, cycloalkenyl of 5 to about 12 carbon atoms, and alkynyl 3 to about 12 carbon atoms, all optionally substituted with 1 to 3 substituents independently selected from the group consisting of $Y_1$, $Y_2$ and $Y_3$; aryl of about 5 to about 14 carbon atoms which is optionally mono-, di- or tri-substituted with $Y_1$, $Y_2$, or $Y_3$; heteroaryl of about 5 to about 14 ring atoms, with the ring atoms selected from carbon atoms and heteroatoms, wherein the heteroatoms are selected from oxygen, nitrogen and sulfur and which is optionally mono-, di-, tri-substituted with $Y_1$, $Y_2$ or $Y_3$; aralkyl of about 6 to about 18 carbon atoms which is optionally mono-, di- or tri-substituted on the aryl ring with $Y_1$, $Y_2$ or $Y_3$; and heteroaralkyl of about 5 to about 18 carbon atoms having about 5 to about 14 ring atoms with the ring atoms selected from carbon atoms and heteroatoms, wherein the heteroatoms are selected from oxygen, nitrogen and sulfur and which is optionally mono, di- or tri-substituted on the ring with $Y_1$, $Y_2$ or $Y_3$; or (b) alternatively $R_1$ is —CH($R_5$)C(O)$W_1$, or a peptidyl substituent of the formula —$(Xaa_1)_nW_2$, wherein $R_5$ is hydrogen, alkyl of 1 to about 12 carbon atoms, cycloalkyl of 3 to about 12 carbon atoms, aryl of 5 to about 14 carbon atoms, or aralkyl of about 7 to about 15 carbon atoms, all optionally substituted with 1 to 3 substituents independently selected from hydroxy, sulfhydryl, alkylthio, carboxyl, amide, amino alkylamino, indolyl, 3-N-formylindolyl, benzyloxy, halobenzyloxy, guanidino, nitroguanidino or imidazolyl optionally substituted with alkoxyalkyl; $W_1$ and $W_2$ are independently selected from —OH, —$OZ_1$, —SH, —$SZ_1$, —$NH_2$, —$NHZ_1$ and —$NZ_1Z_2$; each $Xaa_1$ is an independently selected amino acid residue and n is an integer from 1 to 10;

(iii) each $Y_1$, $Y_2$ and $Y_3$ is independently selected from the group consisting of halogen, cyano, nitro, tetrazolyl, guanidino, amidino, methylguanidino, —$CH_3$, —$CH_2CH_3$, —$CH_2CH_2CH_3$, —$CH(CH_3)_2$, —$CH_2CF_3$, —$CH(CF_3)_2$, —$OCF_3$, —$OCF_2H$, —$OCF_2CF_3$, —OC(O) $NH_2$, —OC(O)$NHZ_1$, —OC(O)$NZ_1Z_2$, —NHC(O)$Z_1$, —NHC(O)$NH_2$, —NHC(O)$NHZ_1$, —NHC(O)$NHZ_1Z_2$, —C(O)OH, —C(O)$OZ_1$, —C(O)$NH_2$, —C(O)$NHZ_1$, —C(O)$NZ_1Z_2$, —P(O)$_3H_2$, —P(O)$_3(Z_1)_2$, —S(O)$_3$H, —S(O)$_mZ_1$, —$Z_1$, —$OZ_1$, —OH, —$NH_2$, —$NHZ_1$, —$NZ_1Z_2$, and —S(O)$_m(CF_2)_qCF_3$, wherein m is 0, 1 or 2, q is an integer from 0 to 5;

(iv) and each $Z_1$ and $Z_2$ is independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms; and (v) and —SC is a semicarbazone group of the formula —NHC(O)NHQ wherein Q is selected from the group consisting of hydrogen, alkyl of 1 to about 12 carbon atoms, alkenyl of 2 to about 12 carbon atoms, alkynyl of 3 to about 12 carbon atoms, aryl of 5 to about 18 carbon atoms, heteroaryl of 5 to about 14 ring atoms with the ring atoms selected from carbon atoms and heteroatoms, wherein the heteroatoms are selected from oxygen nitrogen and sulfur, di-arylalkyl and tri-arylalkyl; comprising the step of contacting a α-ketoamide derivative of formula (TFA-III)

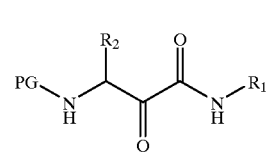

(TFA-III)

with a semicarbazide of the formula $NH_2NHC(O)NHQ$ under reactive conditions to give the semicarbazone derivative of formula (TFA-IV).

15. A method of preparing a peptidyl ketoamide of formula (TFA-V)

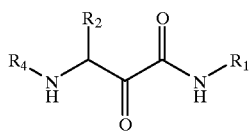
(TFA-V)

wherein (i)
(a) $R_1$ and $R_2$ are independently selected from the group consisting of alkyl of 1 to about 12 carbon atoms, cycloalkyl of 3 to about 12 carbon atoms, alkenyl of 2 to about 12 carbon atoms, cycloalkenyl of 5 to about 12 carbon atoms, and alkynyl 3 to about 12 carbon atoms, all optionally substituted with 1 to 3 substituents independently selected from the group consisting of $Y_1$, $Y_2$ and $Y_3$; aryl of about 5 to about 14 carbon atoms which is optionally mono-, di- or tri-substituted with $Y_1$, $Y_2$, or $Y_3$; heteroaryl of about 5 to about 14 ring atoms, with the ring atoms selected from carbon atoms and heteroatoms, wherein the heteroatoms are selected from oxygen, nitrogen and sulfur and which is optionally mono-, di-, tri-substituted with $Y_1$, $Y_2$ or $Y_3$; aralkyl of about 6 to about 18 carbon atoms which is optionally mono-, di- or tri-substituted on the aryl ring with $Y_1$, $Y_2$ or $Y_3$; and heteroaralkyl of about 5 to about 18 carbon atoms having about 5 to about 14 ring atoms with the ring atoms selected from carbon atoms and heteroatoms, wherein the heteroatoms are selected from oxygen, nitrogen and sulfur and which is optionally mono, di- or tri-substituted on the ring with $Y_1$, $Y_2$ or $Y_3$; or (b) alternatively $R_1$ is —$CH(R_5)C(O)W_1$, or a peptidyl substituent of the formula —$(Xaa_1)_nW_2$, wherein $R_5$ is hydrogen, alkyl of 1 to about 12 carbon atoms, cycloalkyl of 3 to about 12 carbon atoms, aryl of 5 to about 14 carbon atoms, or aralkyl of about 7 to about 15 carbon atoms, all optionally substituted with 1 to 3 substituents independently selected from hydroxy, sulfhydryl, alkylthio, carboxyl, amide, amino alkylamino, indolyl, 3-N-formylindolyl, benzyloxy, halobenzyloxy, guanidino, nitroguanidino or imidazolyl optionally substituted with alkoxyalkyl; $W_1$ and $W_2$ are independently selected from —OH, —$OZ_1$, —SH, —$SZ_1$, —$NH_2$, —$NHZ_1$ and —$NZ_1Z_2$; and each $Xaa_1$ is an independently selected amino acid residue and n is an integer from 1 to 10;

(iii) each $Y_1$, $Y_2$ and $Y_3$ is independently selected from the group consisting of halogen, cyano, nitro, tetrazolyl, guanidino, amidino, methylguanidino, —$CH_3$, —$CH_2CH_3$, —$CH_2CH_2CH_3$, —$H(CH_3)_2$, —$CH_2CF_3$, —$CH(CF_3)_2$, —$OCF_3$, —$OCF_2H$, —$OCF_2CF_3$, —$OC(O)NH_2$, —$OC(O)NHZ_1$, —$OC(O)NZ_1Z_2$, —$NHC(O)Z_1$, —$NHC(O)NH_2$, —$NHC(O)NHZ_1$, —$NHC(O)NHZ_1Z_2$, —$C(O)OH$, —$C(O)OZ_1$, —$C(O)NH_2$, —$C(O)NHZ_1$, —$C(O)NZ_1Z_2$, —$P(O)_3H_2$, —$P(O)_3(Z_1)_2$, —$S(O)_3H$, —$S(O)_mZ_1$, —$Z_1$, —$OZ_1$, —OH, —$NH_2$, —$NHZ_1$, —$NZ_1Z_2$, N-morpholino, —$S(CF_2)_qCF_3$, and —$S(O)_m(CF_2)_qCF_3$, wherein m is 0, 1 or 2, q is an integer from 0 to 5, and each $Z_1$ and $Z_2$ is independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms; and (iv) $R_4$ is $Z_1$—X—$(Xaa_2)_r$— wherein X is —C(O)—, —S(O)—$_2$, —OC(O)— or a direct link, each $Xaa_2$ is an independently selected amino acid residue and r is an integer from 1 to 10; comprising the steps of:

(a) removing protecting group PG from a protected α-ketoamide derivative of formula (TFA-III)

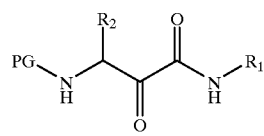
(TFA-III)

wherein PG is a protecting group: and (b) contacting the deprotected α-ketoamide derivative from step (a) with a compound of the formula $R_4$-LG, wherein LG is a leaving group, under coupling conditions to form an intermediate of the formula (TFA-V).

16. A method of preparing an α-hydroxy-β-aminoamide derivative of the formula (CI)

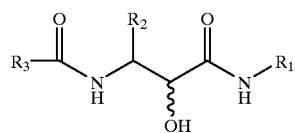
(CI)

wherein (i)
(a) $R_1$, $R_2$ and $R_3$ are independently selected from the group consisting of alkyl of 1 to about 12 carbon atoms, cycloalkyl of 3 to about 12 carbon atoms, alkenyl of 2 to about 12 carbon atoms, cycloalkenyl of 5 to about 12 carbon atoms, and alkynyl 3 to about 12 carbon atoms, all optionally substituted with 1 to 3 substituents independently selected from the group consisting of $Y_1$, $Y_2$ and $Y_3$; aryl of about 5 to about 14 carbon atoms which is optionally mono-, di- or tri-substituted with $Y_1$, $Y_2$, or $Y_3$; heteroaryl of about 5 to about 14 ring atoms, with the ring atoms selected from carbon atoms and heteroatoms, wherein the heteroatoms are selected from oxygen, nitrogen and sulfur and which is optionally mono-, di-, tri-substituted with $Y_1$, $Y_2$ or $Y_3$; aralkyl of about 6 to about 18 carbon atoms which is optionally mono-, di- or tri-substituted on the aryl ring with $Y_1$, $Y_2$ or $Y_3$; and heteroaralkyl of about 5 to about 18 carbon atoms having about 5 to about 14 ring atoms with the ring atoms selected from carbon atoms and heteroatoms, wherein the heteroatoms are selected from oxygen, nitrogen and sulfur and which is optionally mono, di- or tri-substituted on the ring with $Y_1$, $Y_2$ or $Y_3$;

(b) alternatively $R_1$ is —$CH(R_5)C(O)W_1$ or a peptidyl substituent of the formula —$(Xaa_1)_nW_2$, wherein $R_5$ is hydrogen, alkyl of 1 to about 12 carbon atoms, cycloalkyl of 3 to about 12 carbon atoms, aryl of 5 to about 14 carbon atoms, or aralkyl of about 7 to about 15 carbon atoms, all optionally substituted with 1 to 3 substituents independently selected from hydroxy, sulfhydryl, alkylthio, carboxyl, amide, amino alkylamino, indolyl, 3-N-formylindolyl, benzyloxy, halobenzyloxy, guanidino, nitroguanidino or imidazolyl optionally substituted with alkoxyalkyl; $W_1$ and $W_2$ are independently selected from —OH, —$OZ_1$, —SH, —$SZ_1$, —$NH_2$, —$NHZ_1$ and —$NZ_1Z_2$; each $Xaa_1$ is an independently selected amino acid residue and n is an integer from 1 to 10; or (c) alternatively $R_3C(O)$— is $W_1CH(R_5)C(O)$— or $R_4$ wherein $R_4$ is a peptide substituent of the formula $Z_1X(Xaa_2)_r$— wherein each $Xaa_2$ is an independently selected amino acid residue, r is an integer from 1 to 10 and X is —C(O)—, —$S(O)_2$—, —OC(O)—, or a direct link;

(ii) each $Y_1$, $Y_2$ and $Y_3$ is independently selected from the group consisting of halogen, cyano, nitro, tetrazolyl, guanidino, amidino, methylguanidino, —$CH_3$, —$CH_2CH_3$, —$CH_2CH_2CH_3$, —$CH(CH_3)_2$, —$CH_2CF_3$, —$CH(CF_3)_2$, —$OCF_3$, —$OCF_2H$, —$OCF_2CF_3$, —$OC(O)NH_2$, —$OC(O)NHZ_1$, —$OC(O)NZ_1Z_2$, —$NHC(O)Z_1$, —$NHC(O)NH_2$, —$NHC(O)NHZ_1$, —$NHC(O)NHZ_1Z_2$, —C(O)OH, —$C(O)OZ_1$, —$C(O)NH_2$, —$C(O)NHZ_1$, —$C(O)NZ_1Z_2$, —$P(O)_3H_2$, —$P(O)_3(Z_1)_2$, —$S(O)_3H$, —$S(O)_mZ_1$, —$Z_1$, —$OZ_1$, —OH, —$NH_2$, —$NHZ_1$, —$NZ_1Z_2$, and —$S(O)_m(CF_2)_qCF_3$, wherein m is 0, 1 or 2, q is an integer from 0 to 5; and (iii) each $Z_1$ and $Z_2$ is independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms; comprising the steps of:

(a) reacting an N-terminally blocked aminoaldehyde of the formula $PGNHCH(R_2)CHO$, wherein PG is a protecting group, with an isonitrile of the formula $R_1NC$, and a carboxylic acid of the formula $R_3CO_2H$ in solvent to give an amino α-acyloxycarboxamide derivative of the formula

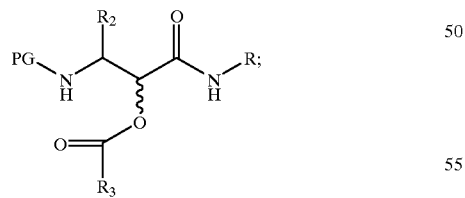

and (b) removing protecting group PG from the amino α-acyloxycarboxamide derivative from step (a) under PG group removing conditions which include a pH of about 6 to about 9 thereby effecting acyl migration to give an α-hydroxy-β-aminoamide derivative of formula (CI).

17. A method of preparing an α-ketoamide derivative of formula (CII)

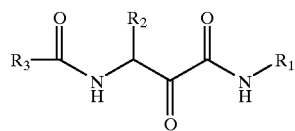

(CII)

wherein (i)
(a) $R_1$, $R_2$ and $R_3$ are independently selected from the group consisting of alkyl of 1 to about 12 carbon atoms, cycloalkyl of 3 to about 12 carbon atoms, alkenyl of 2 to about 12 carbon atoms, cycloalkenyl of 5 to about 12 carbon atoms, and alkynyl 3 to about 12 carbon atoms, all optionally substituted with 1 to 3 substituents independently selected from the group consisting of $Y_1$, $Y_2$ and $Y_3$; aryl of about 5 to about 14 carbon atoms which is optionally mono-, di- or tri-substituted with $Y_1$, $Y_2$, or $Y_3$; heteroaryl of about 5 to about 14 ring atoms, with the ring atoms selected from carbon atoms and heteroatoms, wherein the heteroatoms are selected from oxygen, nitrogen and sulfur and which is optionally mono-, di-, tri-substituted with $Y_1$, $Y_2$ or $Y_3$; aralkyl of about 6 to about 18 carbon atoms which is optionally mono-, di- or tri-substituted on the aryl ring with $Y_1$, $Y_2$ or $Y_3$; and heteroaralkyl of about 5 to about 18 carbon atoms having about 5 to about 14 ring atoms with the ring atoms selected from carbon atoms and heteroatoms, wherein the heteroatoms are selected from oxygen, nitrogen and sulfur and which is optionally mono, di- or tri-substituted on the ring with $Y_1$, $Y_2$ or $Y_3$;

(b) alternatively $R_1$ is —$CH(R_5)C(O)W_1$ or a peptidyl substituent of the formula —$(Xaa_1)_nW_2$, wherein $R_5$ is hydrogen, alkyl of 1 to about 12 carbon atoms, cycloalkyl of 3 to about 12 carbon atoms, aryl of 5 to about 14 carbon atoms, or aralkyl of about 7 to about 15 carbon atoms, all optionally substituted with 1 to 3 substituents independently selected from hydroxy, sulfhydryl, alkylthio, carboxyl, amide, amino alkylamino, indolyl, 3-N-formylindolyl, benzyloxy, halobenzyloxy, guanidino, nitroguanidino or imidazolyl optionally substituted with alkoxyalkyl; $W_1$ and $W_2$ are independently selected from —OH, —$OZ_1$, —SH, —$SZ_1$, —$NH_2$, —$NHZ_1$ and —$NZ_1Z_2$; each $Xaa_1$ is an independently selected amino acid residue and n is an integer from 1 to 10; or (c) alternatively $R_3C(O)$— is $W_1CH(R_5)C(O)$— or $R_4$ wherein $R_4$ is a peptide substituent of the formula $Z_1X(Xaa_2)_r$— wherein each $Xaa_2$ is an independently selected amino acid residue, r is an integer from 1 to 10 and X is —C(O)—, —$S(O)_2$—, —OC(O)—, or a direct link;

(ii) each $Y_1$, $Y_2$ and $Y_3$ is independently selected from the group consisting of halogen, cyano, nitro, tetrazolyl, guanidino, amidino, methylguanidino, —$CH_3$, —$CH_2CH_3$, —$CH_2CH_2CH_3$, —$CH(CH_3)_2$, —$CH_2CF_3$, —$CH(CF_3)_2$, —$OCF_3$, —$OCF_2H$, —$OCF_2CF_3$, —$OC(O)NH_2$, —$OC(O)NHZ_1$, —$OC(O)NZ_1Z_2$, —$NHC(O)Z_1$, —$NHC(O)NH_2$, —$NHC(O)NHZ_1$, —$NHC(O)NHZ_1Z_2$, —C(O)OH, —$C(O)OZ_1$, —$C(O)NH_2$, —$C(O)NHZ_1$, —$C(O)NZ_1Z_2$, —$P(O)_3H_2$, —$P(O)_3(Z_1)_2$, —$S(O)_3H$, —$S(O)_mZ_1$, —$Z_1$, —$OZ_1$, —OH, —$NH_2$, —$NHZ_1$, —$NZ_1Z_2$, and —$S(O)_m(CF_2)_qCF_3$, wherein m is 0, 1 or 2, q is an integer from 0 to 5; and (iv) each $Z_1$ and $Z_2$ is independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms; comprising the steps of:

(a) reacting an N-terminally blocked aminoaldehyde of the formula $PGNHCH(R_2)CHO$, wherein PG is a protecting group, with an isonitrile of the formula $R_1NC$, and a carboxylic acid of the formula $R_3CO_2H$ in solvent to give an amino α-acyloxycarboxamide derivative of the formula

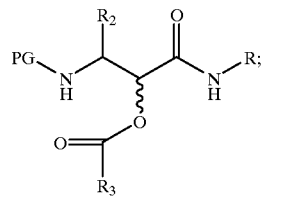

(b) removing protecting group PG from the amino α-acyloxycarboxamide derivative from step (a) under PG group removing conditions which include a pH of about 6 to about 9 thereby effecting acyl migration to give an α-hydroxy-β-aminoamide derivative of formula (CI); and (c) treating the derivative of formula (CI) from step (b) under oxidizing conditions to give an a-ketoamide derivative of formula (CII).

18. A method of preparing a semi-carbazone protected ketoamide derivative of formula (CIII):

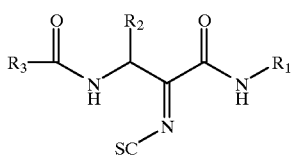

(CIII)

wherein (i)

(a) $R_1$, $R_2$ and $R_3$ are independently selected from the group consisting of alkyl of 1 to about 12 carbon atoms, cycloalkyl of 3 to about 12 carbon atoms, alkenyl of 2 to about 12 carbon atoms, cycloalkenyl of 5 to about 12 carbon atoms, and alkynyl 3 to about 12 carbon atoms, all optionally substituted with 1 to 3 substituents independently selected from the group consisting of $Y_1$, $Y_2$ and $Y_3$; aryl of about 5 to about 14 carbon atoms which is optionally mono-, di- or tri-substituted with $Y_1$, $Y_2$, or $Y_3$; heteroaryl of about 5 to about 14 ring atoms, with the ring atoms selected from carbon atoms and heteroatoms, wherein the heteroatoms are selected from oxygen, nitrogen and sulfur and which is optionally mono-, di-, tri-substituted with $Y_1$, $Y_2$ or $Y_3$; aralkyl of about 6 to about 18 carbon atoms which is optionally mono-, di- or tri-substituted on the aryl ring with $Y_1$, $Y_2$ or $Y_3$; and heteroaralkyl of about 5 to about 18 carbon atoms having about 5 to about 14 ring atoms with the ring atoms selected from carbon atoms and heteroatoms, wherein the heteroatoms are selected from oxygen, nitrogen and sulfur and which is optionally mono, di- or tri-substituted on the ring with $Y_1$, $Y_2$ or $Y_3$;

(b) alternatively $R_1$ is —$CH(R_5)C(O)W_1$ or a peptidyl substituent of the formula —$(Xaa_1)_nW_2$, wherein $R_5$ is hydrogen, alkyl of 1 to about 12 carbon atoms, cycloalkyl of 3 to about 12 carbon atoms, aryl of 5 to about 14 carbon atoms, or aralkyl of about 7 to about 15 carbon atoms, all optionally substituted with 1 to 3 substituents independently selected from hydroxy, sulfhydryl, alkylthio, carboxyl, amide, amino alkylamino, indolyl, 3-N-formylindolyl, benzyloxy, halobenzyloxy, guanidino, nitroguanidino or imidazolyl optionally substituted with alkoxyalkyl; $W_1$ and $W_2$ are independently selected from —OH, —$OZ_1$, —SH, —$SZ_1$, —$NH_2$, —$NHZ_1$, and —$NZ_1Z_2$; each $Xaa_1$ is an independently selected amino acid residue and n is an integer from 1 to 10; or (c) alternatively $R_3C(O)$— is $W_1CH(R_5)C(O)$— or $R_4$ wherein $R_4$ is a peptide substituent of the formula $Z_1X(Xaa_2)_r$— wherein each $Xaa_2$ is an independently selected amino acid residue, r is an integer from 1 to 10 and X is —C(O)—, —$S(O)_2$—, —OC(O)—, or a direct link;

(ii) each $Y_1$, $Y_2$ and $Y_3$ is independently selected from the group consisting of halogen, cyano, nitro, tetrazolyl, guanidino, amidino, methylguanidino, —$CH_3$, —$CH_2CH_3$, —$CH_2CH_2CH_3$, —$CH(CH_3)_2$, —$CH_2CF_3$, —$CH(CF_3)_2$, —$OCF_3$, —$OCF_2H$, —$OCF_2CF_3$, —$OC(O)NH_2$, —$OC(O)NHZ_1$, —$OC(O)NZ_1Z_2$, —$NHC(O)Z_1$, —$NHC(O)NH_2$, —$NHC(O)NHZ_1$, —$NHC(O)NHZ_1Z_2$, —$C(O)OH$, —$C(O)OZ_1$, —$C(O)NH_2$, —$C(O)NHZ_1$, —$C(O)NZ_1Z_2$, —$P(O)_3H_2$, —$P(O)_3(Z_1)_2$, —$S(O)_3H$, —$S(O)_mZ_1$, —$Z_1$, —$OZ_1$, —OH, —$NH_2$, 13 $NHZ_1$, —$NZ_1Z_2$, and —$S(O)_m(CF_2)_qCF_3$, wherein m is 0, 1 or 2, q is an integer from 0 to 5;

(iii) each $Z_1$ and $Z_2$ is independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms; and (iv) SC is —NHCONHQ wherein Q is selected from the group consisting of hydrogen, alkyl of 1 to about 12 carbon atoms, alkenyl of 2 to about 12 carbon atoms, alkynyl of 3 to about 12 carbon atoms, aryl of 5 to about 18 carbon atoms, heteroaryl of 5 to about 18 ring atoms with the ring atoms selected from carbon atoms and heteroatoms wherein the heteroatoms are selected from oxygen, nitrogen and sulfur, aralkyl, di-arylalkyl and tri-arylalkyl; which comprises treating a compound of formula (CII) prepared by the method of claim 17 with a semicarbazide of the formula $NH_2NHCONHQ$ under conditions permitting formation of a semicarbazone-protected ketoamide derivative of formula (CIII).

19. A method of preparing a compound a peptidyl ketoamide of formula (CIV):

(CIV)

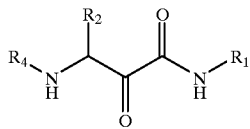

wherein
(i) $R_1$ is —CH($R_5$)C(O)$W_1$ or a peptidyl substituent of the formula —(Xaa$_1$)$_n$W$_2$, wherein $R_5$ is hydrogen, alkyl of 1 to about 12 carbon atoms, cycloalkyl of 3 to about 12 carbon atoms, aryl of 5 to about 14 carbon atoms, or aralkyl of about 7 to about 15 carbon atoms, all optionally substituted with 1 to 3 substituents independently selected from hydroxy, sulfhydryl, alkylthio, carboxyl, amide, amino alkylamino, indolyl, 3-N-formylindolyl, benzyloxy, halobenzyloxy, guanidino, nitroguanidino or imidazolyl optionally substituted with alkoxyalkyl; $W_1$ and $W_2$ are independently selected from —OH, —OZ$_1$, —SH, —SZ$_1$, —NH$_2$, —NHZ$_1$ and —NZ$_1$Z$_2$; each Xaa$_1$ is an independently selected amino acid residue and n is an integer from 1 to 10;
(ii) $R_2$ is independently selected from the group consisting of alkyl of 1 to about 12 carbon atoms, cycloalkyl of 3 to about 12 carbon atoms, alkenyl of 2 to about 12 carbon atoms, cycloalkenyl of 5 to about 12 carbon atoms, and alkynyl 3 to about 12 carbon atoms, all optionally substituted with 1 to 3 substituents independently selected from the group consisting of $Y_1$, $Y_2$ and $Y_3$; aryl of about 5 to about 14 carbon atoms which is optionally mono-, di- or tri-substituted with $Y_1$, $Y_2$, or $Y_3$; heteroaryl of about 5 to about 14 ring atoms, with the ring atoms selected from carbon atoms and heteroatoms, wherein the heteroatoms are selected from oxygen, nitrogen and sulfur and which is optionally mono-, di-, tri-substituted with $Y_1$, $Y_2$ or $Y_3$; aralkyl of about 6 to about 18 carbon atoms which is optionally mono-, di- or tri-substituted on the aryl ring with $Y_1$, $Y_2$ or $Y_3$; and heteroaralkyl of about 5 to about 18 carbon atoms having about 5 to about 14 ring atoms with the ring atoms selected from carbon atoms and heteroatoms, wherein the heteroatoms are selected from oxygen, nitrogen and sulfur and which is optionally mono, di- or tri-substituted on the ring with $Y_1$, $Y_2$ or $Y_3$;
(iii) $R_4$ is a peptidyl substituent of the formula Z$_1$X(Xaa$_2$)$_r$— wherein each Xaa$_2$ is an independently selected amino acid residue, r is an integer from 1 to 10 and X is —C(O)—, —S(O)$_2$13 , —OC(O)—, or a direct link;
(iv) each $Y_1$, $Y_2$ and $Y_3$ is independently selected from the group consisting of halogen, cyano, nitro, tetrazolyl, guanidino, amidino, methylguanidino, —CH$_3$, —CH$_2$CH$_3$, —CH$_2$CH$_2$CH$_3$, —CH(CH$_3$)$_2$, —CH$_2$CF$_3$, —CH(CF$_3$)$_2$, —OCF$_3$, —OCF$_2$H, —OCF$_2$CF$_3$,—OC(O)NH$_2$,—OC(O)NHZ$_1$,—OC(O)NZ$_1$Z$_2$, —NHC(O)Z$_1$, —NHC(O)NH$_2$, —NHC(O)NHZ$_1$, —NHC(O)NHZ$_1$Z$_2$, —C(O)OH, —C(O)OZ$_1$, —C(O)NH$_2$, —C(O)NHZ$_1$, —C(O)NZ$_1$Z$_2$, —P(O)$_3$H$_2$, —P(O)$_3$(Z$_l$)$_2$, —S(O)$_3$H, —S(O)$_m$Z$_1$, —Z$_1$, —OZ$_1$, —OH, —NH$_2$, —NHZ$_1$, —NZ$_1$Z$_2$, N-morpholino, —S(CF$_2$)$_q$CF$_3$, and —S(O)$_m$(CF$_2$)$_q$CF$_3$, wherein m is 0, 1 or 2, q is an integer from 0 to 5; and
(v) each $Z_1$ and $Z_2$ is independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms; comprising steps of:
(a) reacting an N-terminally blocked aminoaldehyde of the formula PGNHCH(R$_2$)CHO, where PG is a protecting group, with an isonitrile of the formula R$_1$NC and a peptidyl carboxylic acid of the formula R$_4$OH in solvent to give a β-amino α-acyloxycarboxamide derivative of the formula:

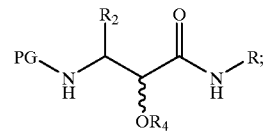

(b) removing protecting PG from the β-amino α-acyloxycarboxamide derivative from step (a) under PG removing conditions which include a pH of about 6 to about 9 to give an α-hydroxy-β-aminoamide derivative of the formula

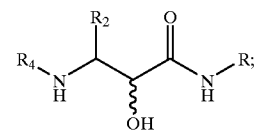

and
(c) treating the α-hydroxy-β-aminoamide derivative from step (b) under oxidizing conditions to give a peptidyl ketoamide derivative of formula (CIV).

20. A method of preparing an α-hydroxy β-protected aminoamide derivative of the formula (CV):

(CV)

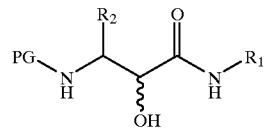

comprising the steps of:
(a) reacting an N-terminally blocked aminoaldehyde of the formula PGNHCH(R$_2$)CHO, an isonitrile of the formula R$_1$NC, and a carboxylic acid of the formula R$_3$CO$_2$H in solvent to give an amino α-acyloxycarboxamide of the formula:

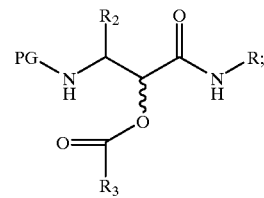

and
(b) treating the amino α-acyloxycarboxamide derivative and selective hydrolysis conditions to hydrolyze the α-acyloxy group to a α-hydroxy β-protected aminoamide derivative of formula (CV), wherein (i) PG is a protecting group; or (ii)
- (a) $R_1$, $R_2$ and $R_3$ are independently selected from the group consisting of alkyl of 1 to about 12 carbon atoms, cycloalkyl of 3 to about 12 carbon atoms, alkenyl of 2 to about 12 carbon atoms, cycloalkenyl of 5 to about 12 carbon atoms, and alkynyl 3 to about 12 carbon atoms, all optionally substituted with 1 to 3 substituents independently selected from the group consisting of $Y_1$, $Y_2$ and $Y_3$; aryl of about 5 to about 14 carbon atoms which is optionally mono-, di- or tri-substituted with $Y_1$, $Y_2$, or $Y_3$; heteroaryl of about 5 to about 14 ring atoms, with the ring atoms selected from carbon atoms and heteroatoms, wherein the heteroatoms are selected from oxygen, nitrogen and sulfur and which is optionally mono-, di-, tri-substituted with $Y_1$, $Y_2$ or $Y_3$; aralkyl of about 6 to about 18 carbon atoms which is optionally mono-, di- or tri-substituted on the aryl ring with $Y_1$, $Y_2$ or $Y_3$; and heteroaralkyl of about 5 to about 18 carbon atoms having about 5 to about 14 ring atoms with the ring atoms selected from carbon atoms and heteroatoms, wherein the heteroatoms are selected from oxygen, nitrogen and sulfur and which is optionally mono, di- or tri-substituted on the ring with $Y_1$, $Y_2$ or $Y_3$;
- (b) alternatively $R_1$ is —$CH(R_5)C(O)W_1$ or a peptidyl substituent of the formula —$(Xaa_1)_nW_2$, wherein $R_5$ is hydrogen, alkyl of 1 to about 12 carbon atoms, cycloalkyl of 3 to about 12 carbon atoms, aryl of 5 to about 14 carbon atoms, or aralkyl of about 7 to about 15 carbon atoms, all optionally substituted with 1 to 3 substituents independently selected from hydroxy, sulfhydryl, alkylthio, carboxyl, amide, amino alkylamino, indolyl, 3-N-formylindolyl, benzyloxy, halobenzyloxy, guanidino, nitroguanidino or imidazolyl optionally substituted with alkoxyalkyl; $W_1$ and $W_2$ are independently selected from —OH, —$OZ_1$, —SH, —$SZ_1$, —$NH_2$, —$NHZ_1$ and —$NZ_1Z_2$; each $Xaa_1$ is an independently selected amino acid residue and n is an integer from 1 to 10; or
- (c) alternatively $R_3C(O)$— is $W_1CH(R_5)C(O)$— or $R_4$ wherein $R_4$ is a peptidyl substituent of the formula $Z_1X(Xaa_2)_r$— wherein each $Xaa_2$ is an independently selected amino acid residue, r is an integer from 1 to 10 and X is —C(O)—, —$S(O)_2$—, —OC(O)—, or a direct link;

(iii) each $Y_1$, $Y_2$ and $Y_3$ is independently selected from the group consisting of halogen, cyano, nitro, tetrazolyl, guanidino, amidino, methylguanidino, —$CH_3$, —$CH_2CH_3$, —$CH_2CH_2CH_3$, —$CH(CH_3)_2$, —$CH_2CF_3$, —$CH(CF_3)_2$, —$OCF_3$, —$OCF_2H$, —$OCF_2CF_3$, —$OC(O)NH_2$, —$OC(O)NHZ_1$, —$OC(O)NZ_1Z_2$, —$NHC(O)Z_1$, —$NHC(O)NH_2$, —$NHC(O)NHZ_1$, —$NHC(O)NHZ_1Z_2$, —C(O)OH, —$C(O)OZ_1$, —$C(O)NH_2$, —$C(O)NHZ_1$, —$C(O)NZ_1Z_2$, —$P(O)_3H_2$, —$P(O)_3(Z_1)_2$, —$S(O)_3H$, —$S(O)_mZ_1$, —$Z_1$, —$OZ_1$, —OH, —$NH_2$, —$NHZ_1$, —$NZ_1Z_2$, N-morpholino, —$S(CF_2)_qCF_3$, and —$S(O)_m(CF_2)_qCF_3$, wherein m is 0, 1 or 2, q is an integer from 0 to 5; and (iv) each $Z_1$ and $Z_2$ is independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms.

21. A method according to claim 20 wherein said selective hydrolysis conditions comprise an alkali metal alkoxide.

* * * * *